US010682409B2

(12) United States Patent
Sears et al.

(10) Patent No.: US 10,682,409 B2
(45) Date of Patent: Jun. 16, 2020

(54) THERAPEUTIC TREATMENT

(71) Applicant: Attentive Therapeutics, Inc., Encino, CA (US)

(72) Inventors: Douglas Sears, Oak Park, CA (US); Michael Reilly, Oak Park, CA (US)

(73) Assignee: Attentive Therapeutics, Inc., Encino, CA (US)

( * ) Notice: Subject to any disclaimer, the term of this patent is extended or adjusted under 35 U.S.C. 154(b) by 0 days.

(21) Appl. No.: 16/584,877

(22) Filed: Sep. 26, 2019

(65) Prior Publication Data

US 2020/0030447 A1 Jan. 30, 2020

Related U.S. Application Data

(63) Continuation of application No. 14/046,528, filed on Oct. 4, 2013.

(60) Provisional application No. 61/744,948, filed on Oct. 9, 2012.

(51) Int. Cl.
| | |
|---|---|
| *A61K 45/06* | (2006.01) |
| *A61K 31/451* | (2006.01) |
| *A61K 31/4458* | (2006.01) |
| *A61K 31/137* | (2006.01) |
| *A61K 31/165* | (2006.01) |

(52) U.S. Cl.
CPC ............ *A61K 45/06* (2013.01); *A61K 31/137* (2013.01); *A61K 31/165* (2013.01); *A61K 31/4458* (2013.01); *A61K 31/451* (2013.01)

(58) Field of Classification Search
CPC .............. A61K 2300/00; A61K 31/137; A61K 31/165; A61K 31/4458; A61K 31/451; A61K 45/06; A61P 25/00
See application file for complete search history.

(56) References Cited

U.S. PATENT DOCUMENTS

| | | | |
|---|---|---|---|
| 7,247,318 B2 * | 7/2007 | Krishnamurthy | .... A61K 9/5084 424/490 |
| 2004/0259809 A1 | 12/2004 | Gonzales | |
| 2005/0158384 A1 | 7/2005 | Couch et al. | |
| 2009/0053329 A1 | 2/2009 | Peters et al. | |
| 2009/0234018 A1 | 9/2009 | Mickle | |
| 2009/0239783 A1 | 9/2009 | Kirk | |
| 2014/0100249 A1 | 4/2014 | Sears et al. | |

FOREIGN PATENT DOCUMENTS

| | | |
|---|---|---|
| EP | 2906208 B1 | 8/2015 |
| EP | 3530268 A1 | 8/2019 |
| WO | 2010025251 A2 | 3/2010 |
| WO | 2014058742 A1 | 4/2014 |

OTHER PUBLICATIONS

Daviss (J of Child and Adolescent Psychopharmacology, 14, 1,2004) (Year: 2004).*
Busner (Psychiatry, 2007). (Year: 2007).*
Mandelkorn (http://adhdrollercoaster.org /the-basics/all-about-medications-for-adhd-part-ii/, All about Medications for ADHD, Part II, May 28, 2010) (Year: 2010).*
Horst et al. (WWW. PediatricsConsultant360.com, Published, Oct. 2012, vol. 11. No. 10, Oct. 12, 2012) (Year: 2012).*
Concerta (CONCERTA, Extended Release, 2007), and Busner (Psychiatry, 2007) (Year: 2007).*
Chandrakala et al. (Tropical J of Pharmaceutical Research, Aug. 2011, 10, 4, 365-373). (Year: 2011).*
APA, Jul. 2011, Addressing challenging situations in the management of ADHD.
Bellisle, Effects of Diet on Behaviour and Cognition in Children, British Journal of Nutrition (2004, 92, Suppl. 2, S227-S232.
Benton, "The Role of Breakfast and a Mid-Morning Snack on the Ability of Children to Concentrate in School," Physiology & Behavior 90 (2007) 382-385.
Chandrakala et al. (Tropical J of Pharmaceutical Research, Aug. 2011, 10, 4, 365-373).
Circleofmoms (http://www.circleofmoms.com/moms-kids-adhd/how-to-help-a-12-year-old-boy-on-concerta-gain-weight-607328, 2010).
Concerta (CONCERTA, Extended Release, 2007).
Cyproheptadine (State of Florida, DOH Central Pharmacy, 2010).
Daviss (J of Child and Adolescent Psychopharmacology, 14, 1, 2004).
Dodson (Current Psychiatry, vol. 4, No. 5, Jul. 2005).
Dura-Trave et al., Effects of Osmotic-Release Methylphenidate on Height and Weight in Children with Attention-Deficit-Hyperactivity Disorder (ADHD) Following Up to Four Years of Treatment, Journal of Child Neurology 27(5) 604-609, 2012.
Extended European Search Report, Application No. EP19153534, dated Jul. 9, 2019, 8 pages.
Goodman, M.D., "The BlackBook of ADHD," Primary Psychiatry, 2010; 17(2):46-63.
Gunja et al., "A Comparison ofthe Pharmacokinetics of Oral and Sublingual Cyproheptadine," Journal of of Toxicology: Clinical Toxicology, 42:1, 79-83, DOI: 10.1081/CLT-120028749.
Guy, William "Clinical Global Impressions (028-CGI)". ECDEU Assessment Manual for Psychopharmacology. US Department of Health, Education, and Welfare, Public Health Service, Alcohol, Drug Abuse, and Mental Health Administration, National Institute of Mental Healt, Psychopharmacology Research Branch, Division of Extramural Research Programs, 1976. pp. 217-222.

(Continued)

*Primary Examiner* — Umamaheswari Ramachandran
(74) *Attorney, Agent, or Firm* — Goodwin Procter, LLP

(57) ABSTRACT

This invention discloses a treatment for a patient receiving medication to treat an attention deficit disorder such as ADHD wherein the treatment results in a loss of appetite and impairment of the patient's attentiveness. The treatment combines a treatment for an attention deficit disorder with an appetite stimulant, wherein the appetite stimulant increases the caloric intake of a patient, which can increase the patient's attentiveness. The combination treatment can be given for an indefinite, including, without limitation, lifelong, to allow a patient to maintain normal caloric intake during treatment for an attention deficit disorder.

19 Claims, 22 Drawing Sheets

(56) References Cited

OTHER PUBLICATIONS

Horst et al. (www.PediatricsConsultant360.com, Published Oct. 2012, vol. 11, No. 10, Oct. 12, 2012).

International Search Report PCT/US2013/063533, dated Jan. 13, 2014.

Mandelkorn (http://adhdrollercoaster.org/the-basics/all-about-medications-for-adhd-part-ii/, All about Medications for ADHD, Part II, May 29, 2010).

Mezerji et al., "Preventive Effect of Cyproheptadine on Sleep and Appetite Disorders Induced by methylphenidate: An Exploratory Randomised, Double-blinded, Placebo-Controlled Clinical Trial," International Journal of Psychiatry in Clinical Practice, DOI: 10.1080/13651501.2018.1509095, 2018, 9 pages.

Orthen-Gambill, "Antihistaminic Drugs Increase Feeding, While Histidine Suppresses Feeding in Rats," Pharmacology Biochemistry & Behavior, vol. 31, 1988, pp. 81-86.

Pliszka, Steven, and AACAP Work Group on Quality Issues. "Practice parameter for the assessment and treatment of children and adolescents with attention-deficit/hyperactivity disorder." Journal of the American Academy of Child & Adolescent Psychiatry 46,7 (2007): 894-921.

Pollitt et al., "Fasting and Cognition in Well- and Undernourished Schoolchildren: A Review of Three Experiemental Studies," Am J Clin Nutr 1998;67 (Suppl): 779S-784S.

Prince, Pharmacotherapy of Attention-Deficit Hyperactivity Disorder in Children and Adolescents: Update on New Stiimulant Preparations, Atomoxetine, and Novel Treatments, Child and Adolescent Psychiatric Clinics of North America 15 (2006) 13-50.

Supplementary European Search Report EP13846073, dated Nov. 5, 2016.

Pollitt, E. & Gorman, K. S. (1994) Nutritional deficiencies as developmental risk factors. In C.A. Nelson (Ed.), The Minnesota symposia on child psychology: vol. 27: Threats to optimal development (pp. 121-144). Hillsdale, N. J,: Lawrence Erlbaum Associates.

* cited by examiner

Figure 1: Improvement in Attention with Increased Caloric Intake
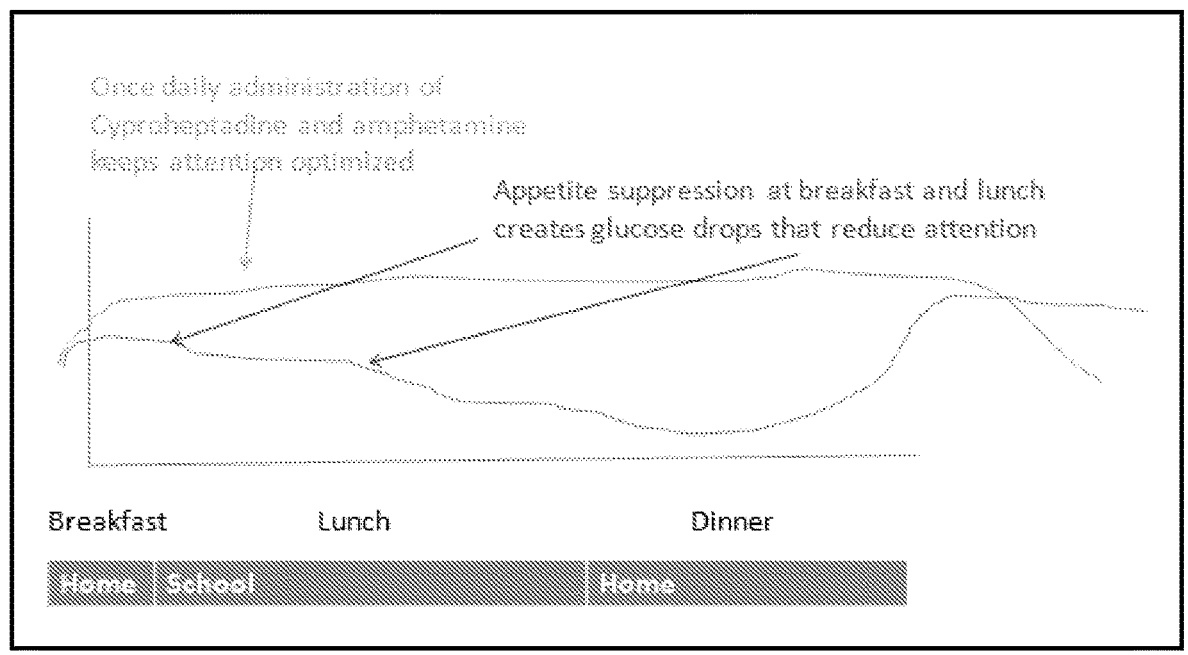

Figure 2: Impact of Combination Treatment on Weight
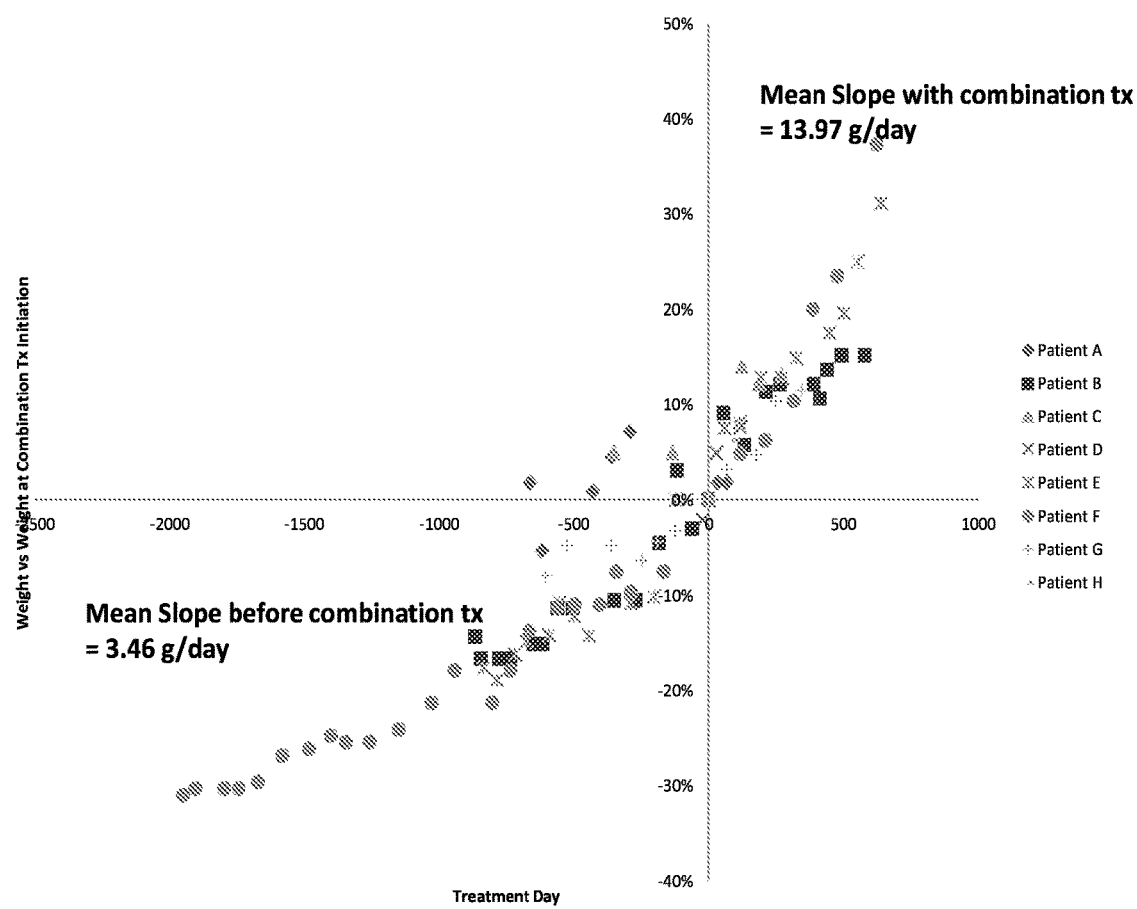

Figure 3: Impact of Combination Treatment on Height
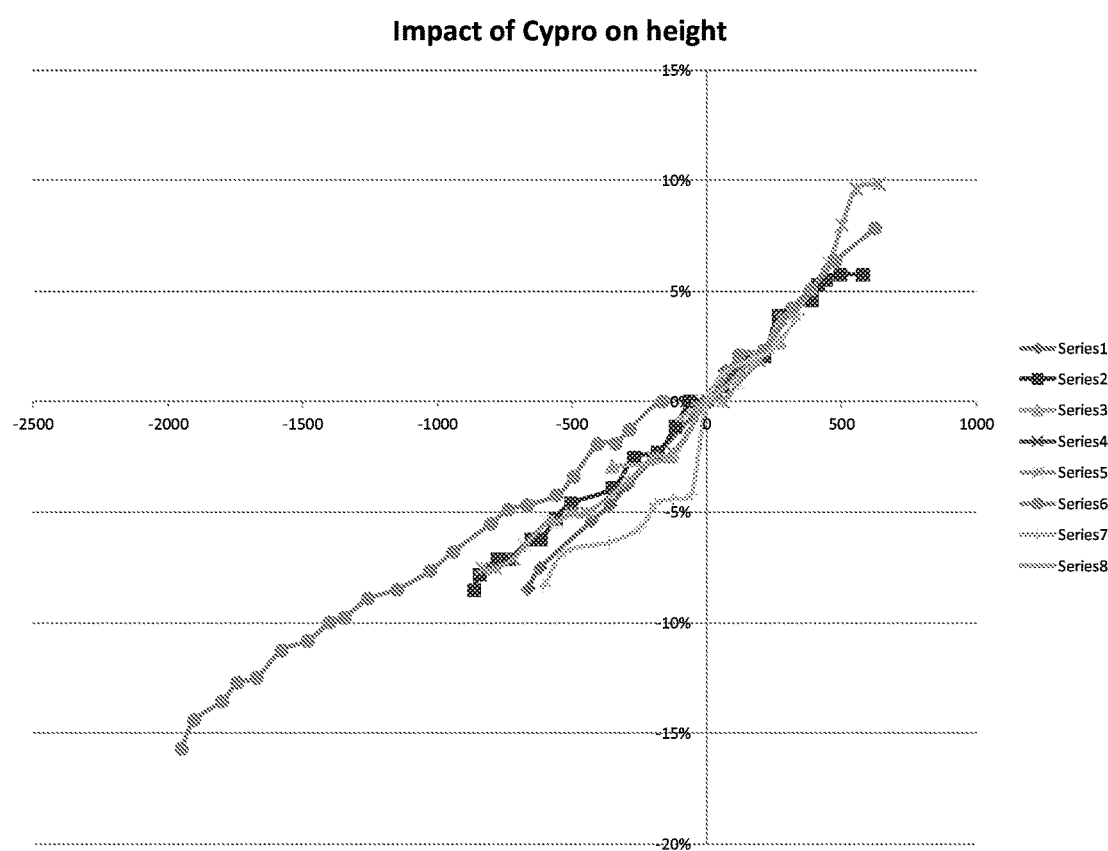

Figure 4: Change in Weight and Height for Patient A
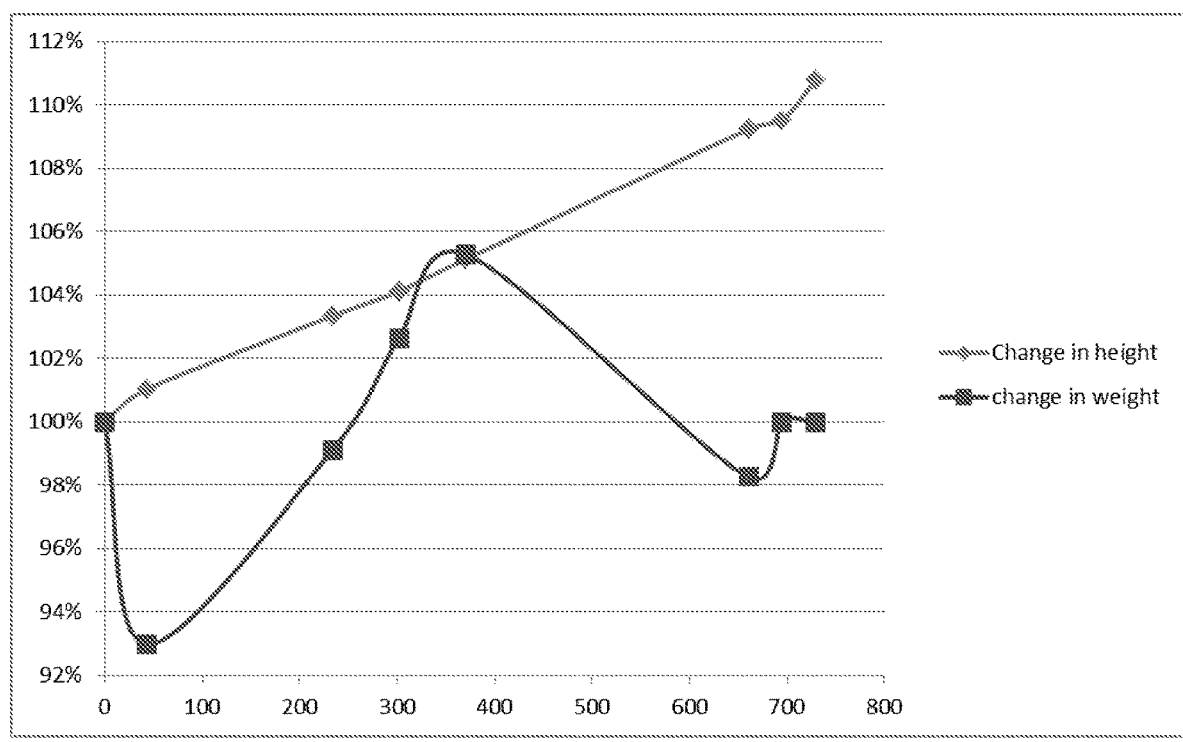

Figure 5: ADHD Sensitivity (CGI-S) for Patient A
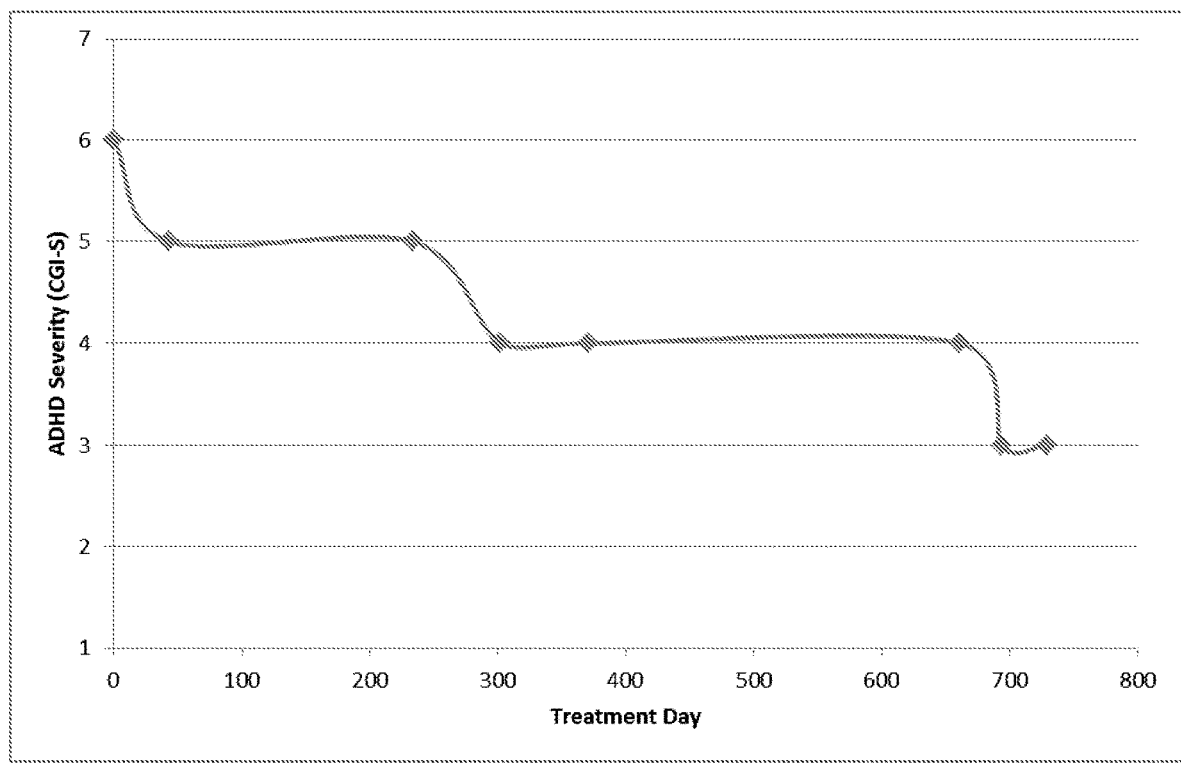

Figure 6: Change in Height and Weight of Patient B
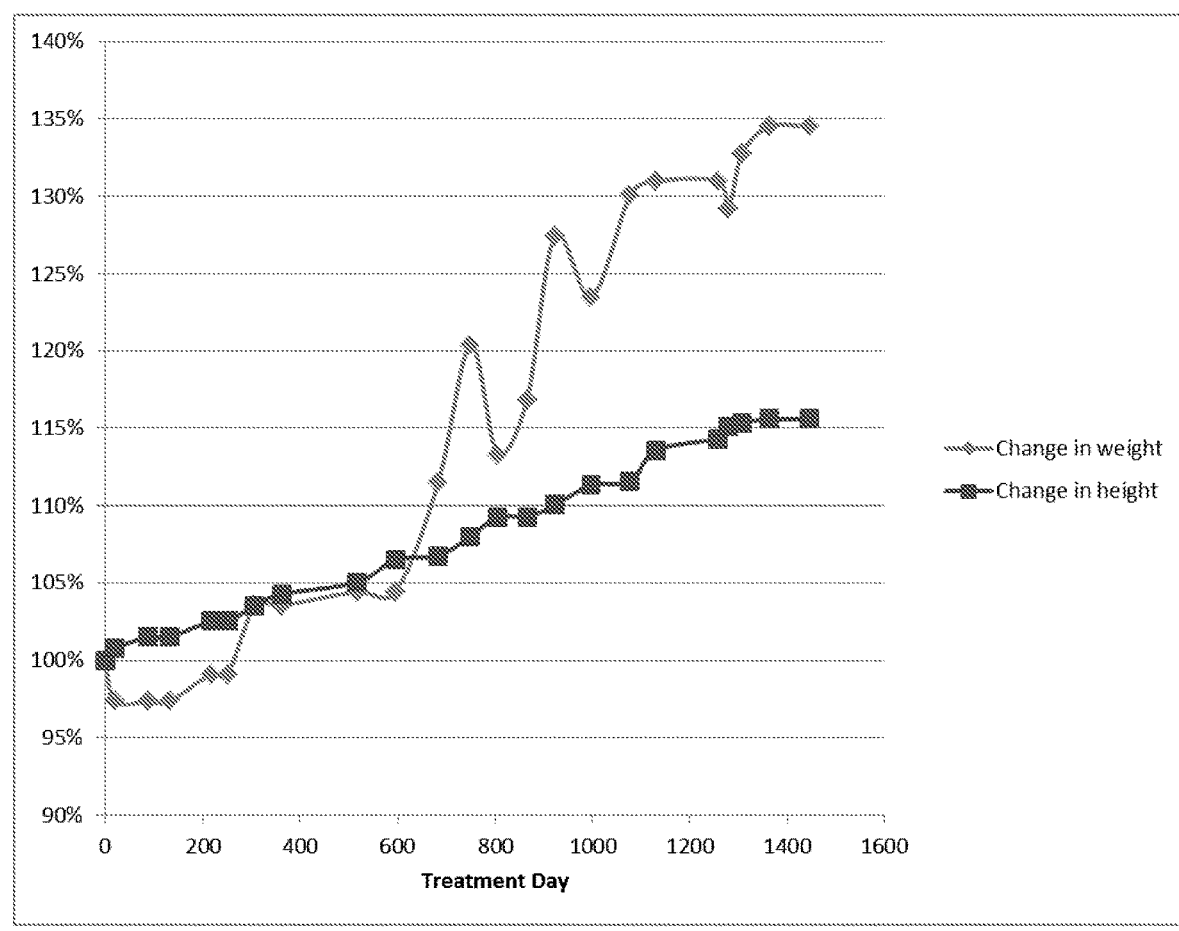

Figure 7: ADHD Sensitivity (CGI-S) for Patient A
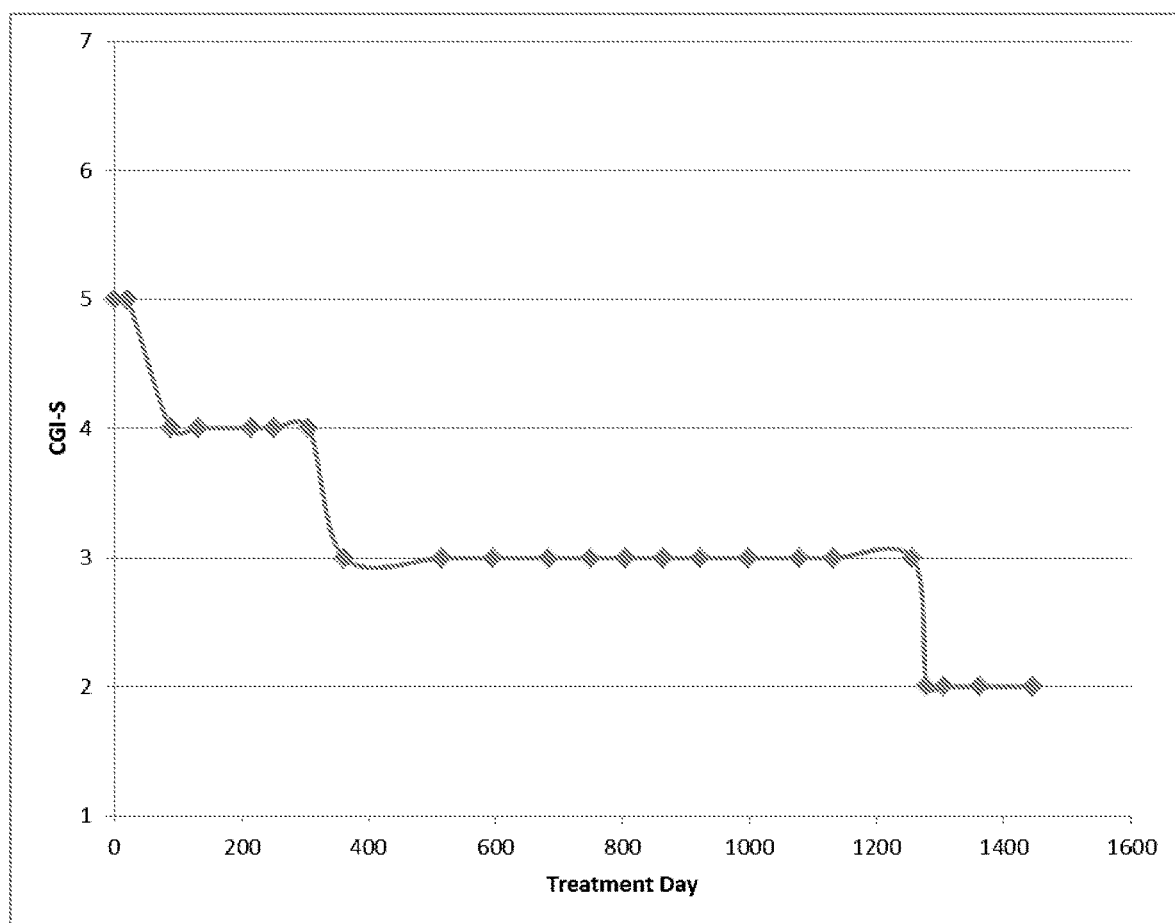

Figure 8: Change in Height and Weight for Patient C
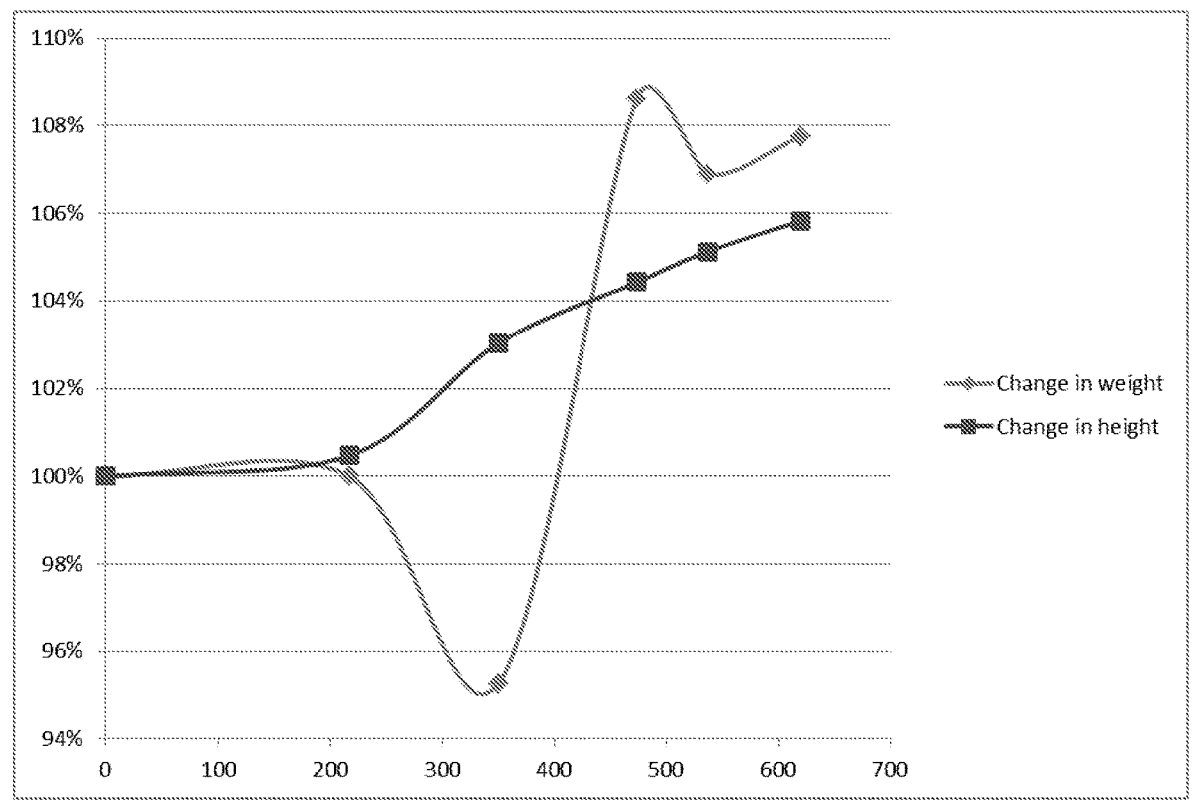

Figure 9: ADHD Sensitivity (CGI-S) for Patient C
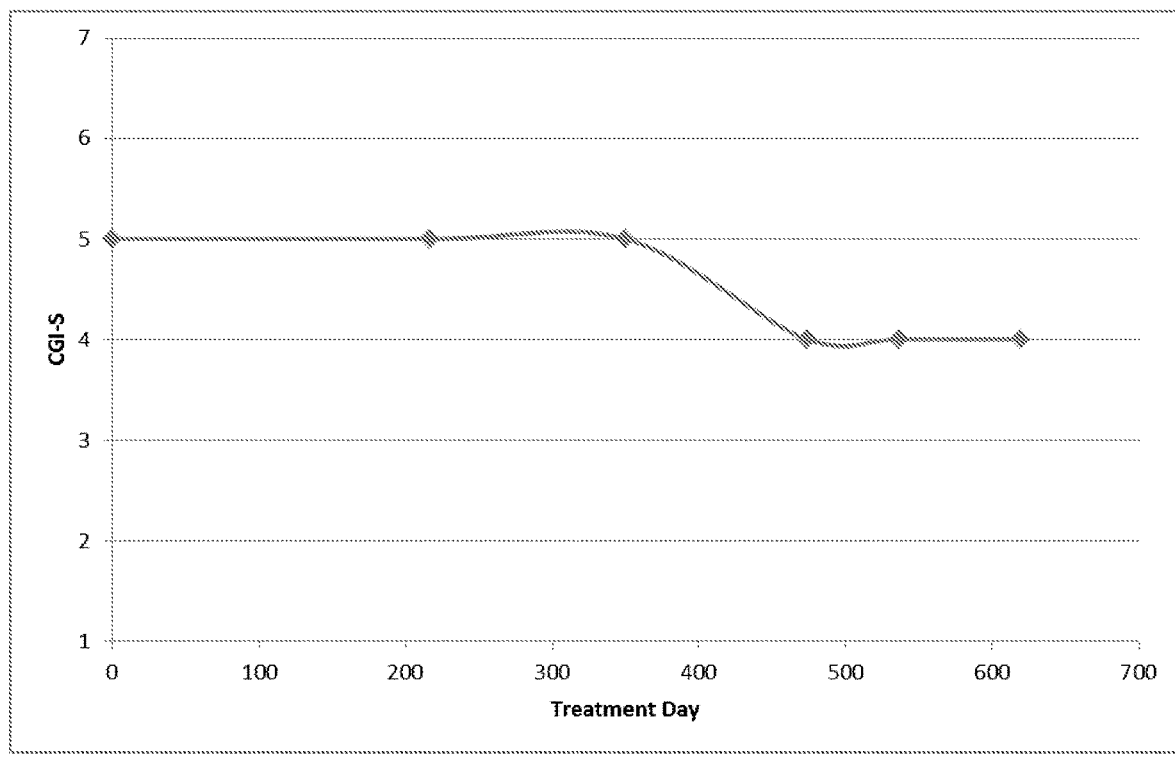

Figure 10: Change in Weight and Height of Patient D
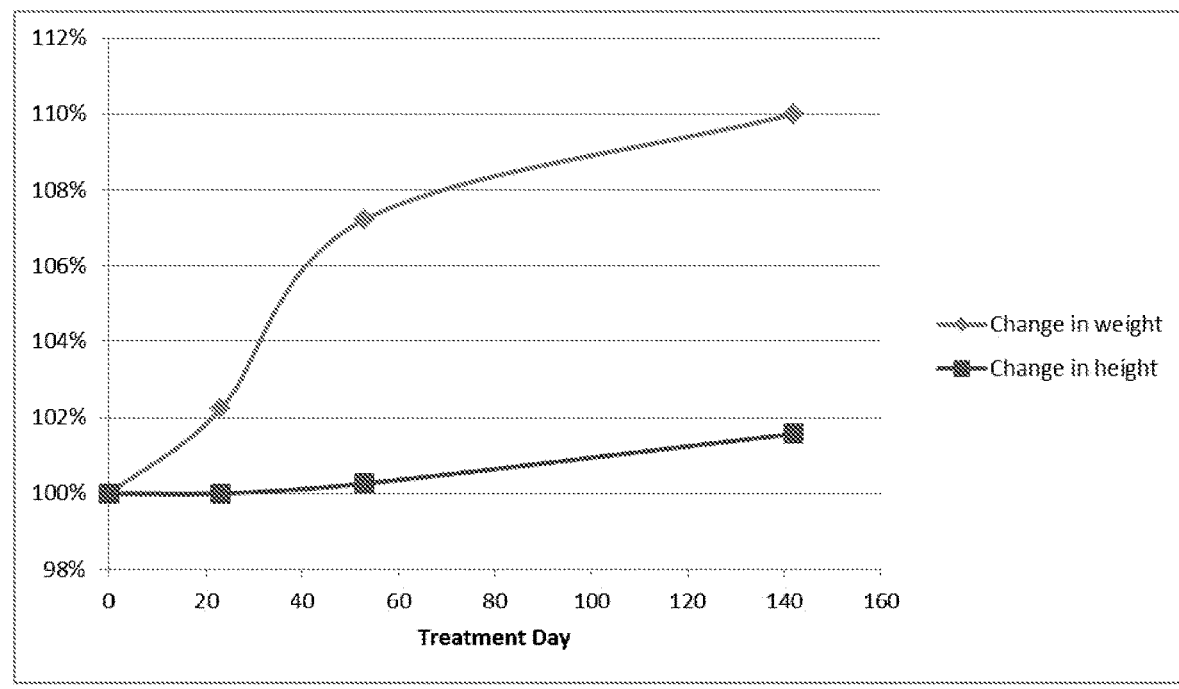

Figure 11: ADHD Sensitivity (CGI-S) for Patient D
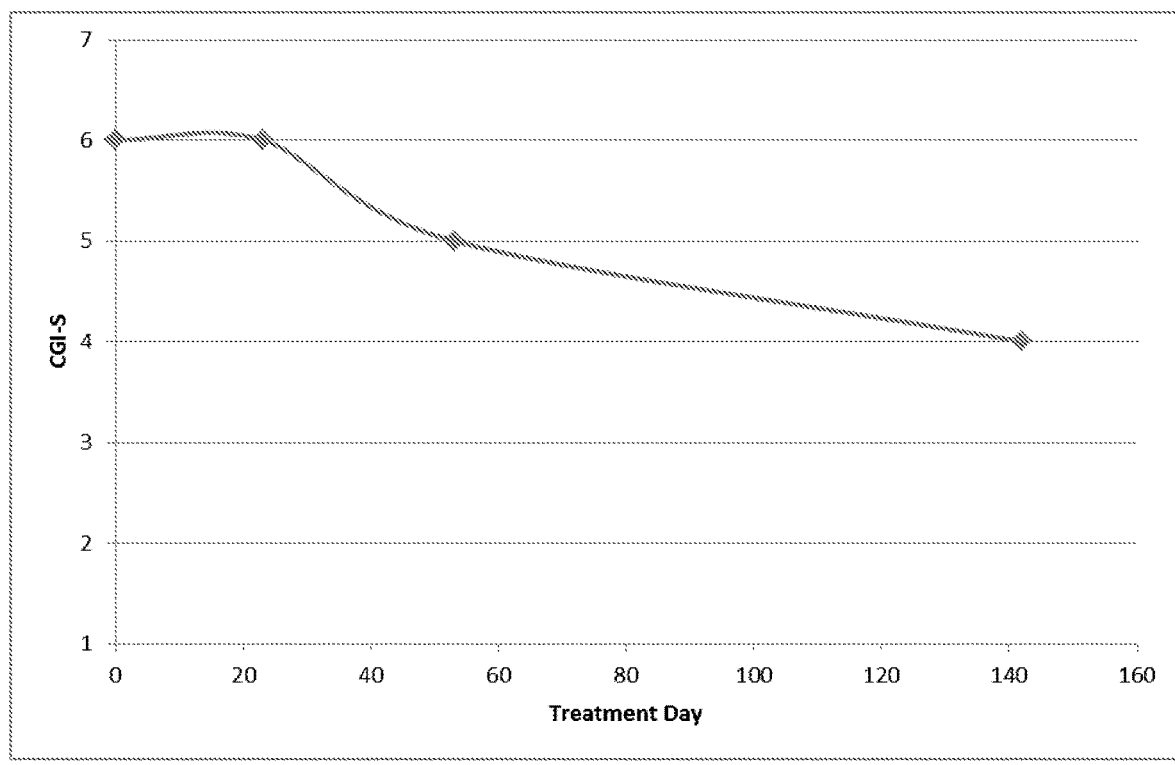

Figure 12: Change in Height and Weight of Patient E
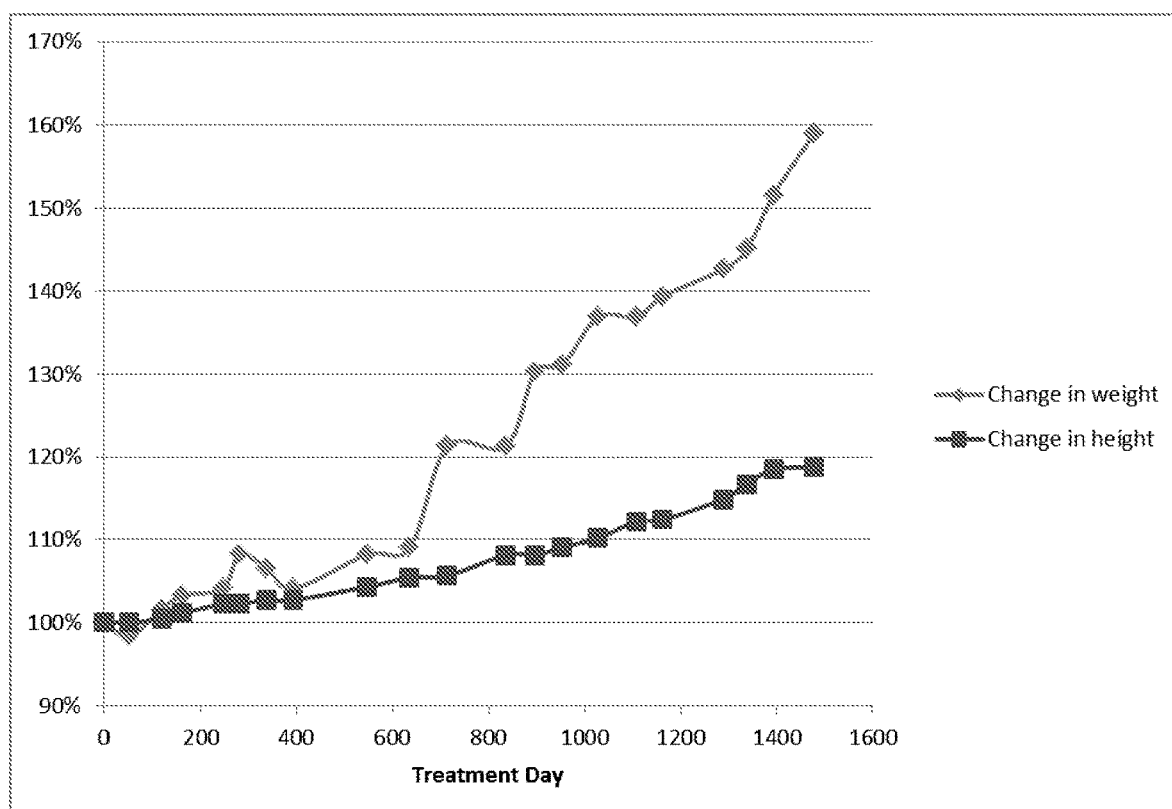

Figure 13: ADHD Sensitivity (CGI-S) for Patient E
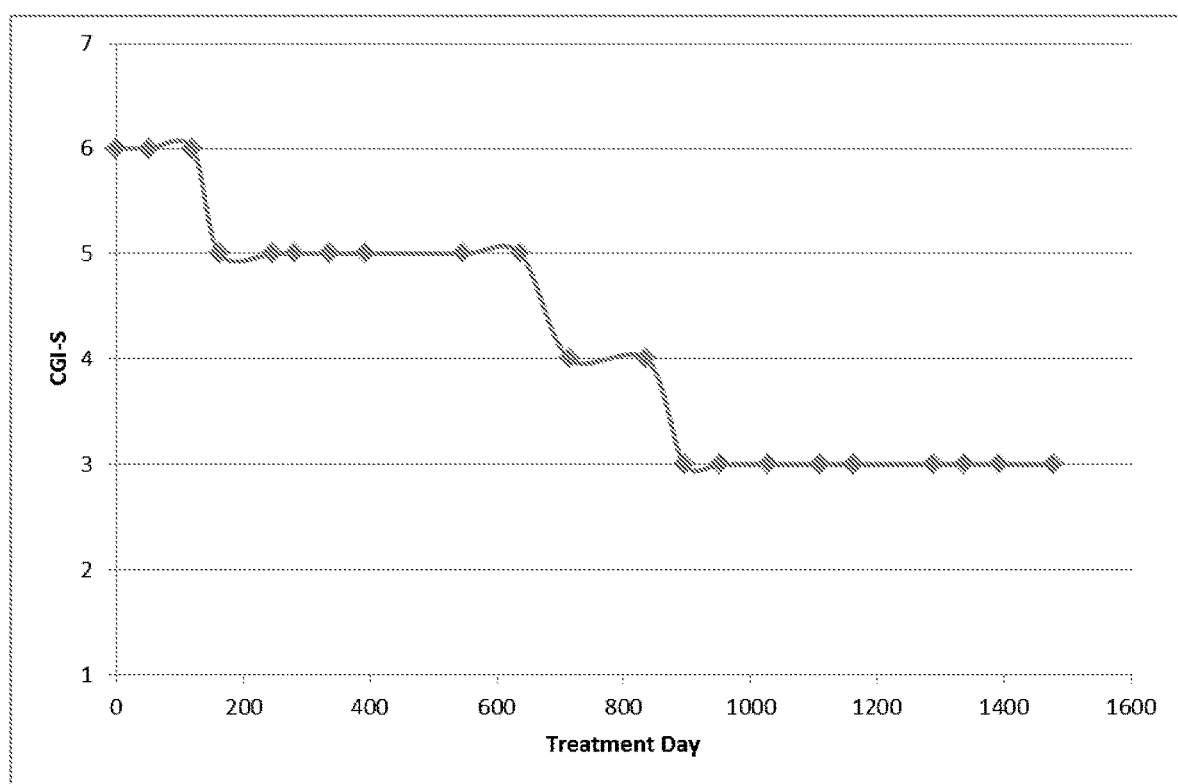

Figure 14: Change in Weight and Height of Patient F
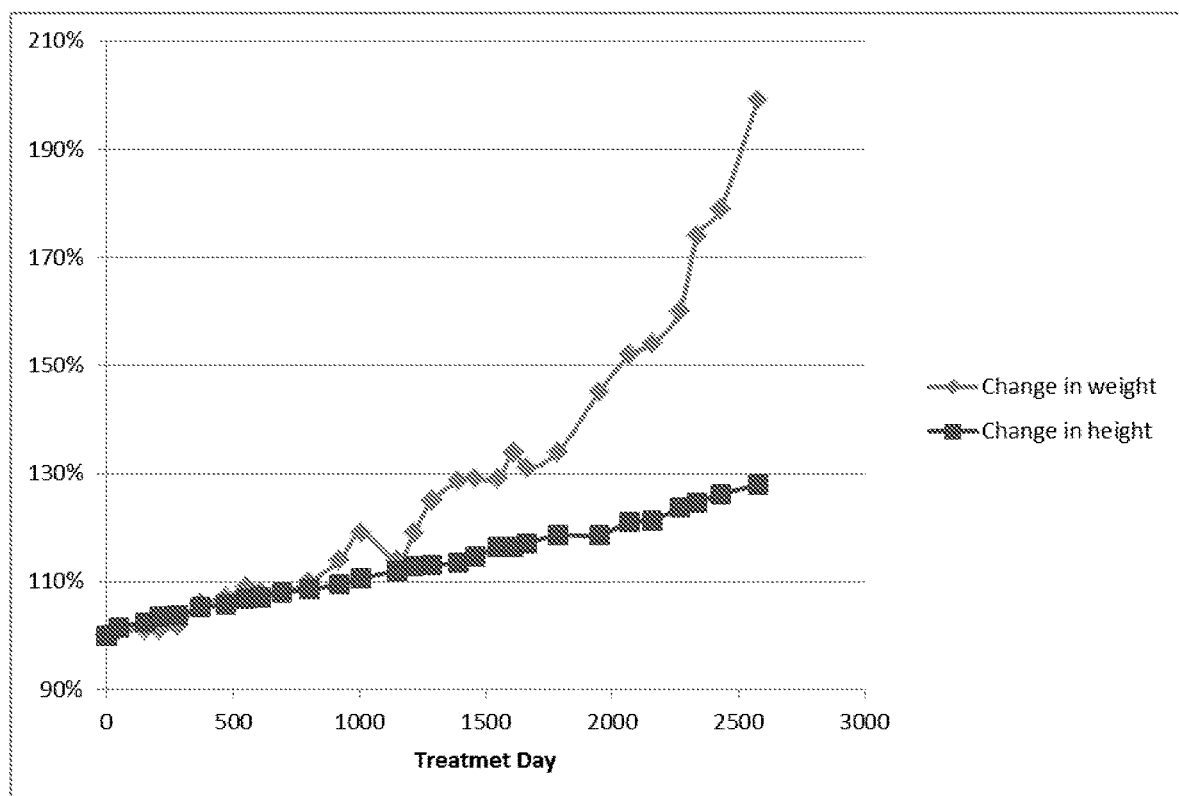

Figure 15: ADHD Sensitivity (CGI-S) for Patient F
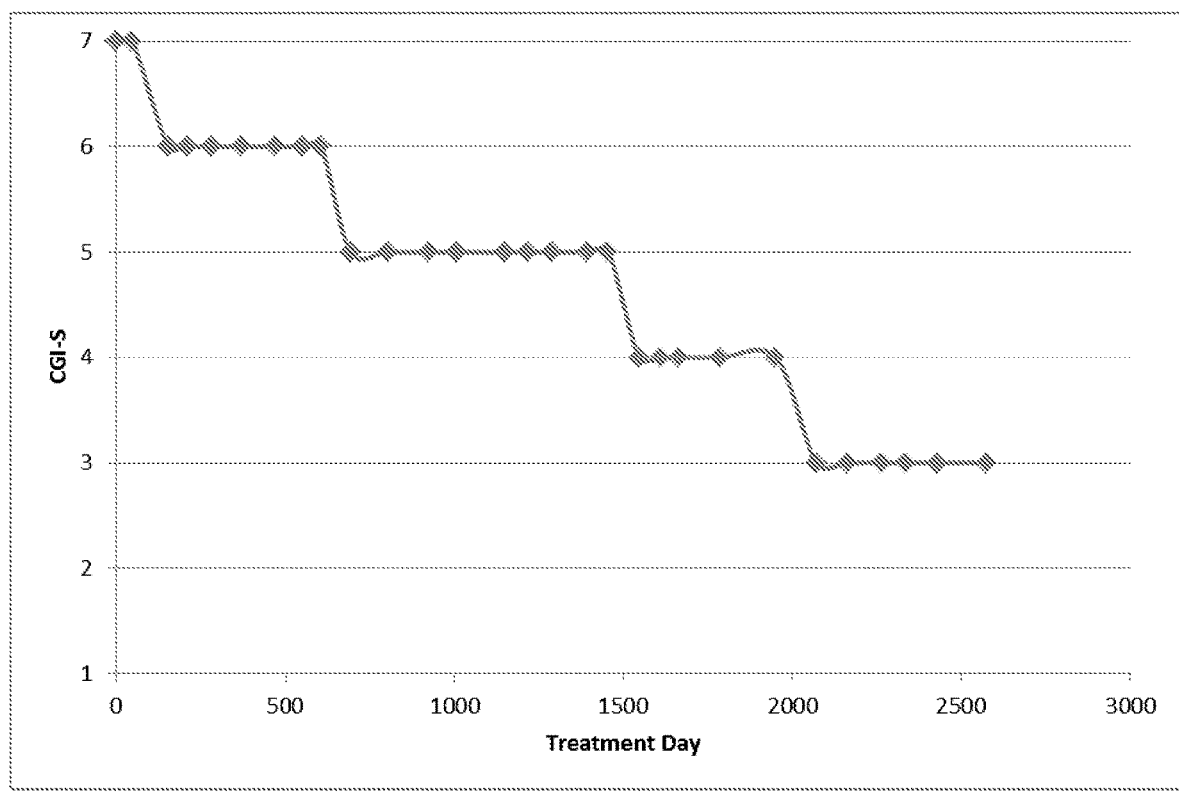

Figure 16: Weight and Height Change of Patient G
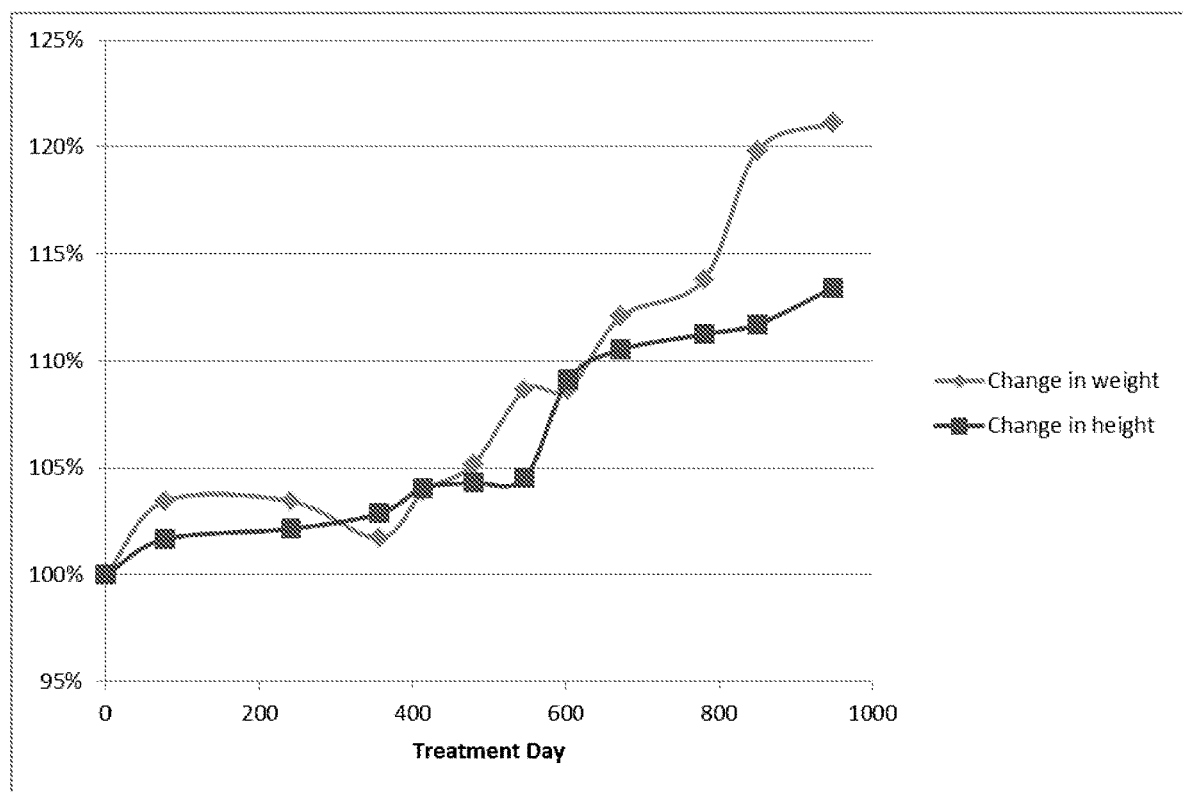

Figure 17: ADHD Sensitivity (CGI-S) for Patient G
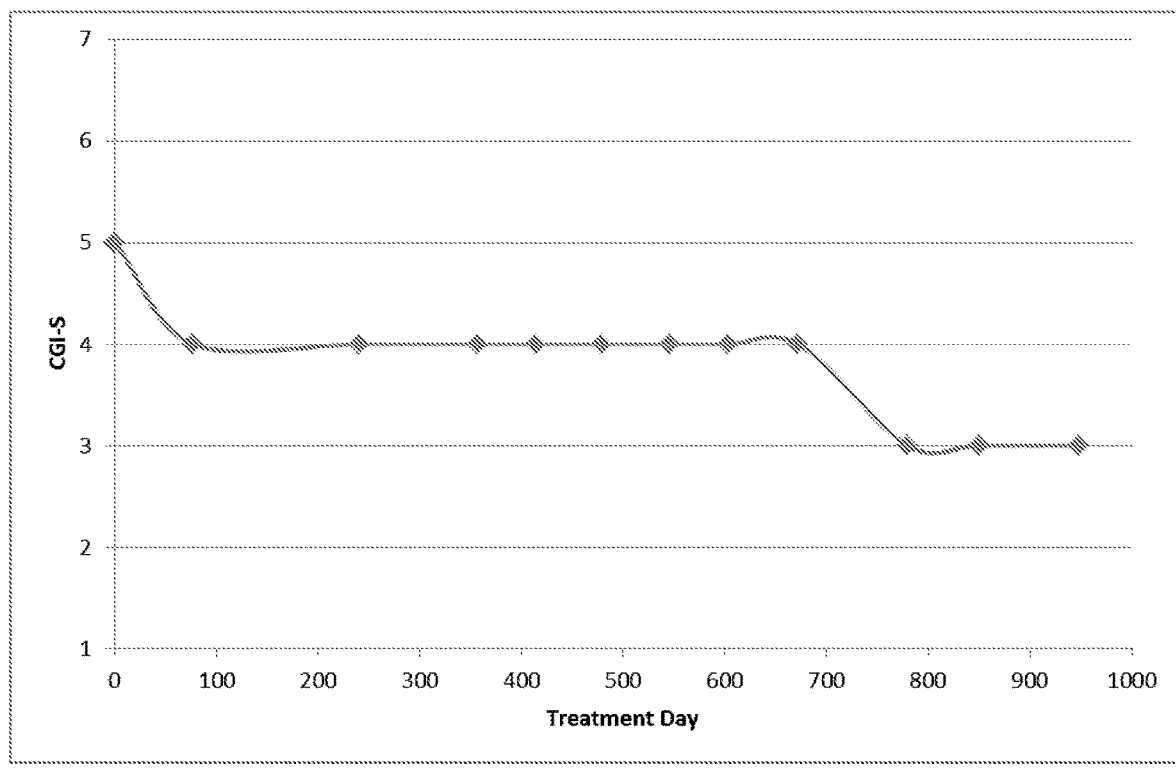

Figure 18: Weight and Height Change of Patient H
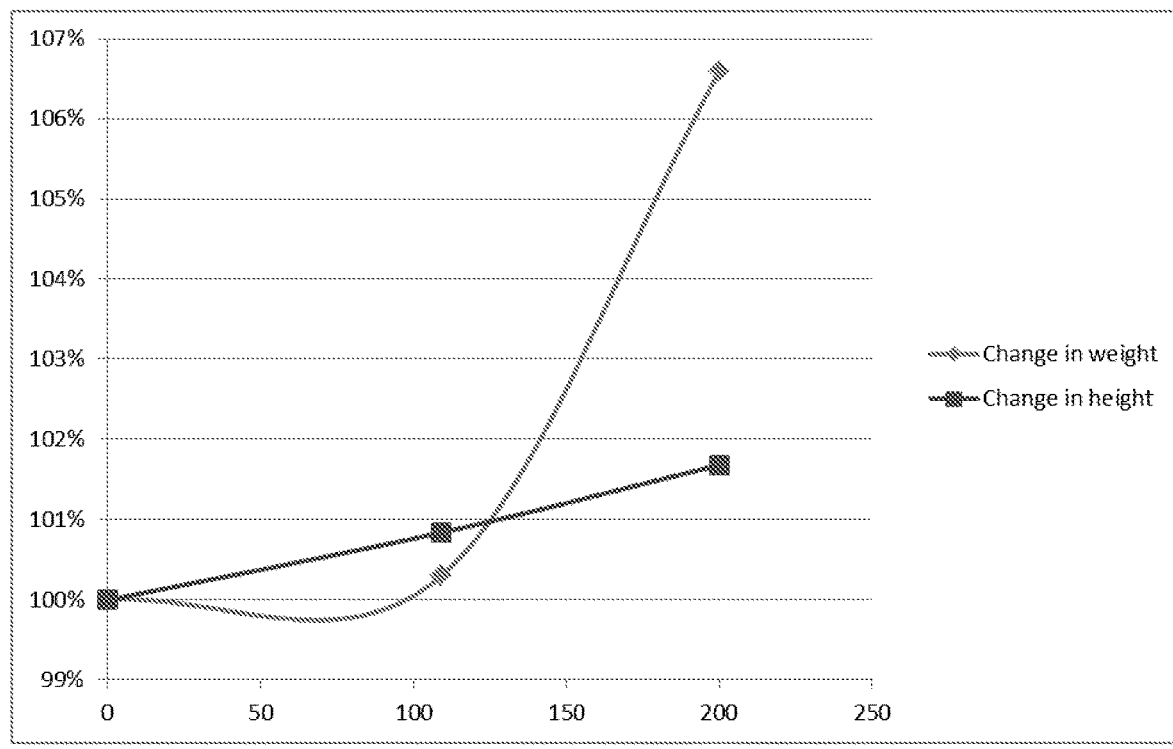

Figure 19: ADHD Sensitivity (CGI-S) for Patient H
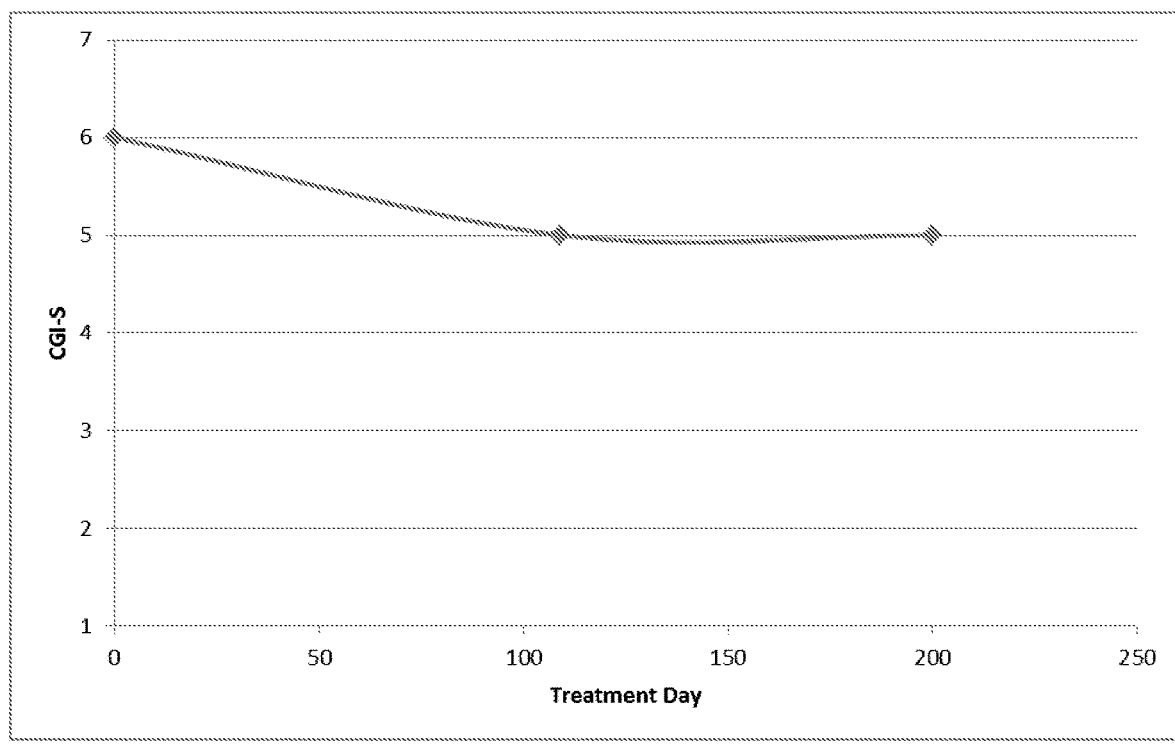

Figure 20: Impact of Combination Treatment on ADHD Severity (CGI-S)
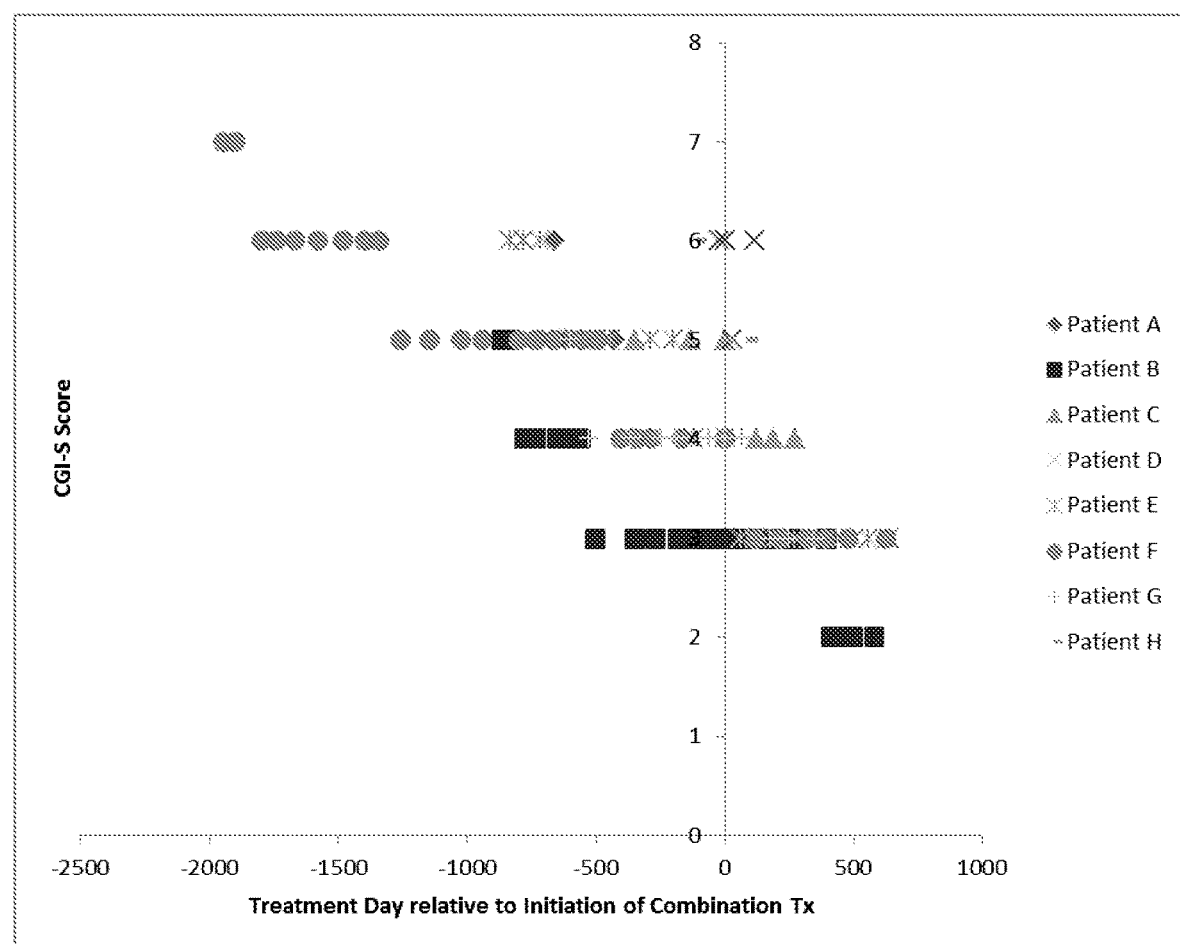

Figure 21: Impact of Treatment on ADHD Severity (CGI-S)
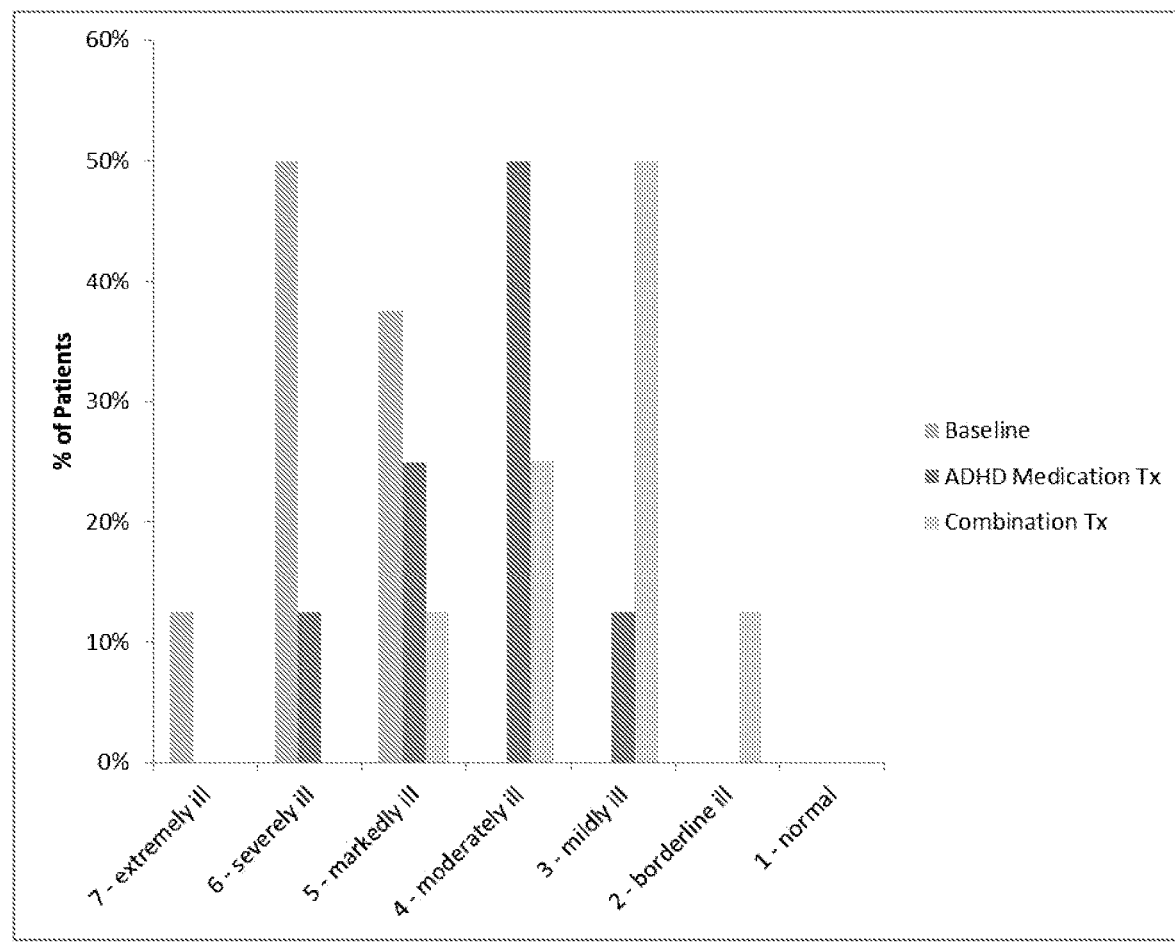

Figure 22: Impact of Treatment on Improvement in ADHD (CGI-I)
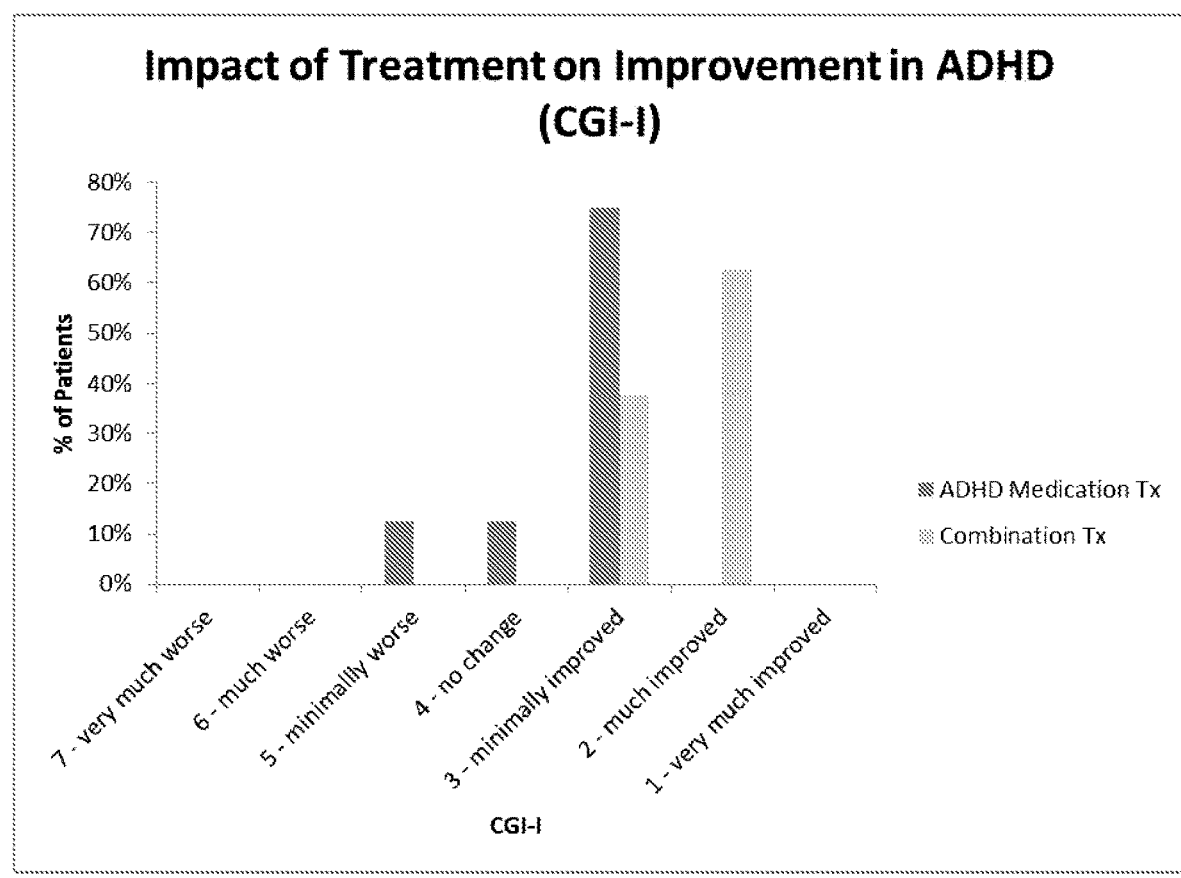

THERAPEUTIC TREATMENT

This application is a continuation of U.S. patent application Ser. No. 14/046,528, filed on Oct. 4, 2013, which claims the benefit of priority to U.S. Provisional Patent Application 61/744,948, filed on Oct. 9, 2012, which is hereby incorporated by reference in its entirety.

BACKGROUND

To treat psychological and/or neurological disorders, including without limitation, attention deficit disorder, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression, neural insult, fatigue, lethargy, binge eating disorder, schizophrenia, sleep cycle disorder, disease related fatigue in depression and fibromyalgia, cocaine addiction, Parkinson's Disease, combat and non-combat related PTSD, tic, and any other psychological and/or neurological syndrome it is common to prescribe to a patient a therapeutic regimen that includes an amphetamine and/or methylphenidate. An attention deficit disorder for which these therapeutics are generally prescribed is attention deficit hyperactivity disorder, also known as ADHD. ADHD is one of the most common childhood psychiatric conditions. It has been diagnosed in approximately 8.4% of all children aged 3-17 years old (Center for Disease Control and Prevention). Although scientists and clinicians debate the best way to diagnose and treat ADHD, there is no debate among competent and well-informed health care professionals that ADHD is a valid neurobiological condition that causes significant impairment to children who suffer from it.

The clinical practice parameters followed by doctors inform them that ADHD is a chronic condition that will most likely to persist into adulthood. The current standard of care recommendations state treatment should be 7 days a week, 12 months a year with no drug holidays. (see, for example, AACAP, 2007). Untreated ADHD is to known to have significant long-term consequences including loss of academic performance, social performance, and more aberrant behaviors including substance abuse, teen pregnancies and imprisonment.

Among the functional impacts of ADHD in children and adolescents are a higher risk of injury, including, without limitation bicycle/pedestrian injury, head injury and multiple injuries that require admission to an intensive care unit. Other functional impacts of ADHD include a higher rate of failure in school, higher risk of expulsion or dropout, higher rate of associated learning disability and lower rates of high school or college completion. Additionally, functional impacts of ADHD include a lack of friendships, less liked by their peers compared to non-ADHD peers, difficulty retaining peer status, a two times higher risk for tobacco smoking, a two and a half time higher risk for alcohol abuse, a two times higher risk for substance abuse, are four times more likely to contract an STD, a ten times higher risk for unplanned pregnancy, a two to six times higher rate of suspended or revoked driver's license, more traffic violations and speeding tickets, more motor vehicle accidents and greater vehicular damage. (Goodman D W, Primary Psychiatry: 17, 2 2010)

Among the function impacts of ADHD in adults are similar to those found in children and adolescents, but also include a higher likelihood of being fired or quitting a job impulsively, reduced salary, poorer work performance scores, more frequent job changes, three times more likely to be unemployed, lower occupational attainment than patient IQ would predict. Other functional impacts include a two times more likely chance to be arrested, three times more likely to be convicted, fifteen times more likely to be incarcerated, a greater tendency toward antisocial/criminal behaviour, a lower household income, higher accident claims and higher cost of accidents. (Goodman D W, Primary Psychiatry: 17, 2 2010)

Various drugs and methods have been used to treat ADHD, including amphetamine and methylphenidate based drugs. While these drugs are generally effective in treating ADHD, the side effects suffered by the children taking them can include loss of appetite resulting in weight loss, insomnia, drug dependence and loss of attentiveness.

With regard to treatments for ADHD, one option generally followed by clinicians is to prescribe the use of short-acting stimulants. These are often used as an initial treatment in small children (<16 kg), but these drugs have the disadvantage of requiring that they be administered twice a day ("b.i.d.") or three times a day ("t.i.d.") to provide control over a child's ADHD symptoms throughout day. Longer acting stimulants offer greater convenience, confidentiality, and compliance with single daily dosing, but the side effects suffered with these once a day drugs by children taking them is frequently more severe than the b.i.d. or t.i.d. ones.

But there are significant problems with therapeutic use of amphetamines and methylphenidates for the treatment of any neurological or psychological syndrome. For ADHD, the drugs are reported to be associated with loss of appetite in roughly 35% of patients as well as weight loss in approximately 15% of patients. In practice, it is not unusual to find that the frequency of appetite reduction and the amount of weight loss is actually greater than what has been reported in the scientific literature. (Sears clinical observation). While this effect is perceived as positive by patients who are taking amphetamines as a weight loss medication, it can be detrimental to the health and proper development of children taking medications for ADHD and other psychiatric disorders.

It is widely recognized in ADHD patients, and especially in children, that there is a documented link between patients missing meals and learning impairment. For instance, overnight and morning fasting among schoolchildren was found to have a deleterious effect on the children's memory, attention, performance in academic pursuits and ability to interact with other children socially. (Pollitt et al., 1998; Pollitt and Gorman, 1994). This correlates with the finding that regularity in breakfast consumption has been linked with improvement in academic performance and psychosocial functioning as well as cognition among children. (Benton, 2001; Bellisle, 2004).

It has been widely recognized that there is a documented link between missing meals and learning impairment for ADHD patients as well as patients suffering from a neurological or psychological syndrome. A possible reason for this link may be a drop in glucose levels resulting from missing a meal, since the supply of glucose to the brain is believed to impact upon memory, mood and attentiveness. Research suggests that when engaging in cognitively demanding tasks, such as schoolwork, repeated supplies of glucose to the brain enhances cognitive functioning and improves memory, mood and attentiveness. Research on the immediate effects of glucose on cognition demonstrated that the ability of the brain to fully function appears to be sensitive to short-term fluctuations in glucose supply. (Bellisle, 2004). Patients with nutritional deficiencies are particularly susceptible to the short-term fluctuations in glucose supply that impact upon cognitive ability, attentiveness and performance of the brain. Maintaining adequate levels of glucose throughout the day contributes to optimizing cognition and attentiveness, suggesting that nutritional intake should be designed to sustain an adequate level of glucose by minimizing fluctuations in food intake during the day.

One way to overcome issues with appetite in patients with ADHD is for the parents, spouse or other caregiver to actively monitor a patient's food intake. However, this generally only works when the patient is not resistant to eating, for instance, due to loss of appetite. Moreover, parents, spouse, or other caregiver cannot generally spend all day with a patient. This is particularly true when a majority of patients spend at least a portion of their day at school or work where they eat lunch.

Clinical guidelines for ADHD have tried to cope with appetite reduction and ADHD medication. (See for example, AACAP, 2007). Particularly, where a patient suffers deleterious effects resulting from a loss of appetite including slower growth in their height, a slowing in their weight gain and a loss in the child's attentiveness. The general standard is that if a patient has a change in height or weight that crosses two percentile lines, then this suggests an aberrant growth trajectory. In these cases the general response is for the child to stop taking the drug used to treat ADHD during weekends or during a patient's vacation or summer break if in school in order to attempt to mitigate the harm suffered by the patient. One problem with this approach is that it can lead to the marked impairment of attentiveness by a patient during the periods of time when their ADHD medication is removed. One option available to a clinician is to switch the patient to a different ADHD medication. However, as these drugs are also often either an amphetamine or a methylphenidate, it is likely that the patient will suffer from the same side effects. Knowing both the benefits and side effects of current treatment regimens, in making a treatment decision, it is incumbent upon a clinician to carefully balance the benefits of medication treatment with the risks of reductions in height and weight gain and the loss of attentiveness resulting from a lack of appetite.

Therefore it would be preferable to treat the side effects such as appetite reduction that prevent the proper use and optimal levels of amphetamine and/or methylphenidate therapy that are necessary to meet the treatment guidelines to treat ADHD or other neurological or psychological syndrome. One way to do this is through the use of appetite stimulants. These include, but are not limited to, a diverse group of medications given to patients to prevent undesired weight loss in the elderly and in patients suffering from such diseases as AIDS and cancer, diseases often associated with the wasting of the body's muscle tissue as well as overall weight loss. The medical term for these drugs is orexigenic, which is derived from the Greek word for "appetite" or "desire" and includes various drugs, including, without limitation, hormones, vitamins or other compounds known to increase appetite. This can include a naturally occurring neuropeptide hormone such as ghrelin, orexin or neuropeptide Y, or a drug or compound that increases hunger and therefore enhances food consumption.

An example of an appetite enhancement drug is cyproheptadine hydrochloride (4-(5H-dibenzo[a,d]cyclohepten-5-ylidene)-1-methylpiperidine hydrochloride) ("cyproheptadine"). This drug has been used as oral monotherapy for allergy under the tradename Periactin®. It is known to reach peak plasma levels in 1-3 hours after administration and has a half-life of 8 hours. (Gunja, 2004). In the 1960s, it was recognized that this drug had several side effects that made it a suboptimal allergy treatment. Among the side effects were weight gain and drowsiness.

While weight gain was a side effect that made cyproheptadine a poor antihistamine, this side effect is desirable in children suffering weight loss due to loss of appetite from use of amphetamines or methylphenidates to treat ADHD. Cyproheptadine has been shown to cause weight gain in studies that used either non-human animals or humans. (Orthen-Gambill 1988). It has also been studied for its ability to promote weight gain in clinical trials for cancer cachexia. (Coulris). Other areas where there is interest in cyproheptadine to promote weight gain are tuberculosis, anorexia nervosa, cystic fibrosis, migrane, attention deficit disorder, migrane, anti-serotonergic side effects, underweight children, narcolepsy and any other psychological and/or neurological syndrome. (Coulris, Halm, Kardinal).

In ADHD, there is anecdotal evidence that a combination of an amphetamine or a methylphenidate and cyproheptadine as a treatment for children suffering from ADHD can result in weight gain and excessive sleep. (Daviss 2004). In the report, a number of children were administered their ADHD drug along with 4-8 mg of cyproheptadine at night before they went to sleep. While this report suggests that there may be a benefit of using cyproheptadine in ADHD children who are suffering weight loss as a result of taking an amphetamine or methylphenidate drug, it did not identify whether the resultant weight gain was due to the child eating over a regular eating cycle, for instance, breakfast, lunch and/or dinner or due to eating over a short period of time during which the cyproheptadine affects the child's appetite, followed by hunger during the day after the effect of the effects of the cyproheptadine have worn off. Nor did the report identify whether the administration of cyproheptadine had an effect on a child's attentiveness and ability to function cognitively and socially. Additionally, the report did not analyze the impact on height. Based on the 8 hour half-life of cyproheptadine and its administration before bed in Daviss, it is not likely that children receiving the appetite stimulant had their appetites stimulated in a manner that would result in their eating food during their waking hours. Thus, though it is not reported in Daviss, it is likely that while the children gained weight, they did not see a cyproheptadine-related improvement in attentiveness during the day, particularly, while attending school.

It is an aim of the present invention to provide a pharmaceutical composition wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological syndrome is provided an amphetamine and/or a methylphenidate drug and a drug that promotes an increase in appetite. It is a further aim of the present invention to provide a pharmaceutical composition wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological syndrome is provided an amphetamine and/or methylphenidate drug and a drug that promotes an increase in appetite, while maintaining or increasing the attentiveness by the patient when compared to a patient not receiving the appetite stimulant. It is an additional aim of the present invention to provide a pharmaceutical composition wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and any other psychological and/or neurological syndrome is provided an amphetamine and/or methylphenidate drug and a drug that promotes an increase in appetite during the day that results in the maintenance or an increase in the attentiveness by the patient during the day when compared to a patient not receiving the appetite stimulant. It is a further aim of the present invention to provide a pharmaceutical composition wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological syndrome is provided an amphetamine and/or methylphenidate drug and a drug that promotes an increase in appetite during the day that results in the maintenance or an increase in the attentiveness by the patient during the day while at school, work or other situation where the patient learns, works or interacts with other people as compared to a patient not receiving the appetite stimulant. It is a further aim of the present invention to provide a pharmaceutical composition wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological syndrome is provided an amphetamine and/or methylphenidate drug and a drug that promotes an increase in appetite during the day that results in an increase in the height of the patient taking such medication versus the same patient if such medication is not taken. By following such a therapeutic regimen, a patient will suffer fewer side effects resulting from appetite loss that can reduce treatment success and compliance, while maintaining a reasonable degree of attentiveness during the day, including, without limitation maintaining a reasonable degree of cognition and social ability.

SUMMARY OF THE INVENTION

Aspects of the present specification disclose a method of treating an individual with a psychological and/or neurological disorder, including, without limitation, an attention deficit disorder, the method comprises the step of administering to an individual in need thereof a pharmaceutical composition which comprises administration of a therapeutic compound to treat the attention deficit disorder and a therapeutic compound to treat a reduction in appetite. Aspects of the present specification further disclose a pharmaceutical composition comprising a therapeutic compound for a psychological and/or neurological disorder, including, without limitation, an attention deficit disorder and a therapeutic compound for a disorder associated with a reduction in appetite, wherein the pharmaceutical composition reduces a symptom of a psychological and/or neurological disorder, including, without limitation, a disorder associated with an attention deficit disorder. Aspects of the present specification disclose treatments that can result in an increase in attentiveness, weight and/or height of the individual, thereby treating the individual.

Aspects of the present specification dislose a treatment for a neurological and/or psychological disorder, including without limitation, attention deficit disorder, and further without limitation, Attention Deficit Hyperactivity Disorder (ADHD) are treated in an individual with an amphetamine or a methylphenidate.

Aspects of the present specification disclose, without limitation, that an amphetamine or methylphenidate can be selected from the group consisting of OROS methylphenidate (Concerta), dextroamphetamine immediate/sustained release (Adderall/Adderall XR), dexmethylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

Aspects of the present specification disclose that the symptoms associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms associated with attention deficit disorder is reduced by about about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose a dose of a therapeutic compound to treat the disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day or in the range of about 0.001 mg/kg/day to about 100 mg/kg/day or in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

Aspects of the present specification disclose, without limitation, a therapeutic compound to treat the disorder is administered to an individual topical, sublingual, rectal, vaginal, trancutaneous, oral, inhaled, intranasal, subcutaneous, intravenous, enteral or parenteral. Aspects of the present specification disclos, without limitation a therapeutic compound to treat the attention deficit disorder is administered as a liquid, a solid, a semi-solid or an aerosol and a therapeutic compound is formulated as a tablet, lozenge, orally dissolved strip, capsule, syrup, oral suspension, emulsion, granule, sprinkle or pellet.

Aspects of the present specification disclose, without limitation, a therapeutic compound is a long acting, sustained release, extended release, immediate release, slow release, or controlled release therapeutic compound and the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration or is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration or is released over a period of about 1 day after administration, about 2 days after administration, about 3 days after administration, about 4 days after administration, about 5 days after administration, about 6 days after administration or about 7 days or more after administration.

Aspects of the present specification disclose, without limitation, a pharmaceutical composition that includes pharmaceutical acceptable components and the pharmaceutical acceptable components is selected from the group consisting of a salt, a surfactant, an amino acid, a stabilizer or a buffer and the salt is selected from the group consisting of citric acid, sodium chloride, potassium chloride, sodium sulfate, potassium nitrate, sodium phosphate monobasic or sodium phosphate dibasic, wherein the surfactant can be a polysorbate and the polysorbate is selected from the group consisting of Tween 20, Tween 80, F68, F88, sorbitain esters, lipids, fatty acids or fatty esters.

Aspects of the present specification disclose, without limitation, a therapeutic compound to treat a appetite reduction is an orexigenic drug and the orexigenic drug can be selected from the group of: alcohol, GHB, and other sedatives such as some benzodiazepine and nonbenzodiazepine tranquilizers and sleeping pills, anti-depressants (some SSRIs, Mianserin, etc.), 5-HT$_{2C}$ receptor antagonists/inverse agonists (e.g., mirtazapine, mianserin, olanzapine, quetiapine, risperidone, amitriptyline, imipramine, cyproheptadine, etc.), H$_1$ receptor antagonists/inverse agonists (e.g., buclizine, mirtazapine, mianserin, olanzapine, quetiapine, n-3 fatty acids, amitriptyline, chlorpheniramine maleate, etc.), D$_1$/D$_2$ receptor antagonists (e.g., haloperidol, chlorpromazine, olanzapine, risperidone, quetiapine, etc.), Marinol, Megace, Megace ES, α$_1$-adrenergic receptor antagonists (such as doxazosin, carvedilol, propanolol, colonidine), Serefam, α$_2$-adrenergic receptor agonists (e.g., clonidine, guanfacine, etc.), some beta blockers such as propanolol, natural or synthetic CB1 receptor agonists (e.g., THC or dronabinol (found in *Cannabis*), tetrahydrocannibinol, diphenydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesteronemirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-HT$_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants and cyproheptadine hydrocholoride.

Aspects of the present specification disclose symptoms associated with appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and/or the symptoms associated with appetite reduction is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% and/or the symptoms associated with reduction in the severity of appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and/or the severity associated with reduction in appetite is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% and/or the treatment for appetite reduction results in an increase in weight by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and/or the treatment for appetite reduction results in an increase in weight by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% and/or the treatment for appetite reduction results in an increase in height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and/or the treatment for appetite reduction results in an increase in weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

Aspects of the present specification disclose a treatment for appetite reduction increases the attentiveness of a patient by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and/or increases the attentiveness of a patient by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose a dose of a therapeutic compound to treat the reduction in appetite is in the range of at least 0.001 mg/kg/day, at least 0.01 mg/kg/ day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day and/or the dose of the therapeutic compound to treat reduction in appetite is in the range of about 0.001 mg/kg/day to about 100 mg/kg/day and/or the dose of the therapeutic compound to treat the reduction in appetite is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

Aspects of the present specification disclose, without limitation, that the increase in attentiveness by an individual is measured by CGI-S, wherein the CGI-S scale is from 1 to 7 and a measurement of 7 identifies an individual that is extremely ill, 6 identifies an individual that is severely ill, 5 identifies an individual that is markedly ill, 4 identifies an individual that is moderately ill, 3 identifies an individual that is mildly ill, 2 identifies an individual that is borderline ill and a measurement of 1 identifies an individual that is normal and wherein, the increase in attentiveness measured by CGI-S is by a reduction in the score by 1 or more as compared to a patient not receiving a therapeutic compound to treat a appetite reduction and wherein, a patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. Another aspect of the present specification discloses a patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose, without limitation, an increase in attentiveness by an individual is measured by CGI-I wherein, wherein the CGI-I scale is from 1 to 7 and a measurement of 7 identifies an individual that is very much worse, 6 identifies an individual that is much worse, 5 identifies an individual that is minimally worse, 4 identifies an individual that is no change, 3 identifies an individual that is minimally improved, 2 identifies an individual that is much improved and a measurement of 1 identifies an individual that is very much improved and, wherein the increase in attentiveness measured CGI-I is by a reduction in the score by 1 or more as compared to a patient not receiving a therapeutic compound to treat a reduction in appetite and further, wherein the patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% and further, wherein the patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose an increase in attentiveness by an individual is measured by, without limitation, the p academic performance rating scale, ADD evaluation scale-$3^{rd}$ edition (ADDES-3), ADHD rating scale-IV (ADHD-RS-IV), youth self report (broadband instrument), Conners parent rating scale-revised (CPRS-R), Conners teacher rating scale-revised (CTRS-R), Conners 3 self-reporting scale (Conner 3-SR; ages 8-18y), home situations questionnaire-revised, inattention/overactivity with aggression (IOWA) Conners teacher's rating scale, Swanson Nolan and Pelham IV scale (SNAP-IV), Swanson Kotkin Agler M-Flynn and Pelham (SKAMP), Vanderbilt ADHD diagnostic parent rating scale (VADPRS), Vanderbilt ADHD diagnostic teacher rating scale (VADTRS), behavior assessment system for children-$2^{nd}$ edition (BASC-2) or the Conners rating scale long version.

Aspects of the present specification disclose that a psychological and/or neurological disorder can be selected from, without limitation, the group of migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and/or tic.

Aspects of the present specification disclose a kit comprising a pharmaceutical composition to treat a disorder.

BRIEF DESCRIPTION OF THE DRAWINGS

FIG. 1 depicts improvement in attention of individuals, for example children, with increased caloric intake.

FIG. 2 depicts the impact of combination treatment on weight.

FIG. 3 depicts the impact of combination treatment on height.

FIG. 4 depicts the change in weight and height for Patient A.

FIG. 5 depicts the ADHD sensitivity for Patient A as measured by CGI-S.

FIG. 6 depicts the change in weight and height for Patient B.

FIG. 7 depicts the ADHD sensitivity for Patient B as measured by CGI-S.

FIG. 8 depicts the change in weight and height for Patient C.

FIG. 9 depicts the ADHD sensitivity for Patient C as measured by CGI-S.

FIG. 10 depicts the change in weight and height for Patient D.

FIG. 11 depicts the ADHD sensitivity for Patient D as measured by CGI-S.

FIG. 12 depicts the change in weight and height for Patient E.

FIG. 13 depicts the ADHD sensitivity for Patient E as measured by CGI-S.

FIG. 14 depicts the change in weight and height for Patient F.

FIG. 15 depicts the ADHD sensitivity for Patient F as measured by CGI-S.

FIG. 16 depicts the change in weight and height for Patient G.

FIG. 17 depicts the ADHD sensitivity for Patient G as measured by CGI-S.

FIG. 18 depicts the change in weight and height for Patient H.

FIG. 19 depicts the ADHD sensitivity for Patient H as measured by CGI-S.

FIG. 20 depicts the impact of combination treatment on the severity of ADHD as measured by CGI-S).

FIG. 21 depicts the impact of treatment on the severity of ADHD as measured by CGI-S.

FIG. 22 depicts the impact of treatment on the improvement of ADHD as measured by CGI-I.

DETAILED DESCRIPTION OF THE INVENTION

In an embodiment, the present invention discloses the treatment of a psychological and/or neurological disorder. In an embodiment, the present invention discloses the treatment of a psychological and/or neurological disorder, including without limitation, attention deficit disorder, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological disorder. In an embodiment, the present invention discloses the treatment of an attention deficit disorder, wherein the attention deficit disorder is any disorder that a patient suffers from an attention deficit. In an embodiment, the attention deficit disorder can manifest as inattentiveness, hyperactivity, impulsiveness, distractibility, disorganization, procrastination, forgetfulness, lethargy, fatigue or any other type of attention deficit disorder. In another embodiment, the attention deficit disorder is Attention Deficit Hyperactivity Disorder or ADHD.

In an embodiment, the present invention discloses the use of a pharmaceutical composition for the treatment of a psychological and/or neurological disorder. In an embodiment, the present invention discloses the use of a pharmaceutical composition to treat a psychological and/or neurological disorder, including without limitation, attention deficit disorder, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and any other psychological and/or neurological disorder.

In an embodiment, the present invention discloses the use of a pharmaceutical composition for the treatment of ADHD in a patient suffering from ADHD. In a further embodiment, a pharmaceutical composition treats ADHD in a patient suffering from ADHD and results in weight gain by a patient suffering from ADHD. In another embodiment, a pharmaceutical composition treats ADHD in a patient suffering from ADHD and results in the maintenance or an increase of the patient's attentiveness as compared to an individual not suffering from ADHD and not taking a pharmaceutical composition to treat ADHD.

Definitions: In describing and claiming the present invention, the following terminology will be used in accordance with the definitions described below.

"Pharmacologically effective amount," "physiologically effective amount," and "therapeutically effective amount" are used interchangeably herein to mean the amount of a drug or drug-combination that is needed to provide a desired level of drug in the bloodstream or in the target tissue. The precise amount will depend upon numerous factors, e.g., the particular drug or drugs employed, the components and physical characteristics of the therapeutic composition, intended patient population, individual patient considerations, and the like, and can readily be determined by one skilled in the art, based upon the information provided herein.

"Substantially" or "essentially" means nearly totally or completely, for instance, 95% or greater of some given quantity. For example, a substantial elimination of one or more symptoms or clinical indicators, means a reduction in severity of 95% or more of a symptom, as assessed by any clinically acceptable method, or an improvement of at least 95% of a given clinical indicator.

A "diminution" of one or more symptoms or clinical indicators, means a measurable reduction in the severity of such one or more symptoms, as assessed by any clinically acceptable method, or a measurable improvement of a given clinical indicator, as assessed by a skilled clinician.

The term "patient," refers to a living organism suffering from or prone to a condition that can be prevented or treated by administration of a drug or combination of drugs of the invention, and includes both humans and animals.

"Optional" or "optionally" means that the subsequently described circumstance may or may not occur, so that the description includes instances where the circumstance occurs and instances where it does not.

Aspects of the present specification disclose, in part, a pharmaceutical composition. As used herein, the term "pharmaceutical composition" is synonymous with "pharmaceutically acceptable composition" and refers to a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. Any suitable form of a therapeutic compound may be chosen. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise an R-enantiomer only, a S-enantiomer only, or a combination of both a R-enantiomer and a S-enantiomer of a therapeutic compound. A therapeutic compound disclosed herein may also be provided as prodrug or active metabolite.

The present specification discloses combinations of various therapeutic compounds that when combined produce synergistic effects to treat a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, while stimulating the same patient's appetite. The first step in current treatment of a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, is to usually treat a patient with a short acting stimulant, including, but not limited to an amphetamine and/or a methylheptadine, or introduce a long-acting stimulant, including, but not limited to a long acting version of an amphetamine or methylheptadine. If there is insufficient improvement, the dose is generally titrated up and/or a long-acting stimulant is initiated in patients not receiving a long-acting stimulant. If there are side-effects, the dosage can be titrated down or the patient can be taken off the treatment. One of the principal side-effects of amphetamine and methylphenidate usage is loss of appetite by a patient taking such medicine. This can have adverse effects on the patient, including, but not limited to, loss of weight, slower or reduced growth in height, reduced attentiveness resulting in a reduction in cognition and an inability to interact socially. To overcome this it is an aspect of the present invention to provide a method of treatment wherein a patient suffering from a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic is administered a pharmaceutical composition to treat the disorder and an appetite stimulant. Through such treatment, a patient will generally gain weight, increase in height, and/or show improved attentiveness, resulting in an increase in cognition and/or an ability to interact socially as compared to the same patient who does not take an appetite stimulant.

The present specification discloses combinations of various therapeutic compounds that when combined produce synergistic effects to treat a patient suffering from ADHD, while stimulating the same patient's appetite. The first step in current treatment of ADHD is to usually treat a patient with a short acting stimulant, including, but not limited to an amphetamine and/or a methylheptadine, or introduce a long-acting stimulant, including, but not limited to a long acting version of an amphetamine or methylheptadine. Within the first month following treatment initiation, the patient is generally re-examined for impact of the treatment on attention and treatment related side effects. If there is insufficient improvement on attention, the dose is generally titrated up and/or a long-acting stimulant is initiated in patients not receiving a long-acting stimulant. If there are side-effects, the dosage can be titrated down or the patient can be taken off the ADHD treatment. One of the principal side-effects of amphetamine and methylphenidate usage is loss of appetite by a patient taking such medicine. This can have adverse effects on the patient, including, but not limited to, loss of weight, slower or reduced growth in height, reduced attentiveness resulting in a reduction in cognition and an inability to interact socially. To overcome this it is an aspect of the present invention to provide a method of treatment wherein a patient suffering from ADHD is administered a pharmaceutical composition to treat the ADHD and an appetite stimulant. Through such treatment, a patient will generally gain weight, increase in height, and/or show improved attentiveness, resulting in an increase in cognition and/or an ability to interact socially as compared to the same patient who does not take an appetite stimulant.

In an embodiment, patient side effects are monitored to identify side effects associated with the administration of amphetamines and/or methylphenidate to a patient. In an embodiment, the side effects generally seen in patient's, include without limitation, appetite reduction, resulting in, without limitation, weight loss and/or reduced growth, including without limitation, height, loss of attentiveness, including, without limitation, reduced cognition and reduced ability to interact socially. In a further embodiment, patients found to suffer from appetite reduction are provided a pharmaceutical composition comprising a therapeutic compound to treat the patient's a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and a therapeutic compound to treat the patient's appetite reduction. In an embodiment, the therapeutic compound treats both a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and appetite reduction. In a further embodiment, a therapeutic compound treats ADHD and a different therapeutic compound treats appetite reduction. In another embodiment, one or more therapeutic compounds treat a psychological and/or neurological disorder, including, without limitation, attention deficit disorder (including, without limitation ADHD), migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and one or more different therapeutic compounds treat appetite reduction.

In an embodiment, patient side effects are monitored to identify side effects associated with the administration of amphetamines and/or methylphenidate to a patient. In an embodiment, the side effects generally seen in patient's, include without limitation, appetite reduction, resulting in, without limitation, weight loss and/or reduced growth, including without limitation, height, loss of attentiveness, including, without limitation, reduced cognition and reduced ability to interact socially. In a further embodiment, patients found to suffer from appetite reduction are provided a pharmaceutical composition comprising a therapeutic compound to treat the patient's ADHD and a therapeutic compound to treat the patient's appetite reduction. In an embodiment, the therapeutic compound treats both ADHD and appetite reduction. In a further embodiment, a therapeutic compound treats ADHD and a different therapeutic compound treats appetite reduction. In another embodiment, one or more therapeutic compounds treat ADHD and one or more different therapeutic compounds treat appetite reduction.

A pharmaceutical composition disclosed herein may comprise one or more therapeutic compounds disclosed herein. In one embodiment, a pharmaceutical composition disclosed herein may comprise only a single therapeutic compound that treats ADHD in a patient while stimulating the patient's appetite and resulting in an increase in attentiveness. In another embodiment, a pharmaceutical composition disclosed herein may comprise a plurality of therapeutic compounds wherein one or more of the therapeutic compounds treat ADHD in a patient, while one or more of the therapeutic compounds stimulates the patient's appetite and results in an increase in attentiveness. In aspects of this embodiment, a pharmaceutical composition disclosed herein comprises at least one therapeutic compound that treats ADHD in a patient while stimulating the patient's appetite resulting in an increase in attentiveness, at least two therapeutic compounds wherein one or more of the therapeutic compounds treats ADHD in a patient while one or more of the therapeutic compounds stimulates the patient's appetite resulting in an increase in attentiveness, at least three therapeutic compounds wherein one or more of the therapeutic compounds treats ADHD in a patient while one or more of the therapeutic compounds stimulates the patient's appetite resulting in an increase in attentiveness, or at least four therapeutic compounds wherein one or more of the therapeutic compounds treats ADHD in a patient while one or more of the therapeutic compounds stimulates the patient's appetite resulting in an increase in attentiveness. In other aspects of this embodiment, a pharmaceutical composition disclosed herein comprises at most two therapeutic compounds wherein one or more of the therapeutic compounds treats ADHD in a patient while one or more of the therapeutic compounds stimulates the patient's appetite resulting in an increase in attentiveness, at most three therapeutic compounds wherein one or more of the therapeutic compounds treats ADHD in a patient while one or more of the therapeutic compounds stimulates the patient's appetite resulting in an increase in attentiveness, or at most four therapeutic compounds wherein one or more of the therapeutic compounds treats ADHD in a patient while one or more of the therapeutic compounds stimulates the patient's appetite resulting in an increase in attentiveness. In yet other aspects of this embodiment, a pharmaceutical composition disclosed herein comprises one to three therapeutic compounds wherein one or more of the therapeutic compounds treats ADHD in a patient while one or more of the therapeutic compounds stimulates the patient's appetite resulting in an increase in attentiveness, two to four therapeutic compounds wherein one or more of the therapeutic compounds treats ADHD in a patient while one or more of the therapeutic compounds stimulates the patient's appetite resulting in an increase in attentiveness, two to five therapeutic compounds wherein one or more of the therapeutic compounds treats ADHD in a patient while one or more of the therapeutic compounds stimulates the patient's appetite resulting in an increase in attentiveness, three to five therapeutic compounds wherein one or more of the therapeutic compounds treats ADHD in a patient while one or more of the therapeutic compounds stimulates the patient's appetite resulting in an increase in attentiveness, or two to three therapeutic compounds wherein one or more of the therapeutic compounds treats ADHD in a patient while one or more of the therapeutic compounds stimulates the patient's appetite resulting in an increase in attentiveness. In aspects of this embodiment, a therapeutic compound that treats ADHD in a patient and/or stimulates the patient's.

In another embodiment, a pharmaceutical composition disclosed herein to treat a patient suffering from ADHD include, without limitation, amphetamines and/or methylphenidate. In an embodiment, a pharmaceutical composition disclosed herein to treat a patient suffering from ADHD include, without limitation, OROS methylphenidate (Concerta), dextroamphetamine immediate/sustained release (Adderall/Adderall XR), dexmethylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

In another embodiment, a pharmaceutical composition disclosed herein to treat a patient suffering from a psychological and/or neurological disorder, including without limitation, migraine, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic include, without limitation, amphetamines and/or methylphenidate. In an embodiment, a pharmaceutical composition disclosed herein to treat a patient suffering from a psychological and/or neurological disorder, including without limitation, migraine, anti-serotonergic side effect and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic include, without limitation, OROS methylphenidate (Concerta), dextroamphetamine immediate/sustained release (Adderall/Adderall XR), dexmethylphenidate (Focalin), Focalin XR, Metadate CD, dextroamphetamine (Dexedrine), Dexedrine Spansules, Methylin ER (Ritalin SR), methylphenidate (Ritalin), and methylphenidate CR, Ritalin, Ritalin LA, Methylin chewable, Methylin liquid, Daytrana Patch, SD-483, SPD-503, Ritalin SR, Intuniv ER, Intuniv, Methylin, Daytrana, Equasym, Dixirit, Kapvay, Metadate ER, NWP09, Dexedrine, bupropion, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

TABLE 1

| Brand Name | Generic Name** |
| --- | --- |
| Ritalin | methylphenidate |
| Ritalin SR | |
| Ritalin LA | |
| Concerta | |
| Daytrana | |
| Equasym | XL |
| Focalin | |
| Methylin | |
| Methylin | Chewable |
| Methylin Liquid | |
| Metadate CD | |
| Metadate ER | |
| NWP09 | |
| Concerta | |
| Focalin | methylphenidate |
| Focalin | XR |
| Metadate | CD |
| Ritalin | LA |
| Daytrana Patch | |
| Dexedrine | amphetamine |
| Dexedrine | Spansule |
| Dextrostat | |
| Adderall | |
| SD-483 | |
| Adderall XR | amphetamine salts |
| Strattera | atomoxetine |
| Tenex | guanfacine |
| SPD-503 | |
| Intuniv ER | |
| Intuniv | |

TABLE 1-continued

| Brand Name | | Generic Name** |
|---|---|---|
| Catapres | | clonidine |
| Catapres TTS patch | | |
| Dixirit | | |
| Kapvay | | |
| Prozac | | fluoxetine |
| Serefam | | |
| Zoloft | | sertraline |
| Luvox | | fluvoxamine |
| Paxil | | paroxetine |
| Paxil | Cr | |
| Pexeva | | |
| Celexa | | citalopram |
| Lexapro | | escitalopram |
| Tofranil | | imipramine |
| Tofranil-PM | | |
| Norpramin | | desipramine |
| Elavil | | amitryptyline |
| Pamelor | | nortriptyline |
| Sinequan | | doxepin |
| Anafranil | | clomipramine |
| Wellbutrin | | bupropion |
| Wellbutrin | SR | |
| Wellbutrin XL | | |
| Budeprion SR | | |
| Budeprion XL | | |
| Aplenzin | | |
| Effexor | | venlafaxine |
| Effexor XR | | venlafaxine |
| Remeron | | mirtazapine |
| Cymbalta | | duloxetine |
| Nardil | | phenelzine |
| Parnate | | tranylcypromine |
| Emsam patch | | selegiline |
| Haldol | | haloperidol |
| Orap | | pimozide |
| Prolixin | | fluphenazine |
| Mellaril | | thioridazine |
| Thorazine | | chlorpromazine |
| Stelazine | | trifluoperazine |
| Moban | | molindone |
| Loxitane | | loxapine |
| Risperdal | | risperidone |
| Zyprexa | | olanzapine |
| Seroquel | | quetiapine |
| Geodon | | ziprasidone |
| Abilify | | aripiprazole |
| Clozaril | | clozapine |
| Xanax | | alprazolam |
| Xanax XR | | |
| Klonopin | | clonazepam |
| Ativan | | lorazepam |
| Buspar | | buspirone |
| Ambien | | zolpidem |
| Ambien CR | | |
| Lunesta | | eszopiclone |
| Sonata | | zaleplon |
| Rozerem | | ramelteon |
| Lithium | | lithium |
| Lithobid | | |
| Eskalith | | |
| Depakote | | divalproex |
| | | valproate |
| Tegretol | | carbamazepine |
| Carbatrol | | |
| Epitol | | |
| Tegretol XR | | |
| Generics | | |
| Tegretol | | |
| Equetro | | |
| Trileptal | | oxcarbazepine |
| Lamictal | | lamotrigine |
| Topamax | | topiramate |
| Neurontin | | gabapentin |
| Lobeline | | active ingredient in the lobelia plant targets nicotinic receptors |
| Unnamed supplement | | zinc, magnesium, vitamin B6 and vitamin C |
| Cylert | | central nervous system stimulant |

TABLE 1-continued

| Brand Name | Generic Name** |
|---|---|
| CX-1739 | ampakine |
| CX-2076 | ampakine |
| CX-516 | ampakine |
| CX-546 | ampakine |
| CX-614 | ampakine |
| CX-717 | ampakine |
| ABT-894 | atomoxetine |
| Strattera | atomoxetine |
| SON0216 | bifemelane |
| Alnert | |
| Celeport | |
| OPC-34712 | Dopamine D2 receptor partial agonist |
| Procentra | dextroamphetamine |
| Vyvanse | lisdexamfetamine |
| lisdexamfetamine | |
| Various | melatonin |
| Namenda | memantine |
| Desoxyn | methamphetamine |
| Savella | milnacipran |
| Attenace | modafinil |
| Provigil | |
| ABT-894 | neuronal nicotinic receptor |
| AZD1446 | |
| AZD3480 | |
| TC-5619 | |
| ABT-089 | |
| TD-9855 | norepinephrine (and serotonin) reuptake receptor |
| LY2216684 | |
| Desipramine | norpramin |
| Pamelor | nortriptyline |
| Cyclert | pemoline |
| KP106 | prodrug of d-amphetamine |
| Nuvigil | R modafinil |
| Kuvan | sapropterin |
| SGS-742 | Selective GABA-B receptor antagonist |
| Eltoprazine | Serotonin 5-HT1A and 5-HT1B receptor agonist |
| DOV-102 | Serontoin-norepinephrine-dopamine reuptake inhibitor |
| DOV-677 | |
| Zoloft | sertraline |
| Chantix | varenicline |
| Orazinc | zinc |
| Zinc sulfate IV | |
| Zine sulfate | |

A therapeutic compound disclosed herein may be an orexigenic drug. As used herein, the term orexigenic drug refers to a class of therapeutic compounds that have the ability to stimulate a patient's appetite. Examples of suitable orexigenic drugs include, without limitation, alcohol, GHB, and other sedatives such as some benzodiazepine and non-benzodiazepine tranquilizers and sleeping pills, anti-depressants (some SSRIs, Mianserin, etc.), 5-$HT_{2C}$ receptor antagonists/inverse agonists (e.g., mirtazapine, mianserin, olanzapine, quetiapine, risperidone, amitriptyline, imipramine, cyproheptadine, etc.), $H_1$ receptor antagonists/inverse agonists (e.g., buclizine, mirtazapine, mianserin, olanzapine, quetiapine, n-3 fatty acids, amitriptyline, chlorpheniramine maleate, etc.), $D_1/D_2$ receptor antagonists (e.g., haloperidol, chlorpromazine, olanzapine, risperidone, quetiapine, etc.), Marinol, Megace, Megace ES, $\alpha_1$-adrenergic receptor antagonists (such as doxazosin, carvedilol, propanolol, colonidine), Serefam, $\alpha_2$-adrenergic receptor agonists (e.g., clonidine, guanfacine, etc.), some beta blockers such as propanolol, natural or synthetic CBI receptor agonists (e.g., THC or dronabinol (found in *Cannabis*), tetrahydrocannibinol, diphenhydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesterone.

Additional therapeutic compounds that are examples of suitable orexigenic drugs, include, without limitation, mirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-HT$_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants.

In an embodiment, the orexigenic drug is cyproheptadine hydrochloride (4-(5H-dibenzo[a,d]cyclohepten-5-ylidene)-1-methylpiperidine hydrochloride) ("Cyproheptadine"). Cyproheptadine is used as an oral monotherapy for allergy under the tradename Periactin®. Cyproheptadine reaches peak plasma levels in 1-3 hours and has a half-life of 8 hours. (Gunja, 2004). In the 1960s, it was recognized that a side-effect of Cyproheptadine was it could cause weight gain and drowsiness, which prompted the development of newer anti-histamines with better side effect profiles. In an embodiment, a pharmaceutical composition is comprised of a therapeutic compound for the treatment of ADHD and Cyproheptadine. In a further embodiment, a pharmaceutical composition is comprised of an amphetamine and/or methylphenidate and Cyproheptadine. In another embodiment, a pharmaceutical compound is comprised of either Ritalin, Focalin or Concerta and Cyproheptadine.

The present specification discloses combinations of various therapeutic compounds that when combined produce synergistic effects in treating a patient suffering from ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, while maintaining the patient's appetite and concomitant attentiveness. In addition, the present specification discloses that administration of the disclosed combinations of a therapeutic compound can be through inhalation, oral administration, intravenous ("IV"), intranasal ("IN"), sublingual, subcutaneous ("SC"), enteral, parenteral, inhaled, transcutaneous TC (for example, without limitation, through a patch placed on the skin of an individual being treated), rectal and/or vaginal.

In an embodiment, the patient is administered or takes takes a serotonin-norepinephrine-dopamine reuptake inhibitor (SNDRI), or triple reuptake inhibitor (TRI), one or more times a day. A SNDRI or TRI is a drug/ligand that simultaneously acts as a reuptake inhibitor for the monoamine neurotransmitters, serotonin (5-HT), norepinephrine (noradrenaline, NA) and dopamine (DA). In an embodiment, a SNDRI or TRI is, without limitation, EB-1020, which is catecholamine preferring TUI, is a triple reuptake inhibitor that modulates norepinephrine (NE), dopamine (DA) and serotonin (5-HT) in a ratio of 1 to 6 to 14, respectively. This preferential NE with moderate DA reuptake inhibition profile, with a small amount of 5-HT reuptake inhibition, has the potential to be an effective treatment for ADHD in adults with less risk of drug abuse liability and diversion than the stimulants used for ADHD today.

In an embodiment, the patient is administered or takes a pharmaceutical composition two or more times per day, wherein the pharmaceutical composition comprises a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant. In an embodiment, the patient is administered or takes a pharmaceutical composition once a day, wherein the pharmaceutical composition comprises a therapeutic compound for the treatment of ADHD and/or a psychological and/or neurological disorder, including without limitation, migrane, anti-serotonergic side effects narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic, and an appetite stimulant. In an embodiment, the patient is administered or takes a pharmaceutical composition in the morning or afternoon, wherein the pharmaceutical composition comprises a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant. In another embodiment, the patient is administered or takes a pharmaceutical composition in the morning, wherein the pharmaceutical composition comprises a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant. In another embodiment, the patient is administered or takes a pharmaceutical composition in the afternoon, wherein the pharmaceutical composition comprises a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant. In another embodiment, the patient does not take a pharmaceutical composition in the evening or before bed, wherein the pharmaceutical composition comprises a therapeutic compound for the treatment of ADHD and/or a psychological and/or neurological disorder, including without limitation, migrane, anti-serotonergic side effects narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant. In a further embodiment, the patient taking a pharmaceutical composition comprising a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant in the morning either maintains or increases their attentiveness when compared to a patient taking only a therapeutic compound for the treatment of ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic. In a further embodiment, the patient taking a pharmaceutical composition comprising a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD, tic and an appetite stimulant in the afternoon either maintains or increases their attentiveness when compared to a patient taking only a therapeutic compound for the treatment of ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic.

In an embodiment, attentiveness is measured using the Clinical Global Impression rating scales to measure symptom severity, treatment response and the efficacy of treatments in treatment studies of patients with mental disorders (Guy, W., 1976). In an embodiment, attentiveness is measure using the Clinical Global Impression-Severity scale ("CGI-S"). In an embodiment, CGI-S is a 7-point scale that requires the clinician to rate the severity of the patient's illness at the time of assessment, relative to the clinician's past experience with patients who have the same diagnosis. Considering total clinical experience, a patient is assessed on severity of mental illness at the time of rating 1, normal, not at all ill; 2, borderline mentally ill; 3, mildly ill; 4, moderately ill; 5, markedly ill; 6, severely ill; or 7, extremely ill. In an embodiment, attentiveness is measured using the Clinical Global Impression-Improvement scale ("CGI-I"). CGI-I is a 7 point scale that requires the clinician to assess how much the patient's illness has improved or worsened relative to a baseline state at the beginning of the intervention and rated as: 1, very much improved; 2, much improved; 3, minimally improved; 4, no change; 5, minimally worse; 6, much worse; or 7, very much worse. In an embodiment, attentiveness is measured using the Clinical Global Impression-Efficacy Index ("CGI-E"). CGI-E is a 4 point×4 point rating scale that assesses the therapeutic effect of the treatment as 1, unchanged to worse; 2, minimal; 3, moderate; 4, marked by side effects rated as none, do not significantly interfere with patient's functioning, significantly interferes with patient's functioning and outweighs therapeutic effect.

In a further embodiment, attentiveness is measured using one or more of the following ADHD screening tools and rating scales for children and adolescents, including, without limitation, academic performance rating scale, ADD evaluation scale-3$^{rd}$ edition (ADDES-3), ADHD rating scale-IV (ADHD-RS-IV), youth self report (broadband instrument), Conners parent rating scale-revised (CPRS-R), Conners teacher rating scale-revised (CTRS-R), Connoers 3 self-reporting scale (Conner 3-SR; ages 8-18y), home situations questionnaire-revised, inattention/overactivity with aggression (IOWA) Conners teacher's rating scale, Swanson Nolan and Pelham IV scale (SNAP-IV), Swanson Kotkin Agler M-Flynn and Pelham (SKAMP). Vanderbilt ADHD diagnostic parent rating scale (VADPRS), Vanderbilt ADHD diagnostic teacher rating scale (VADTRS), behavior assessment system for children-2$^{nd}$ edition (BASC-2). In an embodiment, attentiveness is measured by the Conners rating scale long version which includes without limitation, these subscales:

| | |
|---|---|
| Oppositional | Social Problems |
| Cognitive Problems/Inattention | Psychosomatic |
| Hyperactivity | Conners Global Index |
| Anxious-Shy | DSM-IV Symptom Subscale |
| Perfectionism | ADHD Index |

In one embodiment, a therapeutic compound disclosed herein is used for the treatment of ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic. In aspects of this embodiment, a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, reduces a symptom or set of symptoms, including, without limitation, the CGI-S index associated with ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression fibromyalgia and hepatitis C), lethargy, binge eating disorder, schizophrenia, sleep cycle disorder, cocaine addiction, Parkinson's Disease, combat and non-combat related PTSD and tic, reduces a symptom associated with ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In one embodiment, a therapeutic compound disclosed herein is used for the treatment of appetite reduction. In aspects of this embodiment, a therapeutic compound for the treatment of ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, reduces a symptom associated with appetite reduction by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of appetite reduction reduces a symptom associated with appetite reduction by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein for the treatment of ADHD reduces the severity of ADHD in a patient. In aspects of this embodiment, a therapeutic compound for the treatment of ADHD reduces the severity of ADHD in a patient by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of ADHD reduces the severity of ADHD in a patient by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein for the treatment of appetite reduction reduces the severity of appetite reduction in a patient. In aspects of this embodiment, a therapeutic compound for the treatment of appetite reduction reduces the severity of appetite reduction in a patient by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of appetite reduction reduces the severity of appetite reduction in a patient by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein for the treatment of appetite reduction results in an increase in weight by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of appetite reduction results in an increase in weight by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein for the treatment of appetite reduction results in an increase in height by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of appetite reduction results in an increase in height by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%

In another embodiment, a therapeutic compound disclosed herein for the treatment of appetite reduction results in an increase in weight by, e.g., at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

In another embodiment, a therapeutic compound disclosed herein for the treatment of appetite reduction increases the attentiveness of a patient being treated for ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic. In aspects of this embodiment, a therapeutic compound for the treatment of appetite reduction increases the attentiveness of a patient being treated for ADHD or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound for the treatment of appetite reduction increases the attentiveness of a patient being treated for ADHD and/or a psychological and/or neurological disorder, including without limitation, migrane, anti-serotonergic side effects and narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, without limitation, water, saline, glycine, hyaluronic acid and the like; solid carriers such as, without limitation, mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

In an embodiment, a pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, flavoring agents, coloring agents, and the like. In an embodiment, various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. In an embodiment, pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. In an embodiment, tonicity adjustors useful in a pharmaceutical composition include, without limitation, salts such as, e.g., sodium chloride, potassium chloride, mannitol or glycerin and other pharmaceutically acceptable tonicity adjustor. In an embodiment, the pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In an embodiment, a therapeutic compound disclosed herein, or a composition comprising such a therapeutic compound, may be formulated for either local or systemic delivery using topical, enteral or parenteral routes of administration. In an additional embodiment, a therapeutic compound disclosed herein may be formulated by itself in a pharmaceutical composition, or may be formulated together with one or more other therapeutic compounds disclosed herein in a single pharmaceutical composition.

In an embodiment, a therapeutic compound disclosed herein, or a composition comprising such a therapeutic compound, may be made into an inhaled formulation. In an embodiment, inhaled formulations suitable for enteral or parenteral administration include, without limitation, aerosols, dry powders. In an additional embodiment, a therapeutic compound or composition disclosed herein intended for such administration may be prepared according to any method known to the art for the manufacture of pharmaceutical compositions.

In an embodiment, such inhaled dosage forms, the therapeutic compound may be prepared for delivery as an aerosol in a liquid propellant for use in a pressurised (PDI) or other metered dose inhaler (MDI). In an embodiment, propellants suitable for use in a PDI or MDI include, without limitation, CFC-12, HFA-134a, HFA-227, HCFC-22 (difluorochloromethane), HFA-152 (difluoroethane and isobutane). In an embodiment, a therapeutic compound may also be delivered using a nebulisers or other aerosol delivery system. In an embodiment, a therapeutic compound may be prepared for delivery as a dry powder for use in a dry powder inhaler (DPI). In an embodiment, a dry powder for use in the inhalers will usually have a mass median aerodynamic diameter of less than 100 pm, 90 pm, 80 pm, 70 pm, 60 pm 50 pm, 40 pm, 30 pm, 20 pm and 10 pm. In an embodiment, microparticles having aerodynamic diameters in the range of about 5 pm to about 0.5 pm will generally be deposited in the respiratory bronchioles, whereas smaller particles, having aerodynamic diameters in the range of about 2 pm to about 0.05 pm, are likely to be deposited in the alveoli. In an embodiment, a DPI may be a passive delivery mechanism, which relies on the individual's inspiration to introduce the particles into the lungs, or an active delivery mechanism, requiring a mechanism for delivering the powder to the individual. In an embodiment, a therapeutically effective amount of a therapeutic compound disclosed herein for an inhaled formulation may be between about 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0% (w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% (w/v) or about 0.01% (w/v) to about 10.0% (w/v). In an embodiment, an inhaled formulations, a therapeutically effective amount of a therapeutic compound disclosed herein for an inhaled formulation may also be between 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0%

(w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% or about 0.01% (w/v) to about 10.0% (w/v).

In an embodiment, a therapeutic compound disclosed herein, or a composition comprising such a therapeutic compound, may be made into a solid formulation. In an embodiment, a solid formulations suitable for enteral or parenteral administration include, without limitation, capsules, tablets, pills, troches, lozenges, orally dissolving strips, powders and granules suitable for inhalation or for reconstitution into sterile injectable solutions or dispersions. In an embodiment, each of the aforementioned formulations can include, without limitation, an immediate release formulation, a slow release formulation (including without limitation, a wax matrix), beaded (including, without limitation, a double beaded wherein a bead releases immediately followed by another bead releasing at a later time), spheroidal oral drug absorption system ("SODAS"), an oral relase osmotic system ("OROS"), chewable tablet, a patch (including, without limitation, a delivery optimized thermodynamics ("DOT")), sprinkles, or a prodrug. In an embodiment, a therapeutic compound or composition disclosed herein intended for such administration may be prepared according to any method known to the art for the manufacture of pharmaceutical compositions. In an embodiment, such solid dosage forms, the therapeutic compound may be admixed without limitation (a) at least one inert customary excipient (or carrier), such as without limitation, sodium citrate or dicalcium phosphate or (b) fillers or extenders, as for example, without limitation, starch, lactose, sucrose, glucose, mannitol, isomalt, and silicic acid, (c) binders, such as, without limitation, carboxymethylcellulose, alignates, gelatin, polyvinylpyrrolidone, sucrose and acacia, (d) humectants, such as, e.g., glycerol, (e) disintegrating agents, such as,without limitation, agar-agar, calcium carbonate, corn starch, potato starch, tapioca starch, alginic acid, certain complex silicates and sodium carbonate, (f) solution retarders, such as, without limitation, paraffin, (g) absorption accelerators, such as, without limitation, quaternary ammonium compounds, (h) wetting agents, such as, without limitation, cetyl alcohol and glycerol monostearate, (i) adsorbents, such as, without limitation, kaolin and bentonite, (j) lubricants, such as, without limitation, talc, stearic acid, calcium stearate, magnesium stearate, solid polyethylene glycols, sodium lauryl sulfate or mixtures thereof, and (k) buffering agents. In an embodiment, the tablets may be uncoated or they may be coated by known techniques to delay disintegration and absorption in the gastrointestinal tract and thereby provide a sustained action over a longer period. In an additional embodiment, without limitation, a time delay material such as glyceryl monostearate or glyceryl distearate may be employed. In an embodiment, in solid formulations, a therapeutically effective amount of a therapeutic compound disclosed herein typically may be between about 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0% (w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% (w/v) or about 0.01% (w/v) to about 10.0% (w/v).

In an embodiment, a therapeutic compound disclosed herein, or a composition comprising such a therapeutic compound, may be made into a semi-solid formulation. In an embodiment, a semi-solid formulations suitable for topical administration include, without limitation, ointments, creams, salves, and gels. In an embodiment, a therapeutic compound or composition disclosed herein intended for such administration may be prepared according to any method known to the art for the manufacture of pharmaceutical compositions. In an embodiment, in semi-solid formulations, a therapeutically effective amount of a therapeutic compound disclosed herein typically may be between about 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0% (w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% (w/v) or about 0.01% (w/v) to about 10.0% (w/v). In an embodiment, in semi-solid formulations, a therapeutically effective amount of a therapeutic compound disclosed herein typically may also be between about 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0% (w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% (w/v) or about 0.01% (w/v) to about 10.0% (w/v).

In an embodiment, a therapeutic compound disclosed herein, or a composition comprising such a therapeutic compound, may be made into a liquid formulation. In an embodiment, liquid formulations suitable for enteral or parenteral administration include, without limitation, solutions, syrups, elixirs, dispersions, emulsions, and suspensions. In an embodiment, a therapeutic compound or composition disclosed herein intended for such administration may be prepared, without limitation, according to any method known to the art for the manufacture of pharmaceutical compositions. In an embodiment, in such liquid dosage forms, a therapeutic compound or composition disclosed herein may be admixed with, without limitation, (a) suitable aqueous and nonaqueous carriers, (b) diluents, (c) solvents, such as, without limitation, water, ethanol, propylene glycol, polyethyleneglycol, glycerol, vegetable oils, such as, without limitation, rapeseed oil and olive oil, and injectable organic esters such as ethyl oleate; and/or fluidity agents, such as, without limitation, surfactants or coating agents like lecithin. In the case of dispersions and suspensions, fluidity can also be controlled by maintaining a particular particle size. In an embodiment, in liquid formulations, a therapeutically effective amount of a therapeutic compound disclosed herein typically may be between about 0.0001% (w/v) to about 90% (w/v), 0.0001% (w/v) to about 80% (w/v), 0.0001% (w/v) to about 70% (w/v), 0.0001% (w/v) to about 60% (w/v), 0.0001% (w/v) to about 50% (w/v), 0.0001% (w/v) to about 40% (w/v), 0.0001% (w/v) to about 30% (w/v), 0.0001% (w/v) to about 20% (w/v), 0.0001% (w/v) to about 10% (w/v), about 0.001% (w/v) to about 90.0% (w/v), 0.001% (w/v) to about 80.0% (w/v), 0.001% (w/v) to about 70.0% (w/v), 0.001% (w/v) to about 60.0% (w/v), 0.001% (w/v) to about 0.0% (w/v), 0.001% (w/v) to about 40.0% (w/v), 0.001% (w/v) to about 30.0% (w/v), 0.001% (w/v) to about 20.0% (w/v), 0.001% (w/v) to about 10.0% (w/v) or about 0.01% (w/v) to about 90.0% (w/v), about 0.01% (w/v) to about 80.0% (w/v), about 0.01% (w/v) to about 70.0% (w/v), about 0.01% (w/v) to about 60.0% (w/v), about 0.01% (w/v) to about 50.0% (w/v), about 0.01% (w/v) to about 40.0% (w/v), about 0.01% (w/v) to about 30.0% (w/v) about 0.01% (w/v) to about 20.0% (w/v) or about 0.01% (w/v) to about 10.0% (w/v).

In an embodiment, syrups and elixirs may be formulated, without limitation, sweetening agents, for example glycerol, propylene glycol, sorbitol or sucrose. In an additional embodiment, such formulations may also contain, without limitation, a demulcent, a preservative, flavoring agents, and coloring agents.

In an embodiment, liquid suspensions may be formulated, without limitation, by suspending a therapeutic compound disclosed herein in admixture with excipients suitable for the manufacture of aqueous suspensions. In an embodiment, such excipients are suspending agents, for example, without limitation, sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example, without limitation, polyoxyethylene stearate, or condensation products of ethylene oxide with long-chain aliphatic alcohols, for example, without limitation, heptadecaethyleneoxycetanol, or condensation products of ethylene oxide with partial esters derived from fatty acids, for example, without limitation, polyoxyethylene sorbitan monooleate.

In an embodiment, oily suspensions may be formulated by suspending a therapeutic compound disclosed herein in admixture with (a) vegetable oils, such as, without limitation, almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as, without limitation, palmitic acid, stearic acid, oleic acid, linoleic acid, linolenic acid, or a combination thereof, (c) mineral oil such as, without limitation, liquid paraffin, (d) surfactants or detergents. In an embodiment, the oily suspensions may contain a thickening agent, for example beeswax, hard paraffin or cetyl alcohol. In an embodiment, sweetening agents, such as those set forth above, and flavoring agents may be added to provide a palatable oral preparation. In an embodiment, these compositions may be preserved by the addition of an antioxidant such as ascorbic acid.

In an embodiment, dispersible powders and granules suitable for preparation of an aqueous suspension by the addition of water provide the combined therapeutic compounds in admixture with a dispersing or wetting agent, suspending agent and one or more preservatives.

In an embodiment, a therapeutic compound disclosed herein may be in the form of oil-in-water emulsions. In an embodiment, the oily phase may be a vegetable oil as disclosed herein or a mineral oil as disclosed herein or mixtures thereof. In an additional embodiment, suitable emulsifying agents may be naturally occurring gums, such as, without limitation, gum acacia or gum tragacanth, naturally occurring phosphatides, for example soya bean, lecithin, and esters or partial esters derived from fatty acids and hexitol anhydrides, for example, without limitation, sorbitan monooleate and condensation products of the said partial esters with ethylene oxide, for example polyoxyethylene sorbitan monooleate.

In an embodiment, a therapeutic compound disclosed herein, or a composition comprising such a therapeutic compound, may also be incorporated into a drug delivery platform in order to achieve a controlled release profile over time. In an embodiment, such a drug delivery platform comprises a therapeutic compound disclosed herein dispersed within a polymer matrix, typically, without limitation, a biodegradable, bioerodible, and/or bioresorbable polymer matrix. In an embodiment, as used herein, the term "polymer" refers to synthetic homo- or copolymers, naturally occurring homo- or copolymers, as well as, without limitation, synthetic modifications or derivatives thereof having a linear, branched or star structure. In an embodiment, copolymers can be arranged in any form, such as, without limitation, random, block, segmented, tapered blocks, graft, or triblock. In an embodiment, polymers are generally condensation polymers. In an embodiment, polymers can be further modified to enhance their mechanical or degradation properties by introducing cross-linking agents or changing the hydrophobicity of the side residues. In an embodiment, if crosslinked, polymers are usually less than 75% crosslinked, 65% crosslinked, 55% crosslinked, 45% crosslinked, 35% crosslinked, 25% crosslinked, 15% crosslinked 5% crosslinked, usually less than 1% crosslinked.

In an embodiment, suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. In an embodiment, the polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. In an embodiment, examples of biodegradable, bioerodible, and/or bioresorbable polymers and methods useful to make a drug delivery platform are described in, e.g., Drost, without limitation, *Controlled Release Formulation*, U.S. Pat. No. 4,756,911; Smith, et. al., *Sustained Release Drug Delivery Devices*, U.S. Pat. No. 5,378,475; Wong and Kochinke, *Formulation for Controlled Release of Drugs by Combining Hyrophilic and Hydrophobic Agents*, U.S. Pat. No. 7,048,946; Hughes, et. al., *Compositions and Methods for Localized Therapy of the Eye*, U.S. Patent Publication 2005/0181017; Hughes, *Hypotensive Lipid-Containing Biodegradable Intraocular Implants and Related Methods*, U.S. Patent Publication 2005/0244464; Altman, et al., *Silk Fibroin Hydrogels and Uses Thereof*, U.S. Patent Publication 2011/0008437; each of which is incorporated by reference in its entirety.

In an embodiment, a polymer composing the matrix is a polypeptide such as, without limitation, silk fibroin, keratin, or collagen. In an additional embodiment, a polymer composing the matrix is a polysaccharide such as, without limitation, cellulose, agarose, elastin, chitosan, chitin, or a glycosaminoglycan like chondroitin sulfate, dermatan sulfate, keratan sulfate, or hyaluronic acid. In yet another embodiment, a polymer composing the matrix is a polyester such as, without limitation, D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorable kinetics of platform at implantation site, in vivo mechanical performance of platform, processing temperatures, biocompatibility of platform, and patient tolerance. Other relevant factors that, to some extent, without limitation, dictate the in vitro and in vivo behavior of the polymer include the chemical composition, spatial distribution of the constituents, the molecular weight of the polymer and the degree of crystallinity.

In an embodiment, a drug delivery platform includes both a sustained release drug delivery platform and an extended release drug delivery platform. In an embodiment, the term "sustained release" refers to the release of a therapeutic compound or compounds disclosed herein over a period of about seven days or more. In an embodiment, the term "extended release" refers to the release of a therapeutic compound or compounds disclosed herein over a period of time of less than about seven days.

In an embodiment, a sustained release drug delivery platform releases a therapeutic compound or compounds disclosed herein with substantially zero order release kinetics over a period of, without limitation, about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. In another embodiment, a sustained release drug delivery platform releases a therapeutic compound disclosed herein with substantially zero order release kinetics over a period, without limitation, at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.

In an embodiment, an ADHD therapeutic compound and/or appetite stimulant therapeutic compound or compounds is in the form of a long acting composition that includes, without limitation, extended release compositions. An embodiment includes, without limitation, an extended release capsule, tablet or other solid or a liquid formulation that provides the therapeutic compound or compunds to the patient to whom it is administered over time. The long acting composition can provide activity of an ADHD therapeutic compound and/or appetite stimulant therapeutic compound in a patient administered either or both therapeutic compounds for 4 hours, 6 hours, 8 hours, 10 hours, 12 hours, 16 hours, 20 hours, 24 hours, 28 hours, 30 hours, 32 hours, 34 hours, 36 hours, 40 hours, 48 hours, 3 days, 4 days, 5 days, 6 days, 7 days, 2 weeks, 3 weeks or 4 weeks. The long acting composition can provide activity of an ADHD therapeutic compound and/or appetite stimulant therapeutic compound or compounds in a patient administered either or both therapeutic compounds for as little as 4 hours or as long as 4 weeks, for as little as 4 hours or as long as 3 weeks, for as little as 4 hours or as long as 2 weeks, for as little as 4 hours or as long as 1 week, for as little as 4 hours or as long as 6 days, for as little as 4 hours or as long as 5 days, for as little as 4 hours or as long as 4 days, for as little as 4 hours or as long as 3 days, for as little as 4 hours or as long as 2 days, for as little as 4 hours or as long as 1 day, for as little as 4 hours or as long as 20 hours, for as little as 4 hours or as long as 16 hours, for as little as 4 hours or as long as 14 hours, for as little as 4 hours or as long as 12 hours, for as little as 4 hours or as long as 10 hours, for as little as 4 hours or as long as 8 hours, for as little as 4 hours or as long as 6 hours.

In an embodiment, a sustained release drug delivery platform releases a therapeutic compound or compounds disclosed herein with substantially first order release kinetics over a period of, without limitation, about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. In other aspects of this embodiment, a sustained release drug delivery platform releases a therapeutic compound or compounds disclosed herein with substantially first order release kinetics over a period of, without limitation, at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.

In an embodiment, a drug delivery platform releases a therapeutic compound or compounds disclosed herein with substantially zero order release kinetics over a period of, without limitation, about 1 day after administration, about 2 days after administration, about 3 days after administration, about 4 days after administration, about 5 days after administration, about 6 days after administration or about 7 days or more after administration. In an additional embodiment, a drug delivery platform releases a therapeutic compound or compounds disclosed herein with substantially zero order release kinetics over a period of, without limitation, at most 1 day after administration, at most 2 days after administration, at most 3 days after administration, at most 4 days after administration, at most 5 days after administration, at most 6 days after administration or at most 7 days or more after administration.

In an embodiment, a drug delivery platform releases a therapeutic compound or compounds disclosed herein with substantially first order release kinetics over a period of, without limitation, about 1 day after administration, about 2 days after administration, about 3 days after administration, about 4 days after administration, about 5 days after administration, about 6 days after administration or about 7 days or more after administration. In an additional embodiment, a drug delivery platform releases a therapeutic compound or compounds disclosed herein with substantially first order release kinetics over a period of, e.g., at most 1 day after administration, at most 2 days after administration, at most 3 days after administration, at most 4 days after administration, at most 5 days after administration, at most 6 days after administration or at most 7 days or more after administration.

In an embodiment of the present specification disclose, in part, treating an individual suffering from ADHD. As used herein, the term "treating," refers to reducing or eliminating in an individual a clinical symptom, set of symptoms, or clinical index for ADHD; or delaying or preventing in an individual the onset of ADHD. In an embodiment, for example, without limitation, the term "treating" can mean reducing a symptom of a condition characterized by ADHD by, without limitation, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. In an embodiment, the actual symptoms associated with ADHD are well known and can be determined by a person of ordinary skill in the art by taking into account factors well known, including, without limitation, missing details, forgetting things, frequently switch from one activity to another, having difficulty focusing, organizing, or completing tasks, losing interest after only a few minutes unless they are doing something they enjoy, having trouble with homework assignments, losing things (eg, pencils, toys, assignments), seeming to not listen when spoken to, daydreaming, become easily confused, and moving slowly. having difficulty processing information as quickly and accurately as others do, struggling to follow instructions, fidgeting and squirming in their seats, talking nonstop, running around, touching or playing with anything and everything in sight, having trouble sitting still during, without limitation, meals, school, storytime, struggling to do quiet tasks or activities, being very patient, blurting out inappropriate comments, showing emotion without restraint, acting without regard for consequences and/or interrupting conversations or other activities. In an embodiment, the actual symptoms associated with ADHD are well known and can be determined by a person of ordinary skill in the art by taking into account factors well known, including, without limitation, often does not give close attention to details or makes careless mistakes in work or other activities, often has trouble keeping attention on tasks or play activities, often does not seem to listen when spoken to directly, often does not follow instructions and fails to finish duties in the workplace, often has trouble organizing activities, often avoids, dislikes, or does not want to do things that take a lot of mental effort for a long period of time, often loses things needed for tasks and activities, is often easily distracted, is often forgetful in daily activities, often fidgets or squirms in seat, often gets up from seat when remaining seated is expected, often feels very restless, often has trouble enjoying leisure activities quietly, is often on the go or often acts as if driven by a motor, often talks impulsively, often blurts out answers before questions have been finished, often has trouble waiting one's turn and/or often interrupts or intrudes on others.

In an embodiment, the present specification disclose, in part, treating an individual suffering from appetite reduction. In an embodiment, the term "treating," refers to reducing or eliminating in an individual a clinical symptom for appetite reduction; or delaying or preventing in an individual the onset of appetite reduction. In an embodiment, for example, without limitation, the term "treating" can mean reducing a symptom of a condition characterized by appetite reduction by, without limitation, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. In an embodiment, the actual symptoms associated with appetite reduction are well known and can be determined by a person of ordinary skill in the art by taking into account factors well known, including without limitation, failure to eat a meal, failure to eat a snack, or failure to eat food.

In an embodiment, the present specification disclose, in part, treating an individual suffering from weight loss resultant from appetite reduction. In an embodiment, for example, without limitation, an increase in weight following treatment with an appetite stimulant is by, without limitation, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. In an embodiment, the present specification disclose, in part, treating an individual suffering from a reduction in height resultant from appetite reduction. In an embodiment, for example, without limitation, an increase in height following treatment with an appetite stimulant is by, without limitation, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

In an embodiment, the present specification disclose, in part, treating an individual suffering from reduced attentiveness. In an embodiment, as used herein, the term "treating," refers to reducing or eliminating in an individual a clinical symptom for reduced attentiveness; or delaying or preventing in an individual the onset of reduced attentiveness. In an embodiment, for example, without limitation, the term "treating" can mean reducing a symptom of a condition characterized by reduced attentiveness by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with reduced attentiveness are well known and can be determined by a person of ordinary skill in the art by taking into account factors well known, including, without limitation, lack of mental cognition, lack of ability to interact socially.

In an embodiment, a pharmaceutical composition disclosed herein may comprise a therapeutic compound in a therapeutically effective amount. In an embodiment, as used herein, without limitation, the term "effective amount" is synonymous with "therapeutically effective amount", "effective dose", or "therapeutically effective dose." In an embodiment, the effectiveness of a therapeutic compound disclosed herein to treat ADHD, treat appetite reduction and/or treat a reduction in attentiveness can be determined, without limitation, by observing an improvement in an individual based upon one or more clinical symptoms, and/or physiological indicators associated with the ADHD, appetite reduction and/or reduction in attentiveness. In an embodiment, an improvement in the symptoms associated with ADHD, appetite reduction and/or reduced attentiveness can be indicated by a reduced need for a concurrent therapy.

In an embodiment, the appropriate effective amount of a therapeutic compound disclosed herein to be administered to an individual for the treatment of ADHD and appetite reduction can be determined by a person of ordinary skill in the art by taking into account factors that are well known. In an additional embodiment, where repeated administration of a therapeutic compound is used, an effective amount of a therapeutic compound will further depend upon factors, including, without limitation, the frequency of administration, the half-life of the therapeutic compound, or any combination thereof. In an embodiment, it is known by a person of ordinary skill in the art that an effective amount of a therapeutic compound disclosed herein can be extrapolated from in vitro assays and in vivo administration studies using animal models prior to administration to humans.

Wide variations in the necessary effective amount are to be expected in view of the differing efficiencies of the various routes of administration. For instance, without limitation, oral administration of a therapeutic compound disclosed herein generally would be expected to require higher dosage levels than administration by inhalation. Similarly, without limitation, systemic administration of a therapeutic compound disclosed herein would be expected to require higher dosage levels than a local administration. Variations in these dosage levels, without limitation, can be adjusted using standard empirical routines of optimization, which are well-known to a person of ordinary skill in the art. The precise therapeutically effective dosage levels and patterns are preferably determined, without limitation, by the attending physician in consideration of the above-identified factors. One skilled in the art will recognize that the condition of the individual can be monitored, without limitation, throughout the course of therapy and that the effective amount of a therapeutic compound disclosed herein that is administered can be adjusted accordingly.

In an embodiment, a therapeutically effective amount of a therapeutic compound disclosed herein reduces a symptom associated with ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, without limitation, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In an additional embodiment, a therapeutically effective amount of a therapeutic compound disclosed herein reduces a symptom associated with ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, without limitation, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In a further embodiment, a therapeutically effective amount of a therapeutic compound disclosed herein reduces a symptom associated with a ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, by, without limitation, about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In an embodiment, a therapeutically effective amount of a therapeutic compound disclosed herein reduces a symptom associated with appetite reduction by, without limitation, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In an additional embodiment, a therapeutically effective amount of a therapeutic compound disclosed herein reduces a symptom associated with appetite reduction by, without limitation, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In a further embodiment, a therapeutically effective amount of a therapeutic compound disclosed herein reduces a symptom associated with a appetite reduction by, without limitation, about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In an embodiment, a therapeutically effective amount of a therapeutic compound disclosed herein reduces a symptom associated with loss of attentiveness by, without limitation, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with loss of attentiveness by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In an additional embodiment, a therapeutically effective amount of a therapeutic compound disclosed herein reduces a symptom associated with a loss of attentiveness by, without limitation, about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In an embodiment, a therapeutically effective amount of a therapeutic compound disclosed herein increases the weight or height of an individual is determined by an increase in the individual's weight or height velocity as compared to an individual nor receiving a therapeutic compound for appetite reduction. In an embodiment, weight and/or height velocity can be calculated by taking measurements of height and/or weight of an individual over a period of time and measuring an increase or decrease in an individual's height and/or weight over the period of time. In an embodiment, weight velocity is calculated by taking three time points, time 0 upon initiation of medication to treat ADHD, time 1 addition of an appetite stimulant, time 2 the last data point after initiation of combination treatment. In an embodiment, a formula to calculate weight and height velocity for stimulant alone is (weightT1−weight T0)/days from Time 0 to time 1. In an embodiment, a formula to calculate weight velocity for combination treatment is (weightT2−weight T1)/days from time 1 to time 2. In an embodiment, to evaluate whether weight velocity increased after addition of an appetite stimulant, the weight velocity of time 0 to time 1 is compared to the weight velocity from time 1 to time 2. In an embodiment, height velocity is calculated by taking three time points, time 0 upon initiation of medication to treat ADHD, time 1 addition of an appetite stimulant, time 2 the last data point after initiation of combination treatment. The formula to calculate height velocity for stimulant alone is (weightT1−weight T0)/days from Time 0 to time 1. The formula to calculate height velocity for combination treatment is (weightT2−weight T1)/days from time 1 to time 2. In an embodiment, to evaluate whether height velocity increased after addition of an appetite stimulant, the height velocity of time 0 to time 1 is compared to the height velocity from time 1 to time 2.

In an embodiment, a therapeutically effective amount of a therapeutic compound disclosed herein generally is in the range of about 0.001 mg/kg/day to about 100 mg/kg/day. In an additional embodiment, an effective amount of a therapeutic compound disclosed herein may be, without limitation, at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In a further embodiment, an effective amount of a therapeutic compound disclosed herein may be in the range of, without limitation, about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In a further embodiment, an effective amount of a therapeutic compound disclosed herein may be in the range of, without limitation, about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In a further embodiment, an effective amount of a therapeutic compound disclosed herein may be in the range of, without limitation, about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In an embodiment, an effective amount of a therapeutic compound disclosed herein may be in the range of, without limitation, about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In an additional embodiment, an effective amount of a therapeutic compound disclosed herein may be in the range of, without limitation, about 5 mg/kg/ day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In an embodiment, a therapeutically effective amount of a therapeutic compound disclosed herein generally is in the range of about 1 mg/day to about 3,000 mg/day. In an additional embodiment, an effective amount of a therapeutic compound disclosed herein may be, without limitation, at least 50 mg/day, at least 100 mg/day, at least 150 mg/day, at least 200 mg/day, at least 250 mg/day, at least 300 mg/day, at least 350 mg/day, at least 400 mg/day, at least 450 mg/day, at least 500 mg/day, at least 550 mg/day, at least 600 mg/day, at least 650 mg/day, at least 700 mg/day, at least 750 mg/day, at least 800 mg/day, at least 850 mg/day, at least 900 mg/day, at least 950 mg/day, at least 1,000 mg/day, at least 1,50 mg/day, at least 1,100 mg/day, at least 1,150 mg/day, at least 1,200 mg/day, at least 1,250 mg/day, at least 1,300 mg/day, at least 1,350 mg/day, at least 1,400 mg/day, at least 1,450 mg/day, at least 1,500 mg/day, at least 1,600 mg/day, at least 1,700 mg/day, at least 1,800 mg/day, at least 1,900 mg/day, at least 2,000 mg/day, at least 2,100 mg/day, at least 2,200 mg/day, at least 2,300 mg/day, at least 2,400 mg/day, at least 2,500 mg/day, at least 2,600 mg/day, at least 2,700 mg/day, at least 2,800 mg/day, at least 2,900 mg/day, or at least 3,000 mg/day. In an additional embodiment, an effective amount of a therapeutic compound disclosed herein may be between, without limitation, about 50 mg/day to about 1,000 mg/day, about 100 mg/day to about 1,000 mg/day, about 150 mg/day to about 1,000 mg/day, about 200 mg/day to about 1,000 mg/day, about 250 mg/day to about 1,000 mg/day, about 300 mg/day to about 1,000 mg/day, about 350 mg/day to about 1,000 mg/day, about 400 mg/day to about 1,000 mg/day, about 450 mg/day to about 1,000 mg/day, about 500 mg/day to about 1,000 mg/day, about 50 mg/day to about 1,500 mg/day, about 100 mg/day to about 1,500 mg/day, about 150 mg/day to about 1,500 mg/day, about 200 mg/day to about 1,500 mg/day, about 250 mg/day to about 1,500 mg/day, about 300 mg/day to about 1,500 mg/day, about 350 mg/day to about 1,500 mg/day, about 400 mg/day to about 1,500 mg/day, about 450 mg/day to about 1,500 mg/day, about 500 mg/day to about 1,500 mg/day, about 1,000 mg/day to about 3,000 mg/day, about 1,100 mg/day to about 3,000 mg/day, about 1,200 mg/day to about 3,000 mg/day, about 1,3000 mg/day to about 3,000 mg/day, about 1,400 mg/day to about 3,000 mg/day, about 1,500 mg/day to about 3,000 mg/day, about 1,600 mg/day to about 3,000 mg/day, about 1,700 mg/day to about 3,000 mg/day, about 1,800 mg/day to about 3,000 mg/day, about 1,900 mg/day to about 3,000 mg/day, or about 2,000 mg/day to about 3,000 mg/day.

In an embodiment, a therapeutically effective amount of an amphetamine, methylphenidate or cyproheptadine disclosed herein generally is in the range of about 0.001 mg/kg/day to about 100 mg/kg/day. In an additional embodiment, an effective amount of an amphetamine disclosed herein may be, without limitation, at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In a further embodiment, an effective amount of an amphetamine, methylphenidate or cyproheptadine disclosed herein may be in the range of, without limitation, about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In a further embodiment, an effective amount of an amphetamine, methylphenidate or cyproheptadine disclosed herein may be in the range of, without limitation, about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In a further embodiment, an effective amount of an amphetamine, methylphenidate or cyproheptadine disclosed herein may be in the range of, without limitation, about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In an embodiment, an effective amount of an amphetamine, methylphenidate or cyproheptadine disclosed herein may be in the range of, without limitation, about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In an additional embodiment, an effective amount of an amphetamine, methylphenidate or cyproheptadine disclosed herein may be in the range of, without limitation, about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In an embodiment, dosing can be single dosage or cumulative (serial dosing), and can be readily determined by one skilled in the art. In an additional embodiment, treatment of ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, may comprise a one-time administration of an effective dose of a pharmaceutical composition disclosed herein. In a further embodiment, treatment of ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and tic, may comprise multiple administrations of an effective dose of a pharmaceutical composition carried out over a range of time periods, such as, e.g., once daily, twice daily, trice daily, once every few days, or once weekly. In an embodiment, the timing of administration can vary from individual to individual, depending upon such factors as the severity of an individual's symptoms. For example, in an embodiment, without limitation, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In an embodiment, various routes of administration can be useful for administering a therapeutic compound disclosed herein, according to a method of treating a coughing condition disclosed herein. In an embodiment, a pharmaceutical composition may be administered to an individual by any of a variety of means depending, without limitation, on the type of condition to be treated, the location of the condition to be treated, the specific therapeutic compound or composition used, or other compound to be included in the composition, and the history, risk factors and symptoms of the individual. As such, without limitation, topical, sublingual, rectal, vaginal, trancutaneious, oral, inhaled, intranasal, subcutaneous, intravenous, enteral or parenteral routes of administration may be suitable for of treating ADHD and/or a psychological and/or neurological disorder, including without limitation, migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and ticdisclosed herein and such routes include, without limitation, both local and systemic delivery of a therapeutic compound or composition disclosed herein. In an embodiment, compositions comprising either a single therapeutic compound disclosed herein, or two or more therapeutic compounds disclosed herein are intended for inhaled, enteral, parenteral, topical, intranasal, sublingual, subcutaneous, intravenous, rectal, transcutaneous (for example, without limitation, through a patch placed on the skin of an individual being treated) and/or vaginal use may be prepared according to any method known to the art for the manufacture of pharmaceutical compositions.

In an embodiment, the therapeutic compound includes, without limitation, an extended release, sustained release or long acting form. In an additional embodiment, the extended release, sustained release or long acting form of a therapeutic compound is linked, without limitation, to a polymer, including, without limitation, to a water soluble polymer. In an embodiment, a water-soluble polymer is selected, without limitation, from the group consisting of poly(alkylene oxide), poly(vinyl pyrrolidone), poly(vinyl alcohol), polyoxazoline, poly(acryloylmorpholine), and combinations thereof. In an additional embodiment, the water soluble polymer is a poly(alkylene oxide) such as, without limitation, a poly(ethylene glycol) derivative. In an embodiment, a water soluble polymer has, without limitation, a nominal average molecular weight in the range from about 2,000 Daltons to about 150,000 Daltons, from about 2,000 Daltons to about 125,000 Daltons, from about 2,000 Daltons to about 100,000 Daltons, from about 2,000 Daltons to about 75,000 Daltons, from about 2,000 Daltons to about 50,000 Daltons, from about 2,000 Daltons to about 25,000 Daltons, from about 5,000 Daltons to about 150,000 Daltons, from about 5,000 Daltons to about 100,000 Daltons, from about 5,000 Daltons to about 75,000 Daltons, from about 5,000 Daltons to about 50,000 Daltons, from about 5,000 Daltons to about 25,000 Daltons, from about 10,000 Daltons to about 100,000 Daltons, from about 10,000 Daltons to about 75,000 Daltons, from about 10,000 Daltons to about 50,000 Daltons, from about 10,000 Daltons to about 25,000 Daltons. In an embodiment, a water soluble polymer has, without limitation, a nominal average molecular weight of at least 150,000 Daltons, at least 125,000 Daltons, at least 100,000 Daltons, at least 75,000 Daltons, at least 50,000 Daltons, at least 25,000 Daltons. In an additional embodiment, the extended release, sustained release or long acting form of a therapeutic compound is linked, without limitation, to a polymer, including, without limitation, to a water soluble polymer through, without limitation, a stable linker or a releasable linker.

In an embodiment, the pharmaceutical compositions of the invention, including, without limitation a therapeutic compound, may further comprise one or more pharmaceutically acceptable excipients to provide a pharmaceutical composition. In an additional embodiment, excipients include, without limitation, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

In an embodiment, a pharmaceutical composition of the invention, including, without limitation a therapeutic compound, may include one or more carbohydrates such as a sugar, a derivatized sugar such as an alditol, aldonic acid, an esterified sugar, and/or a sugar polymer. Specific carbohydrate excipients include, for example, without limitation: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

In an embodiment, pharmaceutical compositions of the invention, including, without limitation, a therapeutic compound, are potato and corn-based starches such as sodium starch glycolate and directly compressible modified starch.

In an embodiment, further representative excipients include, without limitation, inorganic salt or buffers such as citric acid, sodium chloride, potassium chloride, sodium sulfate, potassium nitrate, sodium phosphate monobasic, sodium phosphate dibasic, and combinations thereof.

In an embodiment, the pharmaceutical composition, including, without limitation, a therapeutic compound, may also include, without limitation, an antimicrobial agent, without limitation, for preventing or deterring microbial growth. In an embodiment, non-limiting examples of antimicrobial agents suitable for the present invention include, without limitation, benzalkonium chloride, benzethonium chloride, benzyl alcohol, cetylpyridinium chloride, chlorobutanol, phenol, phenylethyl alcohol, phenylmercuric nitrate, thimersol, and combinations thereof.

In an embodiment, a pharmaceutical composition of the invention, including, without limitation a therapeutic compound may also contain one or more antioxidants. In an additional embodiment, antioxidants are used to prevent oxidation, thereby preventing the deterioration of the drug(s) or other components of the preparation. In a further embodiment, suitable antioxidants for use in the present invention include, for example, without limitation, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

In an embodiment, additional excipients include, without limitation, surfactants such as polysorbates without limitation, "Tween 20" and "Tween 80," and pluronics such as, without limitation, F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

In an embodiment, a pharmaceutical composition of the invention, including, without limitation a therapeutic compound, may optionally include one or more acids or bases. In an embodiment, non-limiting examples of acids that can be used include, without limitation, those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. In an embodiment, suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

In an embodiment, the amount of any individual excipient in the composition will vary depending on the role of the excipient, the dosage requirements of the active agent components, and particular needs of the composition. In an embodiment, the optimal amount of any individual excipient is determined through routine experimentation, without limitation, by preparing compositions containing varying amounts of the excipient (ranging from low to high), examining the stability and other parameters, and then determining the range at which optimal performance is attained with no significant adverse effects.

In an embodiment, the excipient will be present in the composition in an amount of, without limitation, about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19.sup.th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

In an embodiment, the compositions encompass all types of formulations and in particular those that are suited for oral administration, without limitation, tablets, lozenges, orally dissolved strips, capsules, syrups, oral suspensions, emulsions, granules, sprinkles and pellets. In an additional embodiment, formulations include, without limitation, aerosols, transdermal patches, gels, creams, ointments, suppositories, powders or lyophilates that can be reconstituted, as well as liquids, such as for use in an oral or parenteral product. In an embodiment, suitable diluents for reconstituting solid compositions, without limitation, prior to injection, include bacteriostatic water for injection, dextrose 5% in water, phosphate-buffered saline, Ringer's solution, saline, sterile water, deionized water, and combinations thereof. In an additional embodiment, liquid pharmaceutical compositions, solutions and suspensions are envisioned.

In an embodiment, for oral, rectal, vaginal, sublingual and/or intranasal delivery formulations, tablets can be made by compression or molding, optionally with one or more accessory ingredients or additives. In an embodiment, compressed tablets are prepared, for example, by compressing in a suitable tabletting machine, the active ingredients in a free-flowing form such as a powder or granules, optionally mixed with a binder (for example, without limitation, povidone, gelatin, hydroxypropylmethyl cellulose), lubricant, inert diluent, preservative, disintegrant (for example, without limitation, sodium starch glycolate, cross-linked povidone, cross-linked sodium carboxymethyl cellulose) and/or surface-active or dispersing agent.

In an embodiment, molded tablets are made, for example, without limitation, by molding in a suitable tabletting machine, a mixture of powdered compounds moistened with an inert liquid diluent. In an embodiment, the tablets may optionally be coated or scored, and may be formulated so as to provide slow or controlled release of the active ingredients, using, for example, without limitation, hydroxypropylmethyl cellulose in varying proportions to provide the desired release profile. In an embodiment, tablets may optionally be provided with a coating, without limitation, such as a thin film, sugar coating, or an enteric coating to provide release in parts of the gut other than the stomach. In an embodiment, processes, equipment, and toll manufacturers for tablet and capsule making are well-known in the art.

In an embodiment, capsule formulations may utilize, without limitation, either hard or soft capsules, including, without limitation, gelatin capsules or vegetarian capsules such as those made out of hydroxymethylpropylcellulose (HMPC). In an embodiment, a type of capsule is a gelatin capsule. In an embodiment, capsules may be filled using a capsule filling machine such as, without limitation, those available from commercial suppliers such as Miranda International or employing capsule manufacturing techniques well-known in the industry, as described in detail in Pharmaceutical Capules, 2.sup.nd Ed., F. Podczeck and B. Jones, 2004. In an embodiment, capsule formulations may be prepared, without limitation, using a toll manufacturing center such as the Chao Center for Industrial Pharmacy & Contract Manufacturing, located at Purdue Research Park.

In an embodiment, formulations for topical administration in the mouth include lozenges comprising, without limitation, the active ingredients, generally in a flavored base such as sucrose and acacia or tragacanth and pastilles comprising the active ingredients in an inert base such as gelatin and glycerin or sucrose and acacia.

In an embodiment, a pharmaceutical composition for topical administration may also be formulated, without limitation, as an ointment, cream, suspension, lotion, powder, solution, paste, gel, spray, aerosol or oil. In an embodiment, the formulation may be, without limitation, in the form of a patch (e.g., a transdermal patch) or a dressing such as a bandage or adhesive plaster impregnated with active ingredients and optionally one or more excipients or diluents. In an embodiment, topical formulations may additionally, without limitation, include a compound that enhances absorption or penetration of the ingredients through the skin or other affected areas, such as dimethylsulfoxidem bisabolol, oleic acid, isopropyl myristate, and D-limonene, to name a few.

In an embodiment, for emulsions, the oily phase is constituted, without limitation, from known ingredients in a known manner. In an embodiment, while this phase may comprise merely an emulsifier (otherwise known as an emulgent), it desirably comprises, without limitation, a mixture of at least one emulsifier with a fat and/or an oil. In an embodiment, a hydrophilic emulsifier is included, without limitation, together with a lipophilic emulsifier that acts as a stabilizer. In an embodiment, the emulsifier(s) with or without stabilizer(s) make up, without limitation, the so-called emulsifying wax, and the wax together with the oil and/or fat make up, without limitation, the so-called emulsifying ointment base which forms the oily dispersed phase of cream formulations. In an embodiment, illustrative emulgents and emulsion stabilizers include, without limitation, Tween 60, Span 80, cetostearyl alcohol, myristyl alcohol, glyceryl monostearate and sodium lauryl sulfate.

In an embodiment, formulations for rectal administration are typically, without limitation, in the form of a suppository with a suitable base comprising, for example, cocoa butter or a salicylate.

In an embodiment, formulations suitable for vaginal administration generally take the form, without limitation, of a suppository, tampon, cream, gel, paste, foam or spray.

In an embodiment, formulations suitable for nasal administration, wherein the carrier is a solid, include, without limitation, a coarse powder having a particle size, for example, without limitation, in the range of about 20 to about 500 microns. In an additional embodiment, such a formulation is typically administered, without limitation, by rapid inhalation through the nasal passage, for example, without limitation, from a container of the powder held in proximity to the nose. In an embodiment, a formulation for nasal delivery may be, without limitation, in the form of a liquid, e.g., a nasal spray or nasal drops.

In an embodiment, aerosolizable formulations for inhalation may be, without limitation, in dry powder form (e.g., suitable for administration by a dry powder inhaler), or, alternatively, may be in liquid form, e.g., for use in a nebulizer. In an embodiment, nebulizers for delivering an aerosolized solution include, without limitation, the AERx™ (Aradigm), the Ultravent® (Mallinkrodt), and the Acorn II® (Marquest Medical Products). In an embodiment, a composition of the invention may also, without limitation, be delivered using a pressurized, metered dose inhaler (MDI), e.g., the Ventolin® metered dose inhaler, containing a solution or suspension of a combination of drugs as described herein in a pharmaceutically inert liquid propellant, for example, without limitation, a chlorofluorocarbon or fluorocarbon.

In an embodiment, formulations suitable for parenteral administration include, without limitation, aqueous and non-aqueous isotonic sterile solutions suitable for injection, as well as aqueous and non-aqueous sterile suspensions.

In an embodiment, parenteral formulations of the invention are optionally contained, without limitation, in unit-dose or multi-dose sealed containers, for example, without limitation, ampoules and vials, and may be stored in a freeze-dried (lyophilized) condition requiring only the addition of the sterile liquid carrier, for example, water for injections, immediately prior to use. In an embodiment, extemporaneous injection solutions and suspensions may be prepared, without limitation, from sterile powders, granules and tablets of the types previously described.

In an embodiment, a formulation of the invention may also be, without limitation, a sustained release formulation, such that each of the drug components is released or absorbed slowly over time, when compared to a non-sustained release formulation. In an embodiment, sustained release formulations may, without limitation, employ prodrug forms of the active agent, delayed-release drug delivery systems such as, without limitation, liposomes or polymer matrices, hydrogels, or covalent attachment of a polymer such as polyethylene glycol to the active agent.

In an embodiment, in addition to the ingredients particularly mentioned above, the formulations of the invention may optionally include, without limitation, other agents conventional in the pharmaceutical arts and particular type of formulation being employed, for example, without limitation, for oral administration forms, the composition for oral administration may also include additional agents as sweeteners, thickeners or flavoring agents.

In an embodiment, the compositions of the present invention may also be prepared, without limitation, in a form suitable for veterinary applications.

In an embodiment, the anti-arthritic compositions described herein are, without limitation, in unit dosage form, meaning a quantity of a combination of drugs of the invention, appropriate for a single dose, or multiple doses, in one or more premeasured or pre-packaged forms. In an additional embodiment, a type of solid dosage form, without limitation, is a capsule containing each of an antiviral compound, a broad-spectrum antibiotic, and an antiprotozoal compound, or any two of the foregoing. In an embodiment, dosage forms and modes of administration are discussed in greater detail in the sections that follow.

In an embodiment, provided herein is a kit or package containing, without limitation, at least one combination composition of the invention, accompanied by instructions for use.

In an embodiment, in instances in which each of the drugs themselves are administered, without limitation, as individual or separate dosage forms (e.g., capsules or tablets), the kit comprises, without limitation, each of the drugs making up the composition of the invention, along with instructions for use. In an additional embodiment, the drug components, without limitation, may be packaged in any manner suitable for administration, so long as the packaging, when considered along with the instructions for administration, without limitation, clearly indicates the manner in which each of the drug components is to be administered. In a further embodiment, each of the drug components of the combination may, without limitation, be combined into a single administrable dosage form such as a capsule.

Various embodiments according to the above may be readily envisioned, and would of course depend upon the particular combination of drugs employed for treatment, their corresponding dosage forms, recommended dosages, intended patient population, and the like. In an embodiment, the packaging may be in any form commonly employed for the packaging of pharmaceuticals, such as medication punch cards or blisters, and may utilize any of a number of features such as different colors, wrapping, tamper-resistant packaging, blister paks, dessicants, and the like.

EXAMPLES

Example 1: Treatment of a Patient Suffering from ADHD with and without an Appetite Stimulant A patient suffering from ADHD is prescribed and administered an amphetamine to treat ADHD. The patient takes the amphetamine once a day in the morning or afternoon. Following administration, the patient suffers a loss of appetite and reduces their caloric intake. As a result, the glucose level measured in the blood drops as shown in FIG. 1 and the patient suffers a lack of attentiveness as measured by CGI-S and CGI-I. When the patient is administered an amphetamine and Cyroheptadine once a day either in the morning or afternoon, the patient's appetite resumes and the patient increases their caloric intake. As a result, the glucose level measured in the blood increases as shown in FIG. 1 and the patient's attentiveness recovers as measured by CGI-S and CGI-I. By taking the appetite stimulant during the time when the patient was awake, the patient increased their caloric intake during times when the patient needed to maintain their attentiveness in order to have reasonable cognition and/or social behaviour.

Example 2: Once a Day Periactin

Case study: A six-year and ten month old girl was presented by her parents for symptoms of attention deficit hyperactivity disorder. Her size at evaluation was 4'1¾" and 50 lbs, corresponding to the $81^{st}$ and $50^{th}$ percentiles when compared to girls her age. She responded well to treatment with various forms of methylphenidate, utilizing at various times both short-acting formulations, as well as a trial on a transdermal patch. A side-effect suffered by the girl was suppression of appetite and a lack of significant weight gain. At three months following the initiation of treatment for ADHD, the girl was 4'2⅞" and 50½ lbs, corresponding to the $85^{th}$ and $34^{rd}$ percentiles when compared to girls her age. At one year, she was 4'4⅜" and 53 lbs, corresponding to the $84^{th}$ and $36^{th}$ percentiles when compared to girls her age. At two years she was 4'5¾" and 54 lbs, corresponding to the $72^{nd}$ and $17^{th}$ percentiles when compared to girls her age. At four years of treatment she was 4'7⅜" and 59 lbs, corresponding to $70^{th}$ and $14^{th}$ percentiles when compared to girls her age. At five years of treatment she was 4'9⅞" and 64½ lbs, corresponding to $59^{th}$ and $7^{th}$ percentiles when compared to girls her age.

The girl was then prescribed Periactin at a dosage of 2 mg b.i.d. to attempt to stimulate appetite. The dose was taken in the morning and then in the afternoon. After one year she was 4'11½" and 72½ lbs, corresponding to $33^{rd}$ and $5^{th}$ percentiles when compared to girls her age. The girl was then prescribed Periactin at a dose of 4 mg b.i.d. After two months on this dose, she was 5'¼" and 76 lbs, corresponding to $37^{th}$ and $8^{th}$ percentiles when compared to girls her age. At 8 months on this dose, she was 5'½" and 80 lbs, corresponding to $41^{st}$ and $8^{th}$ percentiles when compared to girls her age. At one year on this dose, she was 5'2¾" and 89½ lbs, corresponding to $51^{st}$ and $17^{th}$ percentiles when compared to girls her age. At 18 months on this dose, she was 5'3⅝" and 99½ lbs, corresponding to $56^{th}$ and $30^{th}$ percentiles when compared to girls her age. Additionally, the attentiveness of the girl increase following the prescription of Periactin as she increased her food intake during the day.

Example 3: Treatment of Patients Suffering from ADHD and Reduction in Appetite Eight patients, identified as patients A-H, that came in suffering from ADHD were treated for ADHD. Each patient was prescribed an amphetamine or methylphenidate to treat ADHD and each patient following such treatment suffered a reduction in appetite and failed to gain sufficient weight. Each patient was then prescribed an appetite simulant to be taken along with the amphetamine or methylphenidate. The patients' weight, height and attentiveness were then followed during the course of treatment.

The age range of the patients was from 6-15 years of age, with a mean age at the start of treatment for ADHD of 8.4 years of age. The mean age at the start of the combination treatment wherein the patient was administered an amphetamine or methylphenidate and an appetite stimulant was 10.3 years of age. The mean treatment period for the eight patients was 1,108 days with a mean of 2.55 ADHD medication changes during the treatment period. Attentiveness in the eight patients was measured using CGI-S and CGI-I. Patients weight and height velocity were measured to identify a difference in weight and height gain prior to and after addition of an appetite stimulant to the treatment for ADHD. Weight velocity was calculated by taking three time points, time 0 upon initiation of medication to treat ADHD, time 1 addition of an appetite stimulant, time 2 the last data point after initiation of combination treatment. The formula to calculate weight velocity for stimulant alone is (weightT1−weight T0)/days from Time 0 to time 1. The formula to calculate weight velocity for combination treatment is (weightT2−weight T1)/days from time 1 to time 2.

Following initiation of treatment for ADHD, but prior to the initiation of combination treatment, the mean loss by a patient was 41 percentile points in the weight curve as compared to the expected weight gain over the same time period by the patient if not provided the ADHD treatment. The mean loss was 34 percentile points in the height curve as compared to the expected growth in height over the same time period by the patient if not provided the ADHD treatment. For the eight patients, the mean weight velocity with the ADHD treatment only was 3.455 g/day. This compares to a mean weight velocity of 13.972 g/day in patients administered the combination treatment as shown in FIG. 2. This corresponded to a 304% increase in the weight gain by the patients following administration of the combination treatment comprising an amphetamine or methylphenidate and an appetite stimulant, Cyroheptadine. Similarly, the eight patients saw an increase in their height velocity following initiation of the combination treatment. The mean height velocity of the eight patients when administered only a treatment for ADHD was 0.091 cm/day. This compared to a mean height velocity of 0.180 cm/day in patients following administration of the combination treatment. This corresponds to a 98% increase in the rate of height addition for patients following initiation of the combination treatment. In addition, the eight patients saw a mean increase of 17.5 percentile points in their weight curve following the initiation of combination treatment versus the aforementioned loss of 41 percentile points for administration of the ADHD treatment without an appetite stimulant. Concordantly, the eight patients saw a mean increase of 16.7 percentile points in their height curve following the initiation of combination treatment versus the aforementioned loss of 34 percentile points for administration of the ADHD treatment without an appetite stimulant.

The mean number of days to the first follow-up with a patient following initiation of the combination treatment was 73 days. At this first follow-up, the mean weight velocity of the patient was 27.3 g/day. This resulted in a 790% increase in weight addition with combination treatment at the first follow-up. Further, all eight patients on the combination treatment were able to maintain their highest weight as of the last follow-up date.

Example 4: Patient A

Patient A was a male who was 6 years and approximately 3 months when treatment for ADHD was initiated. Patient A was administered 18 mg of Concerts. Initially, following a short loss in weight, patient A began to gain weight, but at about day 371 after initiation of treatment, Patient A began to lose weight again as shown in FIG. 4. The loss of weight continued until on day 661 Patient A was prescribed and began to take 4 mg. b.i.d. of Periactin. Following initiation of the combination treatment, Patient A began to gain weight and the increase in height began to accelerate as shown in FIG. 4. Additionally, following initiation of the combination treatment, Patient A also saw a decrease in his CGI-S score, going from a score of 4 that had been constant for almost 400 days to a score of 3 as shown in FIG. 5.

Example 5: Patient B

Patient B was a male who was 7 years and approximately 8 months when treatment for ADHD was initiated. Patient B was administered 10 mg of Focalin XR at the initiation of treatment for ADHD. The dose of Focalin XR was raised to 15 mg approximately 8 months later. Initially, weight gain was slow and then became slightly erratic with gains of weight between follow-up appointments followed by loss of weight as shown in FIG. 6. On day 865 following the initiation of treatment with Focalin XR for ADHD, Patient B began a combination treatment that included both Focalin XR at 15 mg and Periactin at 4 mg b.i.d. Following initiation of combination therapy, Patient B began to gain weight as shown in FIG. 6, but their CGI-S score remained 3 as shown in FIG. 7. With an increase in Patient B's appetite seen following the initiation of the combination treatment, the Focalin XR dose was raised to 30 mg at day 1279 and shortly thereafter, the CGI-S score dropped to 2 as seen in FIG. 7, while the patient's weight continued to increase reaching a maximal amount as seen in FIG. 6. Through the use of Periactin, Patient B was able to increase the dose of Focalin XR without a concomitant loss of appetite, thus allowing Patient B's attentiveness to be increased.

Example 6: Patient C

Patient C was a male who was 9 years and approximately 3 months when treatment for ADHD was initiated. Patient C was administered 36 mg of Concerta at the initiation of treatment for ADHD. Initially, there was little weight gain followed by weight loss as shown in FIG. 8. On day 350 following the initiation of treatment with Concerta for ADHD, Patient C began a combination treatment that included both Concerta at 36 mg and Periactin at 4 mg b.i.d. Following initiation of combination therapy, Patient C began to gain weight as shown in FIG. 8, with a decrease in their CGI-S score from 5 to 4 as shown in FIG. 9.

Example 7: Patient D

Patient D was a male who was 7 years and approximately 1 month when treatment for ADHD was initiated. Patient D was administered 18 mg of Concerta at the initiation of treatment for ADHD. On day 23 following the initiation of treatment with Concerta for ADHD, Patient D began a combination treatment that included both Concerta at 18 mg and Periactin at 2 mg administered in the morning. Following initiation of combination therapy, Patient D began to gain weight at an accelerated pace as shown in FIG. 10, with a drop in Patient D's CGI-S score from 6 to 5 as shown in FIG. 11. With the increase in weight gain resultant from the combination treatment, Patient D was able to have the dose of Concerta increased to 27 mg, which resulted in Patient D's CGI-S score dropping again from 5 to 4 as shown in FIG. 11, with only a slight decrease in the ability of Patient D to continue to gain weight. In addition, though the change lagged the initiation of administration of Periactin to Patient D, the combination treatment also increased the growth rate in Patient D's height, even after the dose of Concerta was increased as seen in FIG. 10. Through the use of Periactin, Patient D was able to increase the dose of Concerta without a concomitant loss of appetite, thus allowing Patient D's attentiveness to be increased.

Example 8: Patient E

Patient E was a male who was 11 years and approximately two weeks when treatment for ADHD was initiated. Patient E was administered 27 mg of Concerta at the initiation of treatment for ADHD and then switched to a dose of 10 mg of Focalin XR on day 119 after initiation of treatment. Patient E was then switched to a dose of 15 mg of Focalin XR on day 162 after initiation of treatment. Increasing the dose of Focalin XR reduced Patient E's CGI-S score from 6 to 5 as shown in FIG. 13, with no additional improvement. Additionally, Patient E's weight did not increase substantively during this time as shown in FIG. 12. On day 23 following the initiation of treatment with Concerta and then Focalin XR for ADHD, Patient E began a combination treatment that included both Focalin XR at a higher dose of 20 mg and Periactin at 4 mg administered in the morning.

Following initiation of combination therapy, Patient E began to gain weight at an accelerated pace as shown in FIG. 12, which increased when Periactin was administered b.i.d. on day 836 following initiation of therapy. In addition, Patient E's CGI-S score dropped from 5 to 4 following the addition of Periactin to the combination treatment and then from 4 to 3 when the Periactin was dosed b.i.d. Through the use of Periactin, Patient E was able to increase the dose of Focalin XR without a concomitant loss of appetite, thus allowing Patient E's attentiveness to be increased.

Example 9: Patient F

Patient F was a male who was 6 years and approximately 10 months when treatment for ADHD was initiated. Patient F was administered Ritalin LA at a dose of 20 mg and Focalin at a dose of 5 mg at the initiation of treatment for ADHD and then switched to Ritalin LA at a dose of 30 mg and Focalin at a dose of 5 mg on day 46 after initiation of treatment. Patient F was then switched to a Daytrana patch at a dose of 15 mg on day 469 and then increased to a dose of 20 mg on day 606 after initiation of treatment. Increasing the dose of Ritalin LA and then switching to a Daytrana patch reduced Patient F's CGI-S score from 7 to 6 and then 6 to 5 as shown in FIG. 15, with no additional improvement. Additionally, Patient F's weight did not increase substantively during this time as shown in FIG. 14. On day 1547 following the initiation of treatment for ADHD, Patient F began a combination treatment that included both a Daytrana patch, now at a increased dose of 30 mg and Periactin at 2 mg administered b.i.d. Following initiation of combination therapy, Patient F began to gain weight at an accelerated pace as shown in FIG. 14, which increased when the dose of Periactin was increased to 4 mg b.i.d. on day 1950 following the initiation of therapy. Through the use of Periactin, Patient F was able to increase the dose of the Daytrana patch without a concomitant loss of appetite, thus allowing Patient F's attentiveness to be increased.

Example 10: Patient G

Patient G was a male who was 8 years and approximately 10 months when treatment for ADHD was initiated. Patient G was administered 15 mg of Focalin XR at the initiation of treatment for ADHD. Following initiation of treatment, Patient G's CGI-S score dropped from 5 to 4 as seen in FIG. 17. On day 546 following the initiation of treatment with Focalin XR for ADHD, Patient G began a combination treatment that included both Focalin XR at 15 mg and Periactin at 4 mg administered b.i.d. Following initiation of combination therapy, Patient G began to gain height at an accelerated pace and continued to gain weight at a good pace as shown in FIG. 16, with a drop in Patient G's CGI-S score from 4 to 3 as shown in FIG. 17. With the results seen in FIGS. 16 and 17, Patient G, the dose of Periactin administered to Patient G was decreased to 2 mg b.i.d.

Example 11: Patient H

Patient H was a male who was 11 years and approximately 6 months when treatment for ADHD was initiated. Patient H was administered 40 mg of Vvyanase at the initiation of treatment for ADHD. There was little weight gain by Patient H after initiation of treatment as shown in FIG. 18, though there was a drop in Patient H's CGI-S score from 6 to 5 as shown in FIG. 19. On day 109 following the initiation of treatment with Vvyanase for ADHD, Patient G began a combination treatment that included both Vvyanase at 40 mg and Periactin at 2 mg b.i.d. Following initiation of combination therapy, Patient G began to gain weight as shown in FIG. 18. Patient H was last seen on day 200 after initiation of treatment for ADHD, at which time the CGI-S score had not changed from the prior date of examination as seen in FIG. 19, though it is understood that an examination so soon after initiation of combination treatment does not necessarily mean that Patient H's CGI-S score did not drop further after day 200 as a result of the increase in caloric intake.

Example 12: Impact of Combination Treatment on ADHD Severity (CGI-S)

CGI-S data for each Patient A-H was plotted together in to allow examination of the effectiveness of an appetite stimulant, in this case, Periactin, to decrease the CGI-S score of the patients. As the data in FIG. 20 shows, in general, the addition of an appetite simulant to a treatment for ADHD over time lowered the CGI-S of a Patient by at least a score of 1 as compared to the same patient prior to receipt of the appetite stimulant. This is also shown in FIG. 21. In some cases, this was due in part to the ability of the patient to increase the dose of the treatment for ADHD following initiation of the combination treatment. Overall, combination treatment decreased severity as measured by CGI-S by 43% versus the baseline and showed a 22% improvement over ADHD treatment alone, with a mean CGI-S score of 4.4 with ADHD treatment alone and 3.4 for combination treatment.

Example 13: Impact of Treatment on Improvement in ADHD

Patients A-H had their CGI-I scores noted at each visit with a clinician. Measurements of the CGI-I scores of Patients A-H found that the patients CGI-I scores improved following initiation of a combination treatment as shown in FIG. 22. More particularly, patients on combination treatment had CGI-I scores that showed the patient was either minimally improved or much improved following treatment as compared to patients receiving ADHD medication only, several of whom were minimally worse or showed no change, with none showing much improved as shown in FIG. 22. Overall, combination treatment decreased severity as measured by CGI-I showed 30% improvement over ADHD treatment alone, with a mean CGI-S score of 3.4 with ADHD treatment alone and 2.4 for combination treatment.

Example 14

The patient is a 34 year old man suffering from chronic migraines. The man is administered an amphetamine along with a pain killer and the severity of the migraines are reduced over time, but the appetite of the man is similarly reduced. Over time, while taking the amphetamine and pain killer, the man loses weight and suffers fatigue and a reduction in attentiveness. The man is then administered an appetite stimulant to take with the amphetamine and pain killer. The man's migraines continue to remain significantly reduced over time, but his appetite is restored and he maintains his weight over the same period of time.

Example 15

The patient is a 42 year old woman suffering from narcolepsy. The woman is administered an amphetamine along with sleep medication and the severity of the narcolepsy is reduced over time, but the appetite of the woman is similarly reduced. Over time, while taking the amphetamine and sleep medication, the woman loses weight and suffers fatigue and a reduction in attentiveness. The woman is then administered an appetite stimulant to take with the amphetamine and sleep medication. The woman's migraines continue to remain significantly reduced over time, but her appetite is restored and she maintains his weight over the same period of time.

A method of treating an individual with a disorder associated with an attention deficit disorder, the method comprises the step of administering to an individual in need thereof a pharmaceutical composition which comprises administration of a therapeutic compound to treat the attention deficit disorder and a therapeutic compound to treat a reduction in appetite, wherein administration reduces a symptom of a disorder associated with an attention deficit disorder and increases the attentiveness of the individual, thereby treating the individual.

The method of claim 1, wherein the attention deficit disorder is Attention Deficit Hyperactivity Disorder (ADHD).

The method of claim 1, wherein the therapeutic compound administered for the treatment of an attention deficit disorder is an amphetamine or a methylphenidate.

The method of claim 3, wherein the amphetamine or methylphenidate is selected from the group consisting of OROS methylphenidate (Concerta), dextroamphetamine immediate/sustained release (Adderall/Adderall XR), dex-methylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

The method according to any one of claims 1-4, wherein the symptoms associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claims 1-4, wherein the severity associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claims 1-4, wherein the symptoms associated with attention deficit disorder is reduced by about about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claims 1-4, wherein the dose of the therapeutic compound to treat the attention deficit disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

The method according to any one of claims 1-4, wherein the dose of the therapeutic compound to treat the attention deficit disorder is in the range of about 0.001 mg/kg/day to about 100 mg/kg/day.

The method according to any one of claims 1-4, wherein the dose of the therapeutic compound to treat the attention deficit disorder is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

The method according to any of claims 1-11, wherein the therapeutic compound to treat the attention deficit disorder is administered to an individual topical, sublingual, rectal, vaginal, trancutaneous, oral, inhaled, intranasal, subcutaneous, intravenous, enteral or parenteral.

The method according to any of claims 1-11, wherein the therapeutic compound to treat the attention deficit disorder is administered as a liquid, a solid, a semi-solid or an aerosol.

The method according to any of claims 1-4, wherein the therapeutic compound is formulated as a tablet, lozenge, orally dissolved strip, capsule, syrup, oral suspension, emulsion, granule, sprinkle or pellet.

The method of claim 1, wherein the therapeutic compound is a long acting, sustained release, extended release, immediate release, slow release, or controlled release therapeutic compound.

The method of claim 14, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

The method of claim 14, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration The method of claim 14, wherein the therapeutic compound is released over a period of about 1 day after administration, about 2 days after administration, about 3 days after administration, about 4 days after administration, about 5 days after administration, about 6 days after administration or about 7 days or more after administration.

The method according to any of claim 1, wherein the pharmaceutical composition includes pharmaceutical acceptable components.

The method of claim 18, wherein the pharmaceutical acceptable components is selected from the group consisting of a salt, a surfactant, an amino acid, a stabilizer or a buffer.

The method of claim 18, wherein the salt is selected from the group consisting of citric acid, sodium chloride, potassium chloride, sodium sulfate, potassium nitrate, sodium phosphate monobasic or sodium phosphate dibasic.

The method of claim 18, wherein the surfactant is a polysorbate.

The method of claim 21, wherein the polysorbate is selected from the group consisting of Tween 20, Tween 80, F68, F88, sorbitain esters, lipids, fatty acids or fatty esters.

The method of claim 1, wherein the therapeutic compound to treat a appetite reduction is an orexigenic drug.

The method of claim 23, wherein the orexigenic drug is selected from the group of: alcohol, GHB, and other sedatives such as some benzodiazepine and nonbenzodiazepine tranquilizers and sleeping pills, anti-depressants (some SSRIs, Mianserin, etc.), 5-HT$_{2C}$ receptor antagonists/inverse agonists (e.g., mirtazapine, mianserin, olanzapine, quetiapine, risperidone, amitriptyline, imipramine, cyproheptadine, etc.), H$_1$ receptor antagonists/inverse agonists (e.g., buclizine, mirtazapine, mianserin, olanzapine, quetiapine, n-3 fatty acids, amitriptyline, chlorpheniramine maleate, etc.), D$_1$/D$_2$ receptor antagonists (e.g., haloperidol, chlorpromazine, olanzapine, risperidone, quetiapine, etc.), Marinol, Megace, Megace ES, α$_1$-adrenergic receptor antagonists (such as doxazosin, carvedilol, propanolol, colonidine), Serefam, α$_2$-adrenergic receptor agonists (e.g., clonidine, guanfacine, etc.), some beta blockers such as propanolol, natural or synthetic CBI receptor agonists (e.g., THC or dronabinol (found in *Cannabis*), tetrahydrocannibinol, diphenydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesteronemirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-HT$_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants.

The method of claim 23, wherein the orexigenic drug is cyproheptadine hydrochloride.

The method according to any one of claim 1 or 23-25, wherein the symptoms associated with appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claim 1 or 23-25, wherein the symptoms associated with appetite reduction is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 1 or 23-25, wherein the symptoms associated with reduction in the severity of appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 1 or 23-25, wherein the severity associated with reduction in appetite is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 1 or 23-25, wherein the treatment for appetite reduction results in an increase in weight by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 1 or 23-25, wherein the treatment for appetite reduction results in an increase in weight by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 1 or 23-25, wherein the treatment for appetite reduction results in an increase in height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 1 or 23-25, wherein the treatment for appetite reduction results in an increase in weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

The method according to any of claim 1 or 23-25, wherein the treatment for appetite reduction increases the attentiveness of a patient by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any of claim 1 or 23-25, wherein the treatment for appetite reduction increases the attentiveness of a patient by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 1 or 23-35, wherein the dose of the therapeutic compound to treat the reduction in appetite is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

The method according to any one of claim 1 or 23-35, wherein the dose of the therapeutic compound to treat reduction in appetite is in the range of about 0.001 mg/kg/day to about 100 mg/kg/day.

The method according to any one of claim 1 or 23-35, wherein the dose of the therapeutic compound to treat the reduction in appetite is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

The method according to any of claim 1 or 23-25, wherein the therapeutic compound to treat the reduction in appetite is administered to an individual topical, sublingual, rectal, vaginal, trancutaneous, oral, inhaled, intranasal, subcutaneous, intravenous, enteral or parenteral.

The method according to any of claim 1 or 23-35, wherein the therapeutic compound to treat the reduction in appetite is administered as a liquid, a solid, a semi-solid or an aerosol.

The method according to any of claim 1 or 23-35, wherein the therapeutic compound is formulated as a tablet, lozenge, orally dissolved strip, capsule, syrup, oral suspension, emulsion, granule, sprinkle or pellet.

The method according to any of claim 1 or 23-35, wherein the therapeutic compound is a long acting, sustained release, extended release, immediate release, slow release, or controlled release therapeutic compound.

The method according to any of claim 1 or 23-35, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

The method according to any of claim 1 or 23-35, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration The method according to any of claim 1 or 23-35, wherein the therapeutic compound is released over a period of about 1 day after administration, about 2 days after administration, about 3 days after administration, about 4 days after administration, about 5 days after administration, about 6 days after administration or about 7 days or more after administration.

The method according to any of claim 1 or 23-35, wherein the pharmaceutical composition includes pharmaceutical acceptable components.

The method of claim 46, wherein the pharmaceutical acceptable components is selected from the group consisting of a salt, a surfactant, an amino acid, a stabilizer or a buffer.

The method of claim 47, wherein the salt is selected from the group consisting of citric acid, sodium chloride, potassium chloride, sodium sulfate, potassium nitrate, sodium phosphate monobasic or sodium phosphate dibasic.

The method of claim 46, wherein the surfactant is a polysorbate.

The method of claim 49, wherein the polysorbate is selected from the group consisting of Tween 20, Tween 80, F68, F88, sorbitain esters, lipids, fatty acids or fatty esters.

The method of claim 1, wherein the increase in attentiveness by an individual is measured by CGI-S.

The method of claim 51, wherein the CGI-S scale is from 1 to 7.

The method of claim 52, wherein a measurement of 7 identifies an individual that is extremely ill, 6 identifies an individual that is severely ill, 5 identifies an individual that is markedly ill, 4 identifies an individual that is moderately ill, 3 identifies an individual that is mildly ill, 2 identifies an individual that is borderline ill and a measurement of 1 identifies an individual that is normal.

The method of any of claim 1 or 51-53, wherein the increase in attentiveness measured by CGI-S is by a reduction in the score by 1 or more as compared to a patient not receiving a therapeutic compound to treat a appetite reduction.

The method of any of claim 1 or 51-53, wherein the patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method of any of claim 1 or 51-53, wherein the patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method of claim 1, wherein the increase in attentiveness by an individual is measured by CGI-I.

The method of claim 57, wherein the CGI-I scale is from 1 to 7.

The method of claim 58, wherein a measurement of 7 identifies an individual that is very much worse, 6 identifies an individual that is much worse, 5 identifies an individual that is minimally worse, 4 identifies an individual that is no change, 3 identifies an individual that is minimally improved, 2 identifies an individual that is much improved and a measurement of 1 identifies an individual that is very much improved.

The method of any of claim 1 or 57-59, wherein the increase in attentiveness measured CGI-I is by a reduction in the score by 1 or more as compared to a patient not receiving a therapeutic compound to treat a reduction in appetite.

The method of any of claim 1 or 57-59, wherein the patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method of any of claim 1 or 57-59, wherein the patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method of claim 1, wherein the increase in attentiveness by an individual is measured by the p academic performance rating scale, ADD evaluation scale-3$^{rd}$ edition (ADDES-3), ADHD rating scale-IV (ADHD-RS-IV), youth self report (broadband instrument), Conners parent rating scale-revised (CPRS-R), Conners teacher rating scale-revised (CTRS-R), Conners 3 self-reporting scale (Conner 3-SR; ages 8-18y), home situations questionnaire-revised, inattention/overactivity with aggression (IOWA) Conners teacher's rating scale, Swanson Nolan and Pelham IV scale (SNAP-IV), Swanson Kotkin Agler M-Flynn and Pelham (SKAMP), Vanderbilt ADHD diagnostic parent rating scale (VADPRS), Vanderbilt ADHD diagnostic teacher rating scale (VADTRS), behavior assessment system for children-2$^{nd}$ edition (BASC-2) or the Conners rating scale long version.

A pharmaceutical composition comprising a therapeutic compound for a disorder associated with an attention deficit disorder and a therapeutic compound for a disorder associated with a reduction in appetite, wherein the pharmaceutical composition reduces a symptom of a disorder associated with an attention deficit disorder and increases the attentiveness of the individual, thereby treating the individual.

A pharmaceutical composition of claim 64, wherein the attention deficit disorder is Attention Deficit Hyperactivity Disorder (ADHD).

A pharmaceutical composition of claim 64, wherein the therapeutic compound administered for the treatment of an attention deficit disorder is an amphetamine or a methylphenidate.

A pharmaceutical composition of claim 66, wherein the amphetamine or methylphenidate is selected from the group consisting of OROS methylphenidate (Concerta), dextroamphetamine immediate/sustained release (Adderall/Adderall XR), dexmethylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

A pharmaceutical composition according to any one of claims 64-67, wherein the symptoms associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 64-67, wherein the severity associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 64-67, wherein the symptoms associated with attention deficit disorder is reduced by about about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 64-67, wherein the dose of the therapeutic compound to treat the attention deficit disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

A pharmaceutical composition according to any one of claims 64-67, wherein the dose of the therapeutic compound to treat the attention deficit disorder is in the range of about 0.001 mg/kg/day to about 100 mg/kg/day.

A pharmaceutical composition according to any one of claims 64-67, wherein the dose of the therapeutic compound to treat the attention deficit disorder is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

A pharmaceutical composition according to any one of claims 64-67, wherein the therapeutic compound to treat the attention deficit disorder is administered to an individual topical, sublingual, rectal, vaginal, trancutaneous, oral, inhaled, intranasal, subcutaneous, intravenous, enteral or parenteral.

A pharmaceutical composition according to any one of claims 64-67, wherein the therapeutic compound to treat the attention deficit disorder is administered as a liquid, a solid, a semi-solid or an aerosol.

A pharmaceutical composition according to any one of claims 64-67, wherein the therapeutic compound is formulated as a tablet, lozenge, orally dissolved strip, capsule, syrup, oral suspension, emulsion, granule, sprinkle or pellet.

A pharmaceutical composition according to claim 64, wherein the therapeutic compound is a long acting, sustained release, extended release, immediate release, slow release, or controlled release therapeutic compound.

A pharmaceutical composition according to claim 77, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

A pharmaceutical composition according to claim 77, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration A pharmaceutical composition according to claim 77, wherein the therapeutic compound is released over a period of about 1 day after administration, about 2 days after administration, about 3 days after administration, about 4 days after administration, about 5 days after administration, about 6 days after administration or about 7 days or more after administration.

A pharmaceutical composition according to claim 1, wherein the pharmaceutical composition includes pharmaceutical acceptable components.

A pharmaceutical composition according to claim 81, wherein the pharmaceutical acceptable components is selected from the group consisting of a salt, a surfactant, an amino acid, a stabilizer or a buffer.

A pharmaceutical composition according to claim 82, wherein the salt is selected from the group consisting of citric acid, sodium chloride, potassium chloride, sodium sulfate, potassium nitrate, sodium phosphate monobasic or sodium phosphate dibasic.

A pharmaceutical composition according to 81, wherein the surfactant is a polysorbate.

A pharmaceutical composition according to claim 84, wherein the polysorbate is selected from the group consisting of Tween 20, Tween 80, F68, F88, sorbitain esters, lipids, fatty acids or fatty esters.

A pharmaceutical composition according to claim 64, wherein the therapeutic compound to treat a appetite reduction is an orexigenic drug.

A pharmaceutical composition according to claim 86, wherein the orexigenic drug is selected from the group of: alcohol, GHB, and other sedatives such as some benzodiazepine and nonbenzodiazepine tranquilizers and sleeping pills, anti-depressants (some SSRIs, Mianserin, etc.), 5-$HT_{2C}$ receptor antagonists/inverse agonists (e.g., mirtazapine, mianserin, olanzapine, quetiapine, risperidone, amitriptyline, imipramine, cyproheptadine, etc.), $H_1$ receptor antagonists/inverse agonists (e.g., buclizine, mirtazapine, mianserin, olanzapine, quetiapine, n-3 fatty acids, amitriptyline, chlorpheniramine maleate, etc.), $D_1$/$D_2$ receptor antagonists (e.g., haloperidol, chlorpromazine, olanzapine, risperidone, quetiapine, etc.), Marinol, Megace, Megace ES, $\alpha_1$-adrenergic receptor antagonists (such as doxazosin, carvedilol, propanolol, colonidine), Serefam, $\alpha_2$-adrenergic receptor agonists (e.g., clonidine, guanfacine, etc.), some beta blockers such as propanolol, natural or synthetic CBI receptor agonists (e.g., THC or dronabinol (found in *Cannabis*), tetrahydrocannibinol, diphenydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesteronemirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-HT$_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants.

A pharmaceutical composition according to claim 87, wherein the orexigenic drug is cyproheptadine hydrochloride.

A pharmaceutical composition according to any one of claims 64 and 86-88, wherein the symptoms associated with appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 64 and 86-88, wherein the symptoms associated with appetite reduction is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 64 and 86-88, wherein the symptoms associated with reduction in the severity of appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 64 and 86-88, wherein the severity associated with reduction in appetite is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 64 and 86-88, wherein the treatment for appetite reduction results in an increase in weight by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 64 and 86-88, wherein the treatment for appetite reduction results in an increase in weight by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 64 and 86-88, wherein the treatment for appetite reduction results in an increase in height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 64 and 86-88, wherein the treatment for appetite reduction results in an increase in weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

A pharmaceutical composition according to any one of claims 64 and 86-88, wherein the treatment for appetite reduction increases the attentiveness of a patient by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 64 and 86-88, wherein the treatment for appetite reduction increases the attentiveness of a patient by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 64 and 86-88, wherein the dose of the therapeutic compound to treat the reduction in appetite is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

A pharmaceutical composition according to any one of claims 64 and 86-88, wherein the dose of the therapeutic compound to treat reduction in appetite is in the range of about 0.001 mg/kg/day to about 100 mg/kg/day.

A pharmaceutical composition according to any one of claims 64 and 86-88, wherein the dose of the therapeutic compound to treat the reduction in appetite is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

A pharmaceutical composition according to any one of claims 64 and 86-88, wherein the therapeutic compound to treat the reduction in appetite is administered to an individual topical, sublingual, rectal, vaginal, trancutaneous, oral, inhaled, intranasal, subcutaneous, intravenous, enteral or parenteral.

A pharmaceutical composition according to any one of claims 64 and 86-102, wherein the therapeutic compound to treat the reduction in appetite is administered as a liquid, a solid, a semi-solid or an aerosol.

A pharmaceutical composition according to any one of claims 64 and 86-102, wherein the therapeutic compound is formulated as a tablet, lozenge, orally dissolved strip, capsule, syrup, oral suspension, emulsion, granule, sprinkle or pellet.

A pharmaceutical composition according to any one of claims 64 and 86-103, wherein the therapeutic compound is a long acting, sustained release, extended release, immediate release, slow release, or controlled release therapeutic compound.

A pharmaceutical composition according to any one of claims 64 and 86-103, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

A pharmaceutical composition according to any one of claims 64 and 86-103, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration A pharmaceutical composition according to any one of claims 64 and 86-103, wherein the therapeutic compound is released over a period of about 1 day after administration, about 2 days after administration, about 3 days after administration, about 4 days after administration, about 5 days after administration, about 6 days after administration or about 7 days or more after administration.

A pharmaceutical composition according to any one of claims 64 and 86-108, wherein the pharmaceutical composition includes pharmaceutical acceptable components.

A pharmaceutical composition according to claim 109, wherein the pharmaceutical acceptable components is selected from the group consisting of a salt, a surfactant, an amino acid, a stabilizer or a buffer.

A pharmaceutical composition according to claim 110, wherein the salt is selected from the group consisting of citric acid, sodium chloride, potassium chloride, sodium sulfate, potassium nitrate, sodium phosphate monobasic or sodium phosphate dibasic.

A pharmaceutical composition according to claim 110, wherein the surfactant is a polysorbate.

A pharmaceutical composition according to claim 112, wherein the polysorbate is selected from the group consisting of Tween 20, Tween 80, F68, F88, sorbitain esters, lipids, fatty acids or fatty esters.

A pharmaceutical composition according to claim 64, wherein the increase in attentiveness by an individual is measured by CGI-S.

A pharmaceutical composition according to claim 114, wherein the CGI-S scale is from 1 to 7.

A pharmaceutical composition according to claim 115, wherein a measurement of 7 identifies an individual that is extremely ill, 6 identifies an individual that is severely ill, 5 identifies an individual that is markedly ill, 4 identifies an individual that is moderately ill, 3 identifies an individual that is mildly ill, 2 identifies an individual that is borderline ill and a measurement of 1 identifies an individual that is normal.

A pharmaceutical composition according to any of claim 64 or 114-116, wherein the increase in attentiveness measured by CGI-S is by a reduction in the score by 1 or more as compared to a patient not receiving a therapeutic compound to treat a appetite reduction.

A pharmaceutical composition according to any of claim 64 or 114-116, wherein the patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any of claim 64 or 114-116, wherein the patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to claim 64, wherein the increase in attentiveness by an individual is measured on by CGI-I.

A pharmaceutical composition according to claim 120, wherein the CGI-I scale is from 1 to 7.

A pharmaceutical composition according to claim 121, wherein a measurement of 7 identifies an individual that is very much worse, 6 identifies an individual that is much worse, 5 identifies an individual that is minimally worse, 4 identifies an individual that is no change, 3 identifies an individual that is minimally improved, 2 identifies an individual that is much improved and a measurement of 1 identifies an individual that is very much improved.

A pharmaceutical composition according to any of claim 64 or 120-122, wherein the increase in attentiveness measured CGI-I is by a reduction in the score by 1 or more as compared to a patient not receiving a therapeutic compound to treat a reduction in appetite.

A pharmaceutical composition according to any of claim 64 or 120-122, wherein the patient's CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any of claim 64 or 120-122, wherein the patient's CGI-S score is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to claim 64, wherein the increase in attentiveness by an individual is measured by the p academic performance rating scale, ADD evaluation scale-3$^{rd}$ edition (ADDES-3), ADHD rating scale-IV (ADHD-RS-IV), youth self report (broadband instrument), Conners parent rating scale-revised (CPRS-R), Conners teacher rating scale-revised (CTRS-R), Conners 3 self-reporting scale (Conner 3-SR; ages 8-18y), home situations questionnaire-revised, inattention/overactivity with aggression (IOWA) Conners teacher's rating scale, Swanson Nolan and Pelham IV scale (SNAP-IV), Swanson Kotkin Agler M-Flynn and Pelham (SKAMP), Vanderbilt ADHD diagnostic parent rating scale (VADPRS), Vanderbilt ADHD diagnostic teacher rating scale (VADTRS), behavior assessment system for children-2$^{nd}$ edition (BASC-2) or the Conners rating scale long version.

A method of treating an individual with a disorder associated with a psychological and/or neurological disorder, the method comprises the step of administering to an individual in need thereof a pharmaceutical composition which comprises a therapeutic compound consisting of an amphetamine and/or a methylphenidate and a therapeutic compound to treat a reduction in appetite, thereby treating the individual.

The method of claim 127, wherein, the psychological and/or neurological disorder is selected from the group of migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and/or tic.

The method of claim 127, wherein the therapeutic compound to treat phychological or neurological disorder is an amphetamine or methylphenidate.

The method of claim 129, wherein the amphetamine or methylphenidate is selected from the group consisting of OROS methylphenidate (Concerta), dextroamphetamine immediate/sustained release (Adderall/Adderall XR), dexmethylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

The method according to any one of claims 127-130, wherein the symptoms associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claims 127-130, wherein the severity associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claims 127-130, wherein the symptoms associated with attention deficit disorder is reduced by about about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claims 127-130, wherein the dose of the therapeutic compound to treat the attention deficit disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

The method according to any one of claims 127-130, wherein the dose of the therapeutic compound to treat the attention deficit disorder is in the range of about 0.001 mg/kg/day to about 100 mg/kg/day.

The method according to any one of claims 127-130, wherein the dose of the therapeutic compound to treat the attention deficit disorder is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

The method according to any of claims 127-136, wherein the therapeutic compound to treat the attention deficit disorder is administered to an individual topical, sublingual, rectal, vaginal, trancutaneous, oral, inhaled, intranasal, subcutaneous, intravenous, enteral or parenteral.

The method according to any of claims 127-136, wherein the therapeutic compound to treat the attention deficit disorder is administered as a liquid, a solid, a semi-solid or an aerosol.

The method according to any of claims 127-130, wherein the therapeutic compound is formulated as a tablet, lozenge, orally dissolved strip, capsule, syrup, oral suspension, emulsion, granule, sprinkle or pellet.

The method of claim 127, wherein the therapeutic compound is a long acting, sustained release, extended release, immediate release, slow release, or controlled release therapeutic compound.

The method of claim 140, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

The method of claim 140, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration The method of claim 140, wherein the therapeutic compound is released over a period of about 1 day after administration, about 2 days after administration, about 3 days after administration, about 4 days after administration, about 5 days after administration, about 6 days after administration or about 7 days or more after administration.

The method according to any of claim 127, wherein the pharmaceutical composition includes pharmaceutical acceptable components.

The method of claim 144, wherein the pharmaceutical acceptable components is selected from the group consisting of a salt, a surfactant, an amino acid, a stabilizer or a buffer.

The method of claim 145, wherein the salt is selected from the group consisting of citric acid, sodium chloride, potassium chloride, sodium sulfate, potassium nitrate, sodium phosphate monobasic or sodium phosphate dibasic.

The method of claim 144, wherein the surfactant is a polysorbate.

The method of claim 147, wherein the polysorbate is selected from the group consisting of Tween 20, Tween 80, F68, F88, sorbitain esters, lipids, fatty acids or fatty esters.

The method of claim 127, wherein the therapeutic compound to treat an appetite reduction is an orexigenic drug.

The method of claim 149, wherein the orexigenic drug is selected from the group of: alcohol, GHB, and other sedatives such as some benzodiazepine and nonbenzodiazepine tranquilizers and sleeping pills, anti-depressants (some SSRIs, Mianserin, etc.), 5-HT$_{2C}$ receptor antagonists/inverse agonists (e.g., mirtazapine, mianserin, olanzapine, quetiapine, risperidone, amitriptyline, imipramine, cyproheptadine, etc.), H$_1$ receptor antagonists/inverse agonists (e.g., buclizine, mirtazapine, mianserin, olanzapine, quetiapine, n-3 fatty acids, amitriptyline, chlorpheniramine maleate, etc.), D$_1$/D$_2$ receptor antagonists (e.g., haloperidol, chlorpromazine, olanzapine, risperidone, quetiapine, etc.), Marinol, Megace, Megace ES, α$_1$-adrenergic receptor antagonists (such as doxazosin, carvedilol, propanolol, colonidine), Serefam, α$_2$-adrenergic receptor agonists (e.g., clonidine, guanfacine, etc.), some beta blockers such as propanolol, natural or synthetic CBI receptor agonists (e.g., THC or dronabinol (found in *Cannabis*), tetrahydrocannibinol, diphenydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesteronemirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-HT$_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants.

The method of claim 149, wherein the orexigenic drug is cyproheptadine hydrochloride.

The method according to any one of claim 127 or 149-151, wherein the symptoms associated with appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The method according to any one of claim 127 or 149-151, wherein the symptoms associated with appetite reduction is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 127 or 149-151, wherein the symptoms associated with reduction in the severity of appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 127 or 149-151, wherein the severity associated with reduction in appetite is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 127 or 149-151, wherein the treatment for appetite reduction results in an increase in weight by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 127 or 149-151, wherein the treatment for appetite reduction results in an increase in weight by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 127 or 149-151, wherein the treatment for appetite reduction results in an increase in height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any one of claim 127 or 149-151, wherein the treatment for appetite reduction results in an increase in weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

The method according to any of claim 127 or 149-151, wherein the treatment for appetite reduction increases the attentiveness of a patient by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

The method according to any of claim 127 or 149-151, wherein the treatment for appetite reduction increases the attentiveness of a patient by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

The method according to any one of claim 127 or 149-161, wherein the dose of the therapeutic compound to treat the reduction in appetite is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

The method according to any one of claim 127 or 149-161, wherein the dose of the therapeutic compound to treat reduction in appetite is in the range of about 0.001 mg/kg/day to about 100 mg/kg/day.

The method according to any one of claim 127 or 149-161, wherein the dose of the therapeutic compound to treat the reduction in appetite is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

The method according to any of claim 127 or 149-161, wherein the therapeutic compound to treat the reduction in appetite is administered to an individual topical, sublingual, rectal, vaginal, trancutaneous, oral, inhaled, intranasal, subcutaneous, intravenous, enteral or parenteral.

The method according to any of claim 127 or 149-161, wherein the therapeutic compound to treat the reduction in appetite is administered as a liquid, a solid, a semi-solid or an aerosol.

The method according to any of claim 127 or 149-161, wherein the therapeutic compound is formulated as a tablet, lozenge, orally dissolved strip, capsule, syrup, oral suspension, emulsion, granule, sprinkle or pellet.

The method according to any of claim 127 or 149-161, wherein the therapeutic compound is a long acting, sustained release, extended release, immediate release, slow release, or controlled release therapeutic compound.

The method according to any of claim 1 or 23-35, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

The method according to any of claim 127 or 149-161, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration The method according to any of claim 127 or 149-161, wherein the therapeutic compound is released over a period of about 1 day after administration, about 2 days after administration, about 3 days after administration, about 4 days after administration, about 5 days after administration, about 6 days after administration or about 7 days or more after administration.

The method according to any of claim 127 or 149-161, wherein the pharmaceutical composition includes pharmaceutical acceptable components.

The method of claim 172, wherein the pharmaceutical acceptable components is selected from the group consisting of a salt, a surfactant, an amino acid, a stabilizer or a buffer.

The method of claim 173, wherein the salt is selected from the group consisting of citric acid, sodium chloride, potassium chloride, sodium sulfate, potassium nitrate, sodium phosphate monobasic or sodium phosphate dibasic.

The method of claim 172, wherein the surfactant is a polysorbate.

The method of claim 175, wherein the polysorbate is selected from the group consisting of Tween 20, Tween 80, F68, F88, sorbitain esters, lipids, fatty acids or fatty esters.

A pharmaceutical composition for the treatment of an individual with a disorder associated with a psychological and/or neurological disorder, which comprises a therapeutic compound consisting of an amphetamine and/or a methylphenidate and a therapeutic compound to treat a reduction in appetite, thereby treating the individual.

The pharmaceutical composition of claim 177, wherein, the psychological and/or neurological disorder is selected from the group of migrane, anti-serotonergic side effects, narcolepsy, excessive sleepiness associated with shift work, obstructive sleep apnea as an adjunct to continuous positive airways pressure ("CPAP"), exogenous obesity, disruptive behaviour disorder including oppositional defiant disorder ("ODD") and conduct disorder ("CD"), obesity, depression (including, without limitation, augmentation of antidepressants in treating refractory depression and cancer-related depression), neural insult, fatigue (including, without limitation, disease-related fatigue in patients with HIV, advanced cancer, multiple sclerosis, myotonic dystrophy, depression, fibromyalgia and hepatitis C), lethargy, binge eating disorder, schizophrenia, sleep cycle disorder, cocaine addiction, Parkinson's Disease, combat and non-combat related PTSD and/or tic.

A pharmaceutical composition of claim 177, wherein the therapeutic compound administered for the treatment of a psychological or neurological disorder is an amphetamine or a methylphenidate.

A pharmaceutical composition of claim 179, wherein the amphetamine or methylphenidate is selected from the group consisting of OROS methylphenidate (Concerta), dextroamphetamine immediate/sustained release (Adderall/Adderall XR), dexmethylphenidate (Focalin), Focalin XR, Metadate CD, Metadate ER, NWP09, Dexedrine, dextroamphetamine (Dexedrine), Dexedrine Spansules, Methylin ER (Ritalin SR), methylphenidate (Ritalin), and methylphenidate CR, Ritalin, Ritalin LA, SD-483, SPD-503, Ritalin SR, Intuniv ER, Intuniv, Methylin, Daytrana, Equasym, Dixirit, Kapvay, Daytrana Patch, Methylin chewable, Methylin liquid, Dextrostat, Strattera, Tenex, Catapres, Catapres TTS patch, Prozac, Serefam, Zoloft, Luvox, Paxil, Paxil CR, Pexeva, Celexa, Lexapro, Tofranil, Norpamin, Elavil, Pamelor, Sinequan, Anafranil, Wellbutrin, Wellbutrin SR, Wellbutrin XL, Effexor, Effexor XR, Remeron, Cymbalta, Nardil, Parnate, Emsam patch, Haldol, Orap, Prolixin, Mellaril, Thorazine, Stelazine, Moban, Loxitane, Risperdal, Zyprexa, Seroquel, Geodon, Abilify, Clozaril, Xanax, Xanax XR, Klonopin, Ativan, Buspar, Ambien CR, Ambien, Lunesta, Sonata, Rozerem, Lithiu, Lithobid, Eskalith, Depakote, Tegretol, Carbatrol, Trileptal, Lamictal, Topamax, Neurontin and the therapeutic compounds identified in Table 1.

A pharmaceutical composition according to any one of claims 177-180, wherein the symptoms associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 177-180, wherein the severity associated with attention deficit disorder is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 177-180, wherein the symptoms associated with attention deficit disorder is reduced by about about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 177-180, wherein the dose of the therapeutic compound to treat the attention deficit disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

A pharmaceutical composition according to any one of claims 177-180, wherein the dose of the therapeutic compound to treat the attention deficit disorder is in the range of about 0.001 mg/kg/day to about 100 mg/kg/day.

A pharmaceutical composition according to any one of claims 177-180, wherein the dose of the therapeutic compound to treat the attention deficit disorder is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

A pharmaceutical composition according to any one of claims 177-180, wherein the therapeutic compound to treat the attention deficit disorder is administered to an individual topical, sublingual, rectal, vaginal, trancutaneous, oral, inhaled, intranasal, subcutaneous, intravenous, enteral or parenteral.

A pharmaceutical composition according to any one of claims 177-180, wherein the therapeutic compound to treat the attention deficit disorder is administered as a liquid, a solid, a semi-solid or an aerosol.

A pharmaceutical composition according to any one of claims 177-180, wherein the therapeutic compound is formulated as a tablet, lozenge, orally dissolved strip, capsule, syrup, oral suspension, emulsion, granule, sprinkle or pellet.

A pharmaceutical composition according to claim 177, wherein the therapeutic compound is a long acting, sustained release, extended release, immediate release, slow release, or controlled release therapeutic compound.

A pharmaceutical composition according to claim 190, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

A pharmaceutical composition according to claim 190, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration A pharmaceutical composition according to claim 190, wherein the therapeutic compound is released over a period of about 1 day after administration, about 2 days after administration, about 3 days after administration, about 4 days after administration, about 5 days after administration, about 6 days after administration or about 7 days or more after administration.

A pharmaceutical composition according to claim 177, wherein the pharmaceutical composition includes pharmaceutical acceptable components.

A pharmaceutical composition according to claim 194, wherein the pharmaceutical acceptable components is selected from the group consisting of a salt, a surfactant, an amino acid, a stabilizer or a buffer.

A pharmaceutical composition according to claim 195, wherein the salt is selected from the group consisting of citric acid, sodium chloride, potassium chloride, sodium sulfate, potassium nitrate, sodium phosphate monobasic or sodium phosphate dibasic.

A pharmaceutical composition according to 194, wherein the surfactant is a polysorbate.

A pharmaceutical composition according to claim 197, wherein the polysorbate is selected from the group consisting of Tween 20, Tween 80, F68, F88, sorbitain esters, lipids, fatty acids or fatty esters.

A pharmaceutical composition according to claim 177, wherein the therapeutic compound to treat a appetite reduction is an orexigenic drug.

A pharmaceutical composition according to claim 199, wherein the orexigenic drug is selected from the group of: alcohol, GHB, and other sedatives such as some benzodiazepine and nonbenzodiazepine tranquilizers and sleeping pills, anti-depressants (some SSRIs, Mianserin, etc.), 5-HT$_{2C}$ receptor antagonists/inverse agonists (e.g., mirtazapine, mianserin, olanzapine, quetiapine, risperidone, amitriptyline, imipramine, cyproheptadine, etc.), H$_1$ receptor antagonists/inverse agonists (e.g., buclizine, mirtazapine, mianserin, olanzapine, quetiapine, n-3 fatty acids, amitriptyline, chlorpheniramine maleate, etc.), D$_1$/D$_2$ receptor antagonists (e.g., haloperidol, chlorpromazine, olanzapine, risperidone, quetiapine, etc.), Marinol, Megace, Megace ES, α$_1$-adrenergic receptor antagonists (such as doxazosin, carvedilol, propanolol, colonidine), Serefam, α$_2$-adrenergic receptor agonists (e.g., clonidine, guanfacine, etc.), some beta blockers such as propanolol, natural or synthetic CBI receptor agonists (e.g., THC or dronabinol (found in *Cannabis*), tetrahydrocannibinol, diphenydramine, promethazine, B vitamin supplements, nabilone, JWH-018 etc.), Corticosteroids (e.g. prednisone or dexamethasone), Sodium valproate (Depakote), Megestrol, Pregabalin, Sulfonylurea antidiabetic drugs such as glibenclamide and chlorpropamide, steroids (including, without limitation, boldenone, oxymetholone, dexamethasone, or methandrostenolone, prednisone, hydrocortisone, oxandrolone, nandrolone, testosterone), some kappa opioid receptor agonists such as tifluadom, hormones such as mederoxyprogesteronemirtazapine (Remeron), a tetracyclic antidepressant; cyproheptadine (Periactin), an antihistamine; nandrolone, oxymetholone, and oxandrolone (Anadrol-50, Durabolin, Hybolin, anti-IL6 antibody, selective androgen receptor modulator ("SARM"), Oxandrin, and other brand names), VT-122 (a coadministration of propranolol and etodolac), type 4 melanocortin receptor antagonis, IL6 antagonist, synthetic ghrelin, myostatin decoy receptor, fast skeletal muscle troponin-activating substance, anticatabolic/anabolic transforming agent MT-102, celecoxib, testosterone, vitamin D, OHR/AVR118, soluble version of the ActRIIB receptor, 5-$HT_3$ antagonists, Cox-2 inhibitor, thalidomide, omega-3 fatty acids, anticyclooxygenase-2 drugs and megestrol acetate (Megace). In addition to these prescription drugs, fish oil (eicosapentaenoic acid or EPA), EATMOR, other vitamins and natural or artificial appetite stimulants.

A pharmaceutical composition according to claim 199, wherein the orexigenic drug is cyproheptadine hydrochloride.

A pharmaceutical composition according to any one of claims 177 and 199-201, wherein the symptoms associated with appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

A pharmaceutical composition according to any one of claims 177 and 199-201, wherein the symptoms associated with appetite reduction is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 177 and 199-201, wherein the symptoms associated with reduction in the severity of appetite reduction is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 177 and 199-201, wherein the severity associated with reduction in appetite is reduced by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 177 and 199-201, wherein the treatment for appetite reduction results in an increase in weight by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 177 and 199-201, wherein the treatment for appetite reduction results in an increase in weight by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 177 and 199-201, wherein the treatment for appetite reduction results in an increase in height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 177 and 199-201, wherein the treatment for appetite reduction results in an increase in weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, at least 50 pounds. In another embodiment, a therapeutic compound disclosed herein for the treatment of appetite reduction results in an increase in weight by, e.g., from 0.5 pounds to 50 pounds, from 0.5 pounds to 30 pounds, from 0.5 pounds to 25 pounds, from 0.5 pounds to 20 pounds, from 0.5 pounds to 15 pounds, from 0.5 pounds to ten pounds, from 0.5 pounds to 7.5 pounds, from 0.5 pounds to 5 pounds, from 1 pound to 15 pounds, from 1 pound to 10 pounds, from 1 pound to 7.5 pounds, form 1 pound to 5 pounds, from 2 pounds to ten pounds, from 2 pounds to 7.5 pounds.

A pharmaceutical composition according to any one of claims 177 and 199-201, wherein the treatment for appetite reduction increases the attentiveness of a patient by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A pharmaceutical composition according to any one of claims 177 and 199-201, wherein the treatment for appetite reduction increases the attentiveness of a patient by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition according to any one of claims 177 and 199-201, wherein the dose of the therapeutic compound to treat the reduction in appetite is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

A pharmaceutical composition according to any one of claims 177 and 199-201, wherein the dose of the therapeutic compound to treat reduction in appetite is in the range of about 0.001 mg/kg/day to about 100 mg/kg/day.

A pharmaceutical composition according to any one of claims 177 and 199-201, wherein the dose of the therapeutic compound to treat the reduction in appetite is in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day.

A pharmaceutical composition according to any one of claims 177 and 199-201, wherein the therapeutic compound to treat the reduction in appetite is administered to an individual topical, sublingual, rectal, vaginal, trancutaneous, oral, inhaled, intranasal, subcutaneous, intravenous, enteral or parenteral.

A pharmaceutical composition according to any one of claims 177 and 199-215, wherein the therapeutic compound to treat the reduction in appetite is administered as a liquid, a solid, a semi-solid or an aerosol.

A pharmaceutical composition according to any one of claims 177 and 199-215, wherein the therapeutic compound is formulated as a tablet, lozenge, orally dissolved strip, capsule, syrup, oral suspension, emulsion, granule, sprinkle or pellet.

A pharmaceutical composition according to any one of claims 177 and 199-215, wherein the therapeutic compound is a long acting, sustained release, extended release, immediate release, slow release, or controlled release therapeutic compound.

A pharmaceutical composition according to any one of claims 177 and 199-215, wherein the therapeutic compound is released over a period of about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration.

A pharmaceutical composition according to any one of claims 177 and 199-218, wherein the therapeutic compound is released over a period of at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration A pharmaceutical composition according to any one of claims 199-218, wherein the therapeutic compound is released over a period of about 1 day after administration, about 2 days after administration, about 3 days after administration, about 4 days after administration, about 5 days after administration, about 6 days after administration or about 7 days or more after administration.

A pharmaceutical composition according to any one of claims 199-218, wherein the pharmaceutical composition includes pharmaceutical acceptable components.

A pharmaceutical composition according to claim 222, wherein the pharmaceutical acceptable components is selected from the group consisting of a salt, a surfactant, an amino acid, a stabilizer or a buffer.

A pharmaceutical composition according to claim 223, wherein the salt is selected from the group consisting of citric acid, sodium chloride, potassium chloride, sodium sulfate, potassium nitrate, sodium phosphate monobasic or sodium phosphate dibasic.

A pharmaceutical composition according to claim 222, wherein the surfactant is a polysorbate.

A pharmaceutical composition according to claim 225, wherein the polysorbate is selected from the group consisting of Tween 20, Tween 80, F68, F88, sorbitain esters, lipids, fatty acids or fatty esters.

A kit comprising a pharmaceutical composition of any preceding claim.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of increasing attentiveness and weight velocity in an individual having an attention deficit disorder, the method comprising:
coadministering to the individual a therapeutically effective amount of methylphenidate and a therapeutically effective amount of cyproheptadine;
wherein the methylphenidate and cyproheptadine are coadministered during at least one of the morning or afternoon;
wherein the cyproheptadine is not administered in the evening or before bedtime; and
wherein the method increases the individual's weight velocity as compared to an individual receiving only methylphenidate; and
wherein the method increases the individual's height velocity as compared to an individual receiving only methylphenidate.

2. The method of claim 1, wherein the method increases the individual's weight velocity for up to 1,108 days or more.

3. The method of claim 1, wherein the cyproheptadine maintains mean peak plasma level for at least 6 hours during the individual's waking hours.

4. The method of claim 1, wherein the method increases the individual's baseline height by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

5. The method of claim 4, wherein the method increases the individual's baseline height by at least 95%.

6. The method of claim 1, wherein the method increases the individual's height velocity by 98%.

7. The method of claim 1, wherein the method reduces the individual's baseline CGI-I score by 1 or more; and wherein the method reduces the baseline CGI-S score by 1 or more, and attentiveness is increased by at least 10% as compared to an individual receiving only methylphenidate.

8. The method of claim 1, wherein the method reduces the individual's baseline CGI-I by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

9. The method of claim 1, wherein the individual's baseline CGI-S score is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

10. The method of claim 1, wherein the cyproheptadine is administered twice daily (b.i.d.).

11. The method of claim 1, wherein the therapeutically effective amount of cyproheptadine is 2 mg b.i.d or 4 mg b.i.d.

12. The method of claim 1, wherein the therapeutically effective amount of cyproheptadine is 2 mg/day.

13. The method of claim 1, wherein the therapeutically effective amount of cyproheptadine is 4 mg/day.

14. The method of claim 1, wherein the therapeutically effective amount of cyproheptadine is 8 mg/day.

15. The method of claim 1, wherein the method results in an increase in baseline weight by at least 0.5 pounds, at least 1 pound, at least 1.5 pounds, at least 2 pounds, at least 2.5 pounds, at least 3 pounds, at least 3.5 pounds, at least 4 pounds, at least 4.5 pounds, at least 5 pounds, at least 5.5 pounds, at least 6 pounds, at least 6.5 pounds, at least 7 pounds, at least 7.5 pounds, at least 8 pounds, at least 8.5 pounds, at least 9 pounds, at least 9.5 pounds, at least 10 pounds, at least 10.5 pounds, at least 11 pounds, at least 11.5 pounds, at least 12 pounds, at least 12.5 pounds, at least 13 pounds, at least 13.5 pounds, at least 14 pounds, at least 14.5 pounds, at least 15 pounds, at least 20 pounds, at least 25 pounds, at least 30 pounds, or at least 50 pounds.

16. The method of claim 1, wherein the methylphenidate and cyproheptadine are coadministered concomitantly.

17. The method of claim 1, wherein the increase in attentiveness is measured by the p academic performance rating scale, ADD evaluation scale-3rd edition (ADDES-3), ADHD rating scale-IV (ADHD-RS-IV), youth self-report (broadband instrument), Conners parent rating scale-revised (CPRS-R), Conners teacher rating scale-revised (CTRS-R), Conners 3 self-reporting scale (Conner 3-SR; ages 8-18y), home situations questionnaire-revised, inattention/overactivity with aggression (IOWA) Conners teacher's rating scale, Swanson Nolan and Pelham IV scale (SNAP-IV), Swanson Kotkin Agler M-Flynn and Pelham (SKAMP), Vanderbilt ADHD diagnostic parent rating scale (VADPRS), Vanderbilt ADHD diagnostic teacher rating scale (VADTRS), behavior assessment system for children-2nd edition (BASC-2) or the Conners rating scale long version.

18. The method of claim 1, wherein the cyproheptadine is administered in the morning and the mean peak plasma level of cyproheptadine is maintained through lunch.

19. A method of increasing attentiveness and weight velocity in an individual having an attention deficit disorder, the method comprising:

(i) coadministering to the individual methylphenidate and cyproheptadine on a first day during at least one of the morning or afternoon, wherein the cyproheptadine is not administered in the evening or before bedtime on the first day; and (ii) coadministering the methylphenidate and the cyproheptadine on a second day during at least one of the morning or afternoon, wherein the cyproheptadine is not administered in the evening or before bedtime on the second day;

wherein the method increases the individual's weight velocity and height velocity as compared to an individual receiving only methylphenidate;

wherein the methylphenidate and cyproheptadine are coadministered in therapeutically effective amounts;

wherein the dose of methylphenidate administered on the second day is increased relative to the dose of methylphenidate administered on the first day; and wherein the dose of cyproheptadine administered on the first day and the second day is maintained without concomitant weight loss.

* * * * *